US008137915B2

(12) United States Patent
Hugot et al.

(10) Patent No.: US 8,137,915 B2
(45) Date of Patent: *Mar. 20, 2012

(54) GENES INVOLVED IN INTESTINAL INFLAMMATORY DISEASES AND USE THEREOF

(75) Inventors: Jean Pierre Hugot, Paris (FR); Gilles Thomas, Paris (FR); Mohamed Zouali, Bagneux (FR); Suzanne Lesage, Sainte-Honorine (FR); Mathias Chamaillard, Joue-les-Tours (FR)

(73) Assignee: Fondation Jean Dausset-CEPH, Paris (FR)

( * ) Notice: Subject to any disclaimer, the term of this patent is extended or adjusted under 35 U.S.C. 154(b) by 113 days.

This patent is subject to a terminal disclaimer.

(21) Appl. No.: 12/370,543

(22) Filed: Feb. 12, 2009

(65) Prior Publication Data

US 2010/0159453 A1 Jun. 24, 2010

Related U.S. Application Data

(63) Continuation of application No. 10/240,046, filed as application No. PCT/FR01/00935 on Mar. 27, 2001, now Pat. No. 7,592,437.

(30) Foreign Application Priority Data

Mar. 27, 2000 (FR) ...................... 00 03832

(51) Int. Cl.
  *C12Q 1/68* (2006.01)
  *C07H 21/02* (2006.01)
  *C07H 21/04* (2006.01)
(52) U.S. Cl. ...................... 435/6.11; 536/23.1; 536/24.3
(58) Field of Classification Search .................. None
  See application file for complete search history.

(56) References Cited

U.S. PATENT DOCUMENTS

| 6,812,339 B1 | 11/2004 | Venter et al. |
| 6,835,815 B2 | 12/2004 | Nunez et al. |
| 6,858,391 B2 | 2/2005 | Nunez et al. |

FOREIGN PATENT DOCUMENTS

| EP | 1 074 617 A | 2/2001 |
| JP | 2001-570745 | 3/2004 |
| WO | WO 99 23255 A | 5/1999 |
| WO | WO 99 40102 A | 8/1999 |
| WO | WO 99 64576 A | 12/1999 |
| WO | WO 99/64576 A2 | 12/1999 |
| WO | WO 00 58473 A | 10/2000 |
| WO | WO 01/73028 A2 | 10/2001 |

OTHER PUBLICATIONS

Evans, William et al. Pharmacogenomics: Translating functional genomics into rational therapeutics Science 1999 vol. 286 pp. 487-491.*
Mummidi et al Evolution of human and non human primate CC chemokine receptor 5 gene and mRNA. Journal of Biological Chemistry 2000 vol. 275, No. 25, pp. 18946-18961.*
Barreiro, M et al. Assoication of NOD2/CARD15 mutations with previous surgical procedures in Crohn's disease. Rev Esp Enferm Dig 2005 vol. 97 No. 8 pp. 547-553.*
Barreiro-de Acosta, M et al. NOD2, CD!$, and TLR4 mutations do not influence response to adalimumab in patients with Crohn's idsease: a preliminary report. 2010 vol. 102 No. 10 pp. 591-595.*
Smith, Ben R. K. et al. Disease location, Anti-*Saccharomyces cerevisiae* antibody, nd NOD2/CARD15 genotype influence the progression of disease behavior in Crohn's disease. Inflamm Bowel Dis 2004 vol. 10 No. 5 pp. 521-528.*
Database EMBL Accession No. AC007728, Jun. 7, 1999, Doe Joint Genome Institute: "*Homo sapiens* chromosome 16 clone, RP11-327F22, Working Draft Sequence, 1 ordered pieces.", XP002156657.
Database EMBL Accession No. AC007608, May 21, 1999, Doe Joint Genome Institute, "*Homo sapiens* chromosome 16 clone RP11-401P9, Working Draft Sequence, 8 ordered pieces.", XP002156658.
Database EMBL Accession No. AQ534686, May 18, 1999, Zhao, S., et al.,: "RPCI-11-384F21.TJ RPCI-11, *Homo sapiens* genomic clone RPCI-11-384F21, genomic survey sequence.", XP002156659.
Database EMBL Accession No. AI681116, May 27, 1999, NCI-CGAP: "tx44b02.x1 NCI_CGAP_Lu24 *Homo sapiens* cDNA clone Image:2272395 3', mRNA sequence.", XP002156660.
Database EMBL Accession No. AQ585409, Jun. 9, 1999, Zhao, S., et al.: "RPCI-11-459C5.TV RPCI-11 *Homo sapiens* genomic clone RPCI-11-459C5, genomic survey sequence.", XP002156661.
Database EMBL Accession No. AI090427, Aug. 19, 1998, NCI-CGAP: "oy82d10.s1 NCI_CGAP_CLL1 *Homo sapiens* cDNA clone Image:1672339 3', mRNA sequence.", XP002156662.
Database EMBL Accession No. AQ176547, Sep. 21, 1998, Mahairas, G.G., et al., "HS_3213_B1_CO5_T7 CIT Approved Human Genomic Sperm Library D *Homo sapiens* genomic clone Plate=3213 Col=9 Row-F, genomic survey sequence.", XP002156663.
Database EMBL Accession No. AF178930, Nov. 23, 2000, Ogura, Y. et al.: "*Homo sapiens* NOD2 protein (NOD2) mRNA, complete cds.", XP002177310; Ogura, Y. et al., "Nod2, a Nod1/Apaf-1 Family Member that is Restricted to Monocytes and Activates NF-kappa B", The Journal of Biological Chemistry, vol. 276, No. 7, Feb. 16, 2001, pp. 4812-4818.
Hugot, Jean-Pierre et al., "Association of NOD2 leucine-rich repeat variants with susceptibility to Crohn's disease", Nature (London), vol. 411, No. 6837, 2001, pp. 599-603, XP002177308, ISSN: 0028-0836.
Database EMBL Accession No. AW082334, Oct. 18, 1999, NCI-CGAP: "xb65f03.x1 Soares_NFL_T_GBC_S1 *Homo sapiens* cDNA clone Image:2581181 3' similar to contains LTR1.t3 LTR1 repetitive element;, mRNA sequence.", XP002156664.
Database EMBL Accession No. AA282390, Apr. 4, 1997, NCI-CGAP: "zs89a11.rt NCI_CGAP_GCB1 *Homo sapiens* cDNA clone Image: 704636 5', mRNA sequence.", XP002156665.

(Continued)

*Primary Examiner* — Amanda Shaw
(74) *Attorney, Agent, or Firm* — Kilpatrick Townsend & Stockton LLP

(57) ABSTRACT

The invention concerns genes involved in inflammatory and/or immune diseases and some cancers, in particular intestinal cryptogenic inflammatory diseases, and proteins coded by these genes. The invention also concerns methods for diagnosing inflammatory diseases.

22 Claims, 4 Drawing Sheets

OTHER PUBLICATIONS

Database EMBL Accession No. AA278249, Apr. 3, 1997, NCI-CGAP: "zs77c05.r1 NCI_CGAP_GCB1 *Homo sapiens* cDNA clone Image: 703496 5', mRNA sequence.", XP002156666.

Database EMBL Accession No. AW134842, Oct. 29, 1999, NCI-CGAP: "UI-H-BI1-abs-e-09-0-UI.s1, NCI_CGAP_Sub3 *Homo sapiens* cDNA clone Image:2713048 3', mRNA sequence.", XP002156667.

Database EMBL Accession No. AW104269 Oct. 21, 1999, NCI-CGAP: "xd70h07.x1 Soares_NFL_T_GBC_S1 *Homo sapiens* cDNA clone Image:2603005 3' similar to contains Alu repetitive element; contains element MER22 repetitive element;, mRNA sequence.", XP002156668.

Database EMBL Accession No. AI377313, Jan. 28, 1999, NCI-CGAP: "te60b02.x1 Soares_NFL_T_GBC_S1 *Homo sapiens* cDNA clone Image:2091051 3' similar to contains element MSR1 MSR1 repetitive element;, mRNA sequence.", XP002156669.

Hugot, Jean-Pierre et al., "Mapping of a susceptibility locus for Crohn's disease on chromosome 16.", Nature (London), vol. 379, No. 6568, 1996, pp. 821-823, XP002156655, ISSN: 0028-0836.

Mirza Muddassar M. et al., "Evidence of linkage of the inflammatory bowel disease susceptibility locus on chromosome 16 (IBD1) to ulcerative colitis", Journal of Medical Genetics, vol. 35, No. 3, Mar. 1998, pp. 218-221, XP000971943, ISSN: 0022-2593.

Hugot, J.P. et al., "Fine mapping of the inflammatory bowel disease susceptibility locus 1 (IBD1) in the pericentromeric region of chromosome 16.", Gastroenterology, vol. 114, No. 4, Part 2, Apr. 15, 1998, p. A999, XP000971941, Digestive Diseases Week and the 99th Annual Meeting of the American Gastroenterological Association; New Orleans, Louisiana, USA; May 16-22, 1998; ISSN: 0016-5085.

Database Swissprot Accession No. Q9Y239, Inohara, N. et al., "NOD1 protein", XP002156670; Inohara, N. et al., "Nod 1, an Apaf-1-like activator of caspase-9 and nuclear factor-kappaB", The Journal of Biological Chemistry, vol. 274, No. 21, May 21, 1999, pp. 14560-14567, XP002156656.

Suggs et al.; PNAS, 1981, vol. 78, pp. 6613-6617.
Ogura et al.; J. Biol. Chem., vol. 276, (70): 4812-4818, Feb. 16, 2001.
Phillips, A.; J Pharm Pharmacology 53: 1169-1174, 2001.
Campbell et al.; Theriology 47(1): 63-72, 1997.
Wigley et al.; Reprod Fert. Dev. 6: 585-588, 1994.
Kaufman et al.; Blood 94: 3178-3184, 1999.
Wang et al.; Nuc. Acids Res. 27: 4609-4618, 1999.
Check Nature 422:7, 2003.
Touchette, Nat. Med. 2(1) 7-8, 1996.
Verma et al.; Nature 389: 239-242, 1997.
Rosenberg et al.; Science 287: 1751, 2000.
Juengst BMJ, 326:1410-11, 2003.
Couzin et al.; Science 307:1028, 2005.
Anderson et al.; Nature, 293:25-30, Supp. Apr. 30, 1998.
Goncalves, Bioassays; 27(5):506-517, 2005.
Bowie et al.; Science, Mar. 1990; vol. 247, pp. 1307-1310.

* cited by examiner

SEQUENCE LISTING

```
<160> NUMBER OF SEQ ID NOS: 90

<210> SEQ ID NO 1
<211> LENGTH: 4374
<212> TYPE: DNA
<213> ORGANISM: Homo sapiens
<220> FEATURE:
<223> OTHER INFORMATION: IBD1 cDNA
<220> FEATURE:
<221> NAME/KEY: CDS
<222> LOCATION: (1)..(3126)
<223> OTHER INFORMATION: IBD1 plus putative additional 5' exon

<400> SEQUENCE: 1 atg gag aag aga agg ggt cta acc att gag tgc tgg ggc ccc caa agt        48
Met Glu Lys Arg Arg Gly Leu Thr Ile Glu Cys Trp Gly Pro Gln Ser
 1               5                  10                  15 ccc tca ctg acc ttg ttc tcc tcc cca ggt tgt gaa atg tgc tcg cag        96
Pro Ser Leu Thr Leu Phe Ser Ser Pro Gly Cys Glu Met Cys Ser Gln
             20                  25                  30 gag gct ttt cag gca cag agg agc cag ctg gtc gag ctg ctg gtc tca       144
Glu Ala Phe Gln Ala Gln Arg Ser Gln Leu Val Glu Leu Leu Val Ser
         35                  40                  45 ggg tcc ctg gaa ggc ttc gag agt gtc ctg gac tgg ctg ctg tcc tgg       192
Gly Ser Leu Glu Gly Phe Glu Ser Val Leu Asp Trp Leu Leu Ser Trp
     50                  55                  60 gag gtc ctc tcc tgg gag gac tac gag ggc ttc cac ctc ctg ggc cag       240
Glu Val Leu Ser Trp Glu Asp Tyr Glu Gly Phe His Leu Leu Gly Gln
 65                  70                  75                  80 cct ctc tcc cac ttg gcc agg cgc ctt ctg gac acc gtc tgg aat aag       288
Pro Leu Ser His Leu Ala Arg Arg Leu Leu Asp Thr Val Trp Asn Lys
                 85                  90                  95 ggt act tgg gcc tgt cag aag ctc atc gcg gct gcc caa gaa gcc cag       336
Gly Thr Trp Ala Cys Gln Lys Leu Ile Ala Ala Ala Gln Glu Ala Gln
            100                 105                 110 gcc gac agc cag tcc ccc aag ctg cat ggc tgc tgg gac ccc cac tcg       384
Ala Asp Ser Gln Ser Pro Lys Leu His Gly Cys Trp Asp Pro His Ser
        115                 120                 125 ctc cac cca gcc cga gac ctg cag agt cac cgg cca gcc att gtc agg       432
Leu His Pro Ala Arg Asp Leu Gln Ser His Arg Pro Ala Ile Val Arg
    130                 135                 140 agg ctc cac agc cat gtg gag aac atg ctg gac ctg gca tgg gag cgg       480
Arg Leu His Ser His Val Glu Asn Met Leu Asp Leu Ala Trp Glu Arg
145                 150                 155                 160 ggt ttc gtc agc cag tat gaa tgt gat gaa atc agg ttg ccg atc ttc       528
Gly Phe Val Ser Gln Tyr Glu Cys Asp Glu Ile Arg Leu Pro Ile Phe
                165                 170                 175 aca ccg tcc cag agg gca aga agg ctg ctt gat ctt gcc acg gtg aaa       576
```

|  |  |  |  |  |  |  |  |  |  |  |  |  |  |
|---|---|---|---|---|---|---|---|---|---|---|---|---|---|
| Thr | Pro | Ser | Gln | Arg | Ala | Arg | Arg | Leu | Leu | Asp | Leu | Ala | Thr | Val | Lys |
|  |  |  | 180 |  |  |  | 185 |  |  |  | 190 |  |  |

```
gcg aat gga ttg gct gcc ttc ctt cta caa cat gtt cag gaa tta cca    624
Ala Asn Gly Leu Ala Ala Phe Leu Leu Gln His Val Gln Glu Leu Pro
        195                 200                 205 gtc cca ttg gcc ctg cct ttg gaa gct gcc aca tgc aag aag tat atg    672
Val Pro Leu Ala Leu Pro Leu Glu Ala Ala Thr Cys Lys Lys Tyr Met
        210                 215                 220 gcc aag ctg agg acc acg gtg tct gct cag tct cgc ttc ctc agt acc    720
Ala Lys Leu Arg Thr Thr Val Ser Ala Gln Ser Arg Phe Leu Ser Thr
225                 230                 235                 240 tat gat gga gca gag acg ctc tgc ctg gag gac ata tac aca gag aat    768
Tyr Asp Gly Ala Glu Thr Leu Cys Leu Glu Asp Ile Tyr Thr Glu Asn
                245                 250                 255 gtc ctg gag gtc tgg gca gat gtg ggc atg gct gga tcc ccg cag aag    816
Val Leu Glu Val Trp Ala Asp Val Gly Met Ala Gly Ser Pro Gln Lys
                    260                 265                 270 agc cca gcc acc ctg ggc ctg gag gag ctc ttc agc acc cct ggc cac    864
Ser Pro Ala Thr Leu Gly Leu Glu Glu Leu Phe Ser Thr Pro Gly His
            275                 280                 285 ctc aat gac gat gcg gac act gtg ctg gtg gtg ggt gag gcg ggc agt    912
Leu Asn Asp Asp Ala Asp Thr Val Leu Val Val Gly Glu Ala Gly Ser
        290                 295                 300 ggc aag agc acg ctc ctg cag cgg ctg cac ttg ctg tgg gct gca ggg    960
Gly Lys Ser Thr Leu Leu Gln Arg Leu His Leu Leu Trp Ala Ala Gly
305                 310                 315                 320 caa gac ttc cag gaa ttt ctc ttt gtc ttc cca ttc agc tgc cgg cag   1008
Gln Asp Phe Gln Glu Phe Leu Phe Val Phe Pro Phe Ser Cys Arg Gln
                325                 330                 335 ctg cag tgc atg gcc aaa cca ctc tct gtg cgg act cta ctc ttt gag   1056
Leu Gln Cys Met Ala Lys Pro Leu Ser Val Arg Thr Leu Leu Phe Glu
            340                 345                 350 cac tgc tgt tgg cct gat gtt ggt caa gaa gac atc ttc cag tta ctc   1104
His Cys Cys Trp Pro Asp Val Gly Gln Glu Asp Ile Phe Gln Leu Leu
        355                 360                 365 ctt gac cac cct gac cgt gtc ctg tta acc ttt gat ggc ttt gac gag   1152
Leu Asp His Pro Asp Arg Val Leu Leu Thr Phe Asp Gly Phe Asp Glu
370                 375                 380 ttc aag ttc agg ttc acg gat cgt gaa cgc cac tgc tcc ccg acc gac   1200
Phe Lys Phe Arg Phe Thr Asp Arg Glu Arg His Cys Ser Pro Thr Asp
385                 390                 395                 400 ccc acc tct gtc cag acc ctg ctc ttc aac ctt ctg cag ggc aac ctg   1248
Pro Thr Ser Val Gln Thr Leu Leu Phe Asn Leu Leu Gln Gly Asn Leu
                405                 410                 415 ctg aag aat gcc cgc aag gtg gtg acc agc cgt ccg gcc gct gtg tcg   1296
Leu Lys Asn Ala Arg Lys Val Val Thr Ser Arg Pro Ala Ala Val Ser
            420                 425                 430 gcg ttc ctc agg aag tac atc cgc acc gag ttc aac ctc aag ggc ttc   1344
Ala Phe Leu Arg Lys Tyr Ile Arg Thr Glu Phe Asn Leu Lys Gly Phe
        435                 440                 445 tct gaa cag ggc atc gag ctg tac ctg agg aag cgt cat cat gag ccc   1392
Ser Glu Gln Gly Ile Glu Leu Tyr Leu Arg Lys Arg His His Glu Pro
450                 455                 460 ggg gtg gcg gac cgc ctc atc cgc ctg ctc caa gag tca gcc ctg   1440
Gly Val Ala Asp Arg Leu Ile Arg Leu Leu Gln Glu Thr Ser Ala Leu
465                 470                 475                 480 cac ggt ttg tgc cac ctg cct gtc ttc tca tgg atg gtg tcc aaa tgc   1488
His Gly Leu Cys His Leu Pro Val Phe Ser Trp Met Val Ser Lys Cys
                485                 490                 495 cac cag gaa ctg ttg ctg cag gag ggg ggg tcc cca aag acc act aca   1536
```

```
             His Gln Glu Leu Leu Gln Glu Gly Gly Ser Pro Lys Thr Thr Thr
                         500                 505                 510 gat atg tac ctg ctg att ctg cag cat ttt ctg ctg cat gcc acc ccc        1584
Asp Met Tyr Leu Leu Ile Leu Gln His Phe Leu Leu His Ala Thr Pro
            515                 520                 525 cca gac tca gct tcc caa ggt ctg gga ccc agt ctt ctt cgg ggc cgc        1632
Pro Asp Ser Ala Ser Gln Gly Leu Gly Pro Ser Leu Leu Arg Gly Arg
        530                 535                 540 ctc ccc acc ctc ctg cac ctg ggc aga ctg gct ctg tgg ggc ctg ggc        1680
Leu Pro Thr Leu Leu His Leu Gly Arg Leu Ala Leu Trp Gly Leu Gly
545                 550                 555                 560 atg tgc tgc tac gtg ttc tca gcc cag cag ctc cag gca gca cag gtc        1728
Met Cys Cys Tyr Val Phe Ser Ala Gln Gln Leu Gln Ala Ala Gln Val
                565                 570                 575 agc cct gat gac att tct ctt ggc ttc ctg gtg cgt gcc aaa ggt gtc        1776
Ser Pro Asp Asp Ile Ser Leu Gly Phe Leu Val Arg Ala Lys Gly Val
            580                 585                 590 gtg cca ggg agt acg gcg ccc ctg gaa ttc ctt cac atc act ttc cag        1824
Val Pro Gly Ser Thr Ala Pro Leu Glu Phe Leu His Ile Thr Phe Gln
        595                 600                 605 tgc ttc ttt gcc gcg ttc tac ctg gca ctc agt gct gat gtg cca cca        1872
Cys Phe Phe Ala Ala Phe Tyr Leu Ala Leu Ser Ala Asp Val Pro Pro
610                 615                 620 gct ttg ctc aga cac ctc ttc aat tgt ggc agg cca ggc aac tca cca        1920
Ala Leu Leu Arg His Leu Phe Asn Cys Gly Arg Pro Gly Asn Ser Pro
625                 630                 635                 640 atg gcc agg ctc ctg ccc acg atg tgc atc cag gcc tcg gag gga aag        1968
Met Ala Arg Leu Leu Pro Thr Met Cys Ile Gln Ala Ser Glu Gly Lys
                645                 650                 655 gac agc agc gtg gca gct ttg ctg cag aag gcc gag ccg cac aac ctt        2016
Asp Ser Ser Val Ala Ala Leu Leu Gln Lys Ala Glu Pro His Asn Leu
            660                 665                 670 cag atc aca gca gcc ttc ctg gca ggg ctg ttg tcc cgg gag cac tgg        2064
Gln Ile Thr Ala Ala Phe Leu Ala Gly Leu Leu Ser Arg Glu His Trp
        675                 680                 685 ggc ctg ctg gct gag tgc cag aca tct gag aag gcc ctg ctc cgg cgc        2112
Gly Leu Leu Ala Glu Cys Gln Thr Ser Glu Lys Ala Leu Leu Arg Arg
690                 695                 700 cag gcc tgt gcc cgc tgg tgt ctg gcc cgc agc ctc cgc aag cac ttc        2160
Gln Ala Cys Ala Arg Trp Cys Leu Ala Arg Ser Leu Arg Lys His Phe
705                 710                 715                 720 cac tcc atc ccg cca gct gca ccg ggt gag gcc aag agc gtg cat gcc        2208
His Ser Ile Pro Pro Ala Ala Pro Gly Glu Ala Lys Ser Val His Ala
                725                 730                 735 atg ccc ggg ttc atc tgg ctc atc cgg agc ctg tac gag atg cag gag        2256
Met Pro Gly Phe Ile Trp Leu Ile Arg Ser Leu Tyr Glu Met Gln Glu
            740                 745                 750 gag cgg ctg gct cgg aag gct gca cgt ggc ctg aat gtt ggg cac ctc        2304
Glu Arg Leu Ala Arg Lys Ala Ala Arg Gly Leu Asn Val Gly His Leu
        755                 760                 765 aag ttg aca ttt tgc agt gtg ggc ccc act gag tgt gct gcc ctg gcc        2352
Lys Leu Thr Phe Cys Ser Val Gly Pro Thr Glu Cys Ala Ala Leu Ala
770                 775                 780 ttt gtg ctg cag cac ctt cgg cgg ccc gtg gcc ctg cag ctg gac tac        2400
Phe Val Leu Gln His Leu Arg Arg Pro Val Ala Leu Gln Leu Asp Tyr
785                 790                 795                 800 aac tct gtg ggt gac att ggc gtg gag cag ctg ctg cct tgc ctt ggt        2448
Asn Ser Val Gly Asp Ile Gly Val Glu Gln Leu Leu Pro Cys Leu Gly
                805                 810                 815 gtc tgc aag gct ctg tat ttg cgc gat aac aat atc tca gac cga ggc        2496
```

```
                                                      -continued

Val Cys Lys Ala Leu Tyr Leu Arg Asp Asn Ile Ser Asp Arg Gly
            820                 825                 830 atc tgc aag ctc att gaa tgt gct ctt cac tgc gag caa ttg cag aag    2544
Ile Cys Lys Leu Ile Glu Cys Ala Leu His Cys Glu Gln Leu Gln Lys
                835                 840                 845 tta gct cta ttc aac aac aaa ttg act gac ggc tgt gca cac tcc atg    2592
Leu Ala Leu Phe Asn Asn Lys Leu Thr Asp Gly Cys Ala His Ser Met
            850                 855                 860 gct aag ctc ctt gca tgc agg cag aac ttc ttg gca ttg agg ctg ggg    2640
Ala Lys Leu Leu Ala Cys Arg Gln Asn Phe Leu Ala Leu Arg Leu Gly
865             870                 875                 880 aat aac tac atc act gcc gcg gga gcc caa gtg ctg gcc gag ggg ctc    2688
Asn Asn Tyr Ile Thr Ala Ala Gly Ala Gln Val Leu Ala Glu Gly Leu
            885                 890                 895 cga ggc aac acc tcc ttg cag ttc ctg gga ttc tgg ggc aac aga gtg    2736
Arg Gly Asn Thr Ser Leu Gln Phe Leu Gly Phe Trp Gly Asn Arg Val
            900                 905                 910 ggt gac gag ggg gcc cag gcc ctg gct gaa gcc ttg ggt gat cac cag    2784
Gly Asp Glu Gly Ala Gln Ala Leu Ala Glu Ala Leu Gly Asp His Gln
            915                 920                 925 agc ttg agg tgg ctc agc ctg gtg ggg aac aac att ggc agt gtg ggt    2832
Ser Leu Arg Trp Leu Ser Leu Val Gly Asn Asn Ile Gly Ser Val Gly
930             935                 940 gcc caa gcc ttg gca ctg atg ctg gca aag aac gtc atg cta gaa gaa    2880
Ala Gln Ala Leu Ala Leu Met Leu Ala Lys Asn Val Met Leu Glu Glu
945             950                 955                 960 ctc tgc ctg gag gag aac cat ctc cag gat gaa ggt gta tgt tct ctc    2928
Leu Cys Leu Glu Glu Asn His Leu Gln Asp Glu Gly Val Cys Ser Leu
                965                 970                 975 gca gaa gga ctg aag aaa aat tca agt ttg aaa atc ctg aag ttg tcc    2976
Ala Glu Gly Leu Lys Lys Asn Ser Ser Leu Lys Ile Leu Lys Leu Ser
                980                 985                 990 aat aac tgc atc acc tac cta ggg gca gaa gcc ctc ctg cag gcc ctt    3024
Asn Asn Cys Ile Thr Tyr Leu Gly Ala Glu Ala Leu Leu Gln Ala Leu
            995                 1000                1005 gaa agg aat gac acc atc ctg gaa gtc tgg ctc cga ggg aac act ttc    3072
Glu Arg Asn Asp Thr Ile Leu Glu Val Trp Leu Arg Gly Asn Thr Phe
            1010                1015                1020 tct cta gag gag gtt gac aag ctc ggc tgc agg gac acc aga ctc ttg    3120
Ser Leu Glu Glu Val Asp Lys Leu Gly Cys Arg Asp Thr Arg Leu Leu
1025            1030                1035                1040 ctt tga agtctccggg aggatgttcg tctcagtttg tttgtgagca ggctgtgagt     3176
Leu ttgggcccca gaggctgggt gacatgtgtt ggcagcctct tcaaaatgag ccctgtcctg    3236
cctaaggctg aacttgtttt ctgggaacac cataggtcac cttttattctg gcagaggagg    3296 gagcatcagt gccctccagg atagactttt cccaagccta cttttgccat tgacttcttc    3356
ccaagattca atcccaggat gtacaaggac agcccctcct ccatagtatg ggactggcct    3416
ctgctgatcc tcccaggctt ccgtgtgggt cagtggggcc catggatgtg cttgttaact    3476
gagtgccttt tggtggagag gcccggccct ctcacaaaag accccttacc actgctctga    3536
tgaagaggag tacacagaaa cataattcag gaagcagctt tccccatgtc tcgactcatc    3596
catccaggcc attcccgtc tctggttcct cccctcctcc tggactcctg cacacgctcc      3656
ttcctctgag gctgaaattc agaatattag tgacctcagc tttgatattt cacttacagc    3716 accccccaacc ctggcaccca gggtgggaag ggctacacct tagcctgccc tcctttccgg    3776
tgtttaagac attttttggaa ggggacacgt gacagccgtt tgttccccaa gacattctag    3836
```

-continued

```
gtttgcaaga aaaatatgac cacactccag ctgggatcac atgtggactt ttatttccag    3896
tgaaatcagt tactcttcag ttaagccttt ggaaacagct cgactttaaa aagctccaaa    3956
tgcagcttta aaaattaat ctgggccaga atttcaaacg gcctcactag gcttctggtt    4016
gatgcctgtg aactgaactc tgacaacaga cttctgaaat agacccacaa gaggcagttc    4076
catttcattt gtgccagaat gctttaggat gtacagttat ggattgaaag tttacaggaa    4136
aaaaaattag gccgttcctt caaagcaaat gtcttcctgg attattcaaa atgatgtatg    4196
ttgaagcctt tgtaaattgt cagatgctgt gcaaatgtta ttattttaaa cattatgatg    4256
tgtgaaaact ggttaatatt tataggtcac tttgttttac tgtcttaagt ttatactctt    4316
atagacaaca tggccgtgaa ctttatgctg taaataatca gagggaata aactgttg     4374
```

<210> SEQ ID NO 2
<211> LENGTH: 1041
<212> TYPE: PRT
<213> ORGANISM: Homo sapiens
<220> FEATURE:
<223> OTHER INFORMATION: IBD1 plus putative additional 5' exon

<400> SEQUENCE: 2

```
Met Glu Lys Arg Arg Gly Leu Thr Ile Glu Cys Trp Gly Pro Gln Ser
  1               5                  10                  15

Pro Ser Leu Thr Leu Phe Ser Ser Pro Gly Cys Glu Met Cys Ser Gln
             20                  25                  30

Glu Ala Phe Gln Ala Gln Arg Ser Gln Leu Val Glu Leu Leu Val Ser
         35                  40                  45

Gly Ser Leu Glu Gly Phe Glu Ser Val Leu Asp Trp Leu Leu Ser Trp
     50                  55                  60

Glu Val Leu Ser Trp Glu Asp Tyr Glu Gly Phe His Leu Leu Gly Gln
 65                  70                  75                  80

Pro Leu Ser His Leu Ala Arg Arg Leu Leu Asp Thr Val Trp Asn Lys
                 85                  90                  95

Gly Thr Trp Ala Cys Gln Lys Leu Ile Ala Ala Gln Glu Ala Gln
            100                 105                 110

Ala Asp Ser Gln Ser Pro Lys Leu His Gly Cys Trp Asp Pro His Ser
        115                 120                 125

Leu His Pro Ala Arg Asp Leu Gln Ser His Arg Pro Ala Ile Val Arg
    130                 135                 140

Arg Leu His Ser His Val Glu Asn Met Leu Asp Leu Ala Trp Glu Arg
145                 150                 155                 160

Gly Phe Val Ser Gln Tyr Glu Cys Asp Glu Ile Arg Leu Pro Ile Phe
                165                 170                 175

Thr Pro Ser Gln Arg Ala Arg Arg Leu Leu Asp Leu Ala Thr Val Lys
            180                 185                 190

Ala Asn Gly Leu Ala Ala Phe Leu Leu Gln His Val Gln Glu Leu Pro
        195                 200                 205

Val Pro Leu Ala Leu Pro Leu Glu Ala Ala Thr Cys Lys Lys Tyr Met
    210                 215                 220

Ala Lys Leu Arg Thr Thr Val Ser Ala Gln Ser Arg Phe Leu Ser Thr
225                 230                 235                 240

Tyr Asp Gly Ala Glu Thr Leu Cys Leu Glu Asp Ile Tyr Thr Glu Asn
                245                 250                 255

Val Leu Glu Val Trp Ala Asp Val Gly Met Ala Gly Ser Pro Gln Lys
            260                 265                 270

Ser Pro Ala Thr Leu Gly Leu Glu Glu Leu Phe Ser Thr Pro Gly His
```

-continued

```
            275                 280                 285
Leu Asn Asp Asp Ala Asp Thr Val Leu Val Val Gly Glu Ala Gly Ser
290                 295                 300
Gly Lys Ser Thr Leu Leu Gln Arg Leu His Leu Leu Trp Ala Ala Gly
305                 310                 315                 320
Gln Asp Phe Gln Glu Phe Leu Phe Val Phe Pro Phe Ser Cys Arg Gln
                325                 330                 335
Leu Gln Cys Met Ala Lys Pro Leu Ser Val Arg Thr Leu Leu Phe Glu
                340                 345                 350
His Cys Cys Trp Pro Asp Val Gly Gln Glu Asp Ile Phe Gln Leu Leu
                355                 360                 365
Leu Asp His Pro Asp Arg Val Leu Leu Thr Phe Asp Gly Phe Asp Glu
370                 375                 380
Phe Lys Phe Arg Phe Thr Asp Arg Glu Arg His Cys Ser Pro Thr Asp
385                 390                 395                 400
Pro Thr Ser Val Gln Thr Leu Leu Phe Asn Leu Leu Gln Gly Asn Leu
                405                 410                 415
Leu Lys Asn Ala Arg Lys Val Val Thr Ser Arg Pro Ala Ala Val Ser
                420                 425                 430
Ala Phe Leu Arg Lys Tyr Ile Arg Thr Glu Phe Asn Leu Lys Gly Phe
                435                 440                 445
Ser Glu Gln Gly Ile Glu Leu Tyr Leu Arg Lys Arg His His Glu Pro
                450                 455                 460
Gly Val Ala Asp Arg Leu Ile Arg Leu Leu Gln Glu Thr Ser Ala Leu
465                 470                 475                 480
His Gly Leu Cys His Leu Pro Val Phe Ser Trp Met Val Ser Lys Cys
                485                 490                 495
His Gln Glu Leu Leu Leu Gln Glu Gly Gly Ser Pro Lys Thr Thr Thr
                500                 505                 510
Asp Met Tyr Leu Leu Ile Leu Gln His Phe Leu Leu His Ala Thr Pro
                515                 520                 525
Pro Asp Ser Ala Ser Gln Gly Leu Gly Pro Ser Leu Leu Arg Gly Arg
                530                 535                 540
Leu Pro Thr Leu Leu His Leu Gly Arg Leu Ala Leu Trp Gly Leu Gly
545                 550                 555                 560
Met Cys Cys Tyr Val Phe Ser Ala Gln Gln Leu Gln Ala Ala Gln Val
                565                 570                 575
Ser Pro Asp Asp Ile Ser Leu Gly Phe Leu Val Arg Ala Lys Gly Val
                580                 585                 590
Val Pro Gly Ser Thr Ala Pro Leu Glu Phe Leu His Ile Thr Phe Gln
                595                 600                 605
Cys Phe Phe Ala Ala Phe Tyr Leu Ala Leu Ser Ala Asp Val Pro Pro
                610                 615                 620
Ala Leu Leu Arg His Leu Phe Asn Cys Gly Arg Pro Gly Asn Ser Pro
625                 630                 635                 640
Met Ala Arg Leu Leu Pro Thr Met Cys Ile Gln Ala Ser Glu Gly Lys
                645                 650                 655
Asp Ser Ser Val Ala Ala Leu Leu Gln Lys Ala Glu Pro His Asn Leu
                660                 665                 670
Gln Ile Thr Ala Ala Phe Leu Ala Gly Leu Leu Ser Arg Glu His Trp
                675                 680                 685
Gly Leu Leu Ala Glu Cys Gln Thr Ser Glu Lys Ala Leu Leu Arg Arg
690                 695                 700
```

```
Gln Ala Cys Ala Arg Trp Cys Leu Ala Arg Ser Leu Arg Lys His Phe
705                 710                 715                 720

His Ser Ile Pro Pro Ala Ala Pro Gly Glu Ala Lys Ser Val His Ala
            725                 730                 735

Met Pro Gly Phe Ile Trp Leu Ile Arg Ser Leu Tyr Glu Met Gln Glu
            740                 745                 750

Glu Arg Leu Ala Arg Lys Ala Arg Gly Leu Asn Val Gly His Leu
        755                 760                 765

Lys Leu Thr Phe Cys Ser Val Gly Pro Thr Glu Cys Ala Ala Leu Ala
770                 775                 780

Phe Val Leu Gln His Leu Arg Arg Pro Val Ala Leu Gln Leu Asp Tyr
785                 790                 795                 800

Asn Ser Val Gly Asp Ile Gly Val Glu Gln Leu Leu Pro Cys Leu Gly
                805                 810                 815

Val Cys Lys Ala Leu Tyr Leu Arg Asp Asn Asn Ile Ser Asp Arg Gly
            820                 825                 830

Ile Cys Lys Leu Ile Glu Cys Ala Leu His Cys Glu Gln Leu Gln Lys
        835                 840                 845

Leu Ala Leu Phe Asn Asn Lys Leu Thr Asp Gly Cys Ala His Ser Met
850                 855                 860

Ala Lys Leu Leu Ala Cys Arg Gln Asn Phe Leu Ala Leu Arg Leu Gly
865                 870                 875                 880

Asn Asn Tyr Ile Thr Ala Ala Gly Ala Gln Val Leu Ala Glu Gly Leu
                885                 890                 895

Arg Gly Asn Thr Ser Leu Gln Phe Leu Gly Phe Trp Gly Asn Arg Val
            900                 905                 910

Gly Asp Glu Gly Ala Gln Ala Leu Ala Glu Ala Leu Gly Asp His Gln
        915                 920                 925

Ser Leu Arg Trp Leu Ser Leu Val Gly Asn Asn Ile Gly Ser Val Gly
930                 935                 940

Ala Gln Ala Leu Ala Leu Met Leu Ala Lys Asn Val Met Leu Glu Glu
945                 950                 955                 960

Leu Cys Leu Glu Glu Asn His Leu Gln Asp Glu Gly Val Cys Ser Leu
                965                 970                 975

Ala Glu Gly Leu Lys Lys Asn Ser Ser Leu Lys Ile Leu Lys Leu Ser
            980                 985                 990

Asn Asn Cys Ile Thr Tyr Leu Gly Ala Glu Ala Leu Leu Gln Ala Leu
        995                 1000                1005

Glu Arg Asn Asp Thr Ile Leu Glu Val Trp Leu Arg Gly Asn Thr Phe
    1010                1015                1020

Ser Leu Glu Glu Val Asp Lys Leu Gly Cys Arg Asp Thr Arg Leu Leu
1025                1030                1035                1040

Leu

<210> SEQ ID NO 3
<211> LENGTH: 37443
<212> TYPE: DNA
<213> ORGANISM: Homo sapiens
<220> FEATURE:
<223> OTHER INFORMATION: IBD1 genomic sequence
<220> FEATURE:
<221> NAME/KEY: exon
<222> LOCATION: (63)..(106)
<220> FEATURE:
<221> NAME/KEY: exon
<222> LOCATION: (3908)..(4406)
<220> FEATURE:
<221> NAME/KEY: exon
```

```
<222> LOCATION: (12307)..(12412)
<220> FEATURE:
<221> NAME/KEY: exon
<222> LOCATION: (15010)..(16825)
<220> FEATURE:
<221> NAME/KEY: exon
<222> LOCATION: (21017)..(21100)
<220> FEATURE:
<221> NAME/KEY: exon
<222> LOCATION: (21321)..(21404)
<220> FEATURE:
<221> NAME/KEY: exon
<222> LOCATION: (24355)..(24438)
<220> FEATURE:
<221> NAME/KEY: exon
<222> LOCATION: (27052)..(27135)
<220> FEATURE:
<221> NAME/KEY: exon
<222> LOCATION: (27730)..(27813)
<220> FEATURE:
<221> NAME/KEY: exon
<222> LOCATION: (29917)..(30000)
<220> FEATURE:
<221> NAME/KEY: exon
<222> LOCATION: (34244)..(34327)
<220> FEATURE:
<221> NAME/KEY: exon
<222> LOCATION: (36123)..(37443)

<400> SEQUENCE: 3
tcaccatata actggtattt aaagccacaa gagcaggtgg gctcatctag ggatggagtg      60
atatggagaa gagaaggggt ctaaccattg agtgctgggg cccccagtgt taggaaccag     120
ccaagaagac agaaagagtg aaaatcagag agttggggtg tcctggagga aatgaagaaa     180
atgccccaaa gaggaaggag ggaacaaata tgaccaatgc ccctggcaga gcaagcaggc     240
tgagggctga ggattgagca atgggaggtc actggtgaca gtttcactgg agctggatgg     300
ggaactagag ggaatgggag gggatgggag gacttgggga cagcagtaca ggcaacagac     360
aagggggcct gctgtaaagg gagcagataa atgggattgg agccaaatga agaagggag      420 tgtcaagaga gtgctttact tttacaatgg agaattagag tgcattgtgc actggtgggg     480
ggatttgatc tcttagggag agaacagtgt tagggaggga gaatgcagga tagctggggg     540
agggtggggg gcttggcccc agcagagact caggacactt gggaagttga gcttccctgg     600
gcttcccctc ctctcctgtc tgcaaggggt cagtgggctg agatttcagc acttaagcaa     660
agcatttgct cttggcccca gagaaaccgg gctggctgtg gtctcaggaa ggaaggaggt     720
gtccaggctc aggcctgggc ctgggtttca ggagggccc acgtgggtca cccctttgacc    780 ctctctttca gcaaggaagt gatccttttct ctacatgggc ctcaccttgg ggaggacaat   840
ggtgtctttg aagttgtagt aactgaagta gagatcaaaa ggcaatgcag atagactgac    900
agatttcgcc tgaagagggg aagcccgacc aggtaataaa ggagtaagag gaaggatgtt    960
aaggacaatt ttaggaaaca gataatgagt gaatatttt tctctctctt tcccaattta    1020
aactgaagca ggagaaactg aagctagaca taatgattaa cttcccaagc tggtgagctt   1080
cctgagctgg ttagtgagaa cagcactaag gccaggttct cctccccaga tgtttaagat    1140
gagacaggac aatgcctgct cagagacagg gcctggctga attggccctc aggattctct   1200
ctgctctgag gtttctggaa gaaggccagg gcagaggtgt ggtgatgtag ctgctgggag   1260
gacagagctc cgagtcacgt ggcttgggcg ggcctcccct tcctggtgtc cacagaagcc   1320
caacgtcact agctggggtg tgtatggctc acacgtaggc caggctgccc taggcttggt   1380
gtgcaaggga gggccccta cttacttgtg gcctgtcccc tcgtgaatgt gtctcatgtc    1440
cccagtgggg tttttcagtg agggtcatgg tctccaggat gcacaaggct tgtgccaga    1500
```

```
attgcttgga attgcctagt tctggaaggc tggttggcca actctggcct ccggcttttc    1560
ctttgggaat ttcccttgaa ggtggggttg gtagacagat ccaggctcac cagtcctgtg    1620
ccactgggct tttggcattc tgcacaaggc ctacccgcag atgccatgcc tgctccccca    1680
gcctaatggg ctttgatggg ggaagagggt ggttcagcct ctcacgatga ggaggaaaga    1740
gcaagtgtcc tcctcggaca ttctcccggg aagaggagca ggcattgtcc cgtcccagct    1800
tgatcctcag ccttctttca tccttggccg cgacatgctc ccaggctggg ggtcagatgg    1860
ggagtgctga ctctgtttct gggctgtttt ctggggagaa tgggtcggcg gttttttttc    1920
cccaggacct gggcagggtc aatggtgggg gccgctgtcg catccttggc tggtgtttcc    1980
acagctgaga accactccag ggccaagccc agagcttatt ctacccttt ttgtcctctc    2040 ttcccctgtc ctcggccacc ccaccctctt ggctcctctg cttagatgtg ggcacaagga    2100
ggagaactcc ttggcctgag agaactacct tagatcctgg cttccagtgg cctctgcagg    2160
ggggtacacc ctctctccca agcagccaga cacacaagta acctcattgc ctcagtttcc    2220
ccatctgacc agcacagggc cccctgtgcc ccagcagcgt tctgagagat tggagctttc    2280
tccttttgct taccttggct accgtatgag gacggataca gagtgttccc cccaccccca    2340
gcccagggga tatttgattc atgaacattc cctcagtgtc tttgtggggg acaatgctgt    2400
gccaggctca gggatgccag gacgagtaag acccaggctc ccacgtgcc caggcaggga    2460 gagagacaca taaacaacca tcaggaaaga ggtaaaatcc ccaggccact tggcatctgc    2520
tcccttgagt gtctgggaat gtccctgatt tataaaaaga agctgacggc cctctttgtt    2580
gtccatgcct acaccctttc actttcgttt cttcggggca ctgcagcagc ccttgtccac    2640
agaccccatg acaatcgcag aactgaccat gctgagagat tttcttggct gctcagggac    2700
cctgccaggg cttgaagctc ctggagggtc acttgccctc aaattcccag aacgcacagc    2760
aggtcactga tgatagcagt ggcagcagtc tgtgcacggt ggtttcgagg gcgtgggagg    2820
gaggtgaggg ccctagggca agtgtgtgtg ggaagtgttg atgggggaca aggcaccaga    2880
acgctcggaa acaacttagt ttgcaccgta attttcact tcgcctagga caggaccttt    2940
agagcaatat tctgagtcta cccttggag tagcagtgtg caaaacacac agcacgggct    3000
tggggccccc gtggggaacc caatgtaag agttagagac atgcattccg gagtcataca    3060
tggctcgtgt tgaaatcctg actctgcctg tctagctgtg acacatcgta caaatcactt    3120
agcttcttgg tgcctcagtg tcttcctctg tagaatgggt agatcatagg cactacttca    3180
gagtggctgg gagggttcag tgaattcctg caggagagca cttagaatgg cacttggtgt    3240
gtagtttatg cttaattaat attagccgtt actgaaactg ctgtagcctg aatccagcca    3300
gcatgaaaga gcccctctca ccctgcttcg aagagaatga attccctgat tgtttggaag    3360
atctctctct ctctctctgt cttttttttt tttttttgag aaacggtctt gctctcttgc    3420
ccaggctgga gcgcaatggt gccatcttgg ctcactgcaa cctctgcctc ccgggttcaa    3480
gtgattctcc tgtctcagcc tcctgagtag ctgggattac aggcgctcgc caccacgcct    3540
ggctaatttt tgtattttta gtagagacag cgtttcaccg tgttggccgg gctggtctag    3600
cgctcctgat ctcaagtgac cttgggagat tcttgctcc taatattacc tcaagccttt    3660
ttaaacgttt taagccggag accaagcatg gatatgggag ttaggggtct tgatttaatt    3720
cttggttgct tcaaactctg tggaaccttg aggtgtttct tgccttctct gggtctcaat    3780
tttcacatct atatggtggg gagcttggat tgggtaatgt ctgaggctag aaccatggcc    3840
aactcgggtt ctgctggggc tgacttgccc tggccttccc tgaccaccct gcatctggct    3900
```

```
tctggagaag tccctcactg accttgttct cctccccagg ttgtgaaatg tgctcgcagg    3960
aggcttttca ggcacagagg agccagctgg tcgagctgct ggtctcaggg tccctggaag    4020
gcttcgagag tgtcctggac tggctgctgt cctgggaggt cctctcctgg gaggactacg    4080
agggcttcca cctcctgggc cagcctctct cccacttggc caggcgcctt ctggacaccg    4140
tctggaataa gggtacttgg gcctgtcaga agctcatcgc ggctgcccaa gaagcccagg    4200
ccgacagcca gtcccccaag ctgcatggct gctgggaccc ccactcgctc cacccagccc    4260
gagacctgca gagtcaccgg ccagccattg tcaggaggct ccacagccat gtggagaaca    4320
tgctggacct ggcatgggag cggggtttcg tcagccagta tgaatgtgat gaaatcaggt    4380
tgccgatctt cacaccgtcc cagagggtga ggcactcctg gtgtgcatca cagagttctc    4440
aggaaagggg tgcttagtca ccaagactga tttgtcctca tgaagtcagc ctgtggggta    4500
acttggtccg tgggatttcc cctaaaaagg tagccaggca ggtaaaattt gctcttgact    4560
cttggcagga aacatacaac tctttctttc ttcttttctt ttcttttttct cactctgtta    4620
ccctggctag aatgcagtgg cacaatcata gctcactgta gccttgaatt cctgcgctca    4680
agtgatcttc tggccttaga gtagctggga ctacggctgc tgtaccacca tgaacagcta    4740
atttttttt tttcttttag atgggggtg ttgctatgtt gcccaggctg gtctccagct    4800
cctggcttta agcaatcctc ccgccttggc ctcccaaact gttgggattg caggcatgag    4860
ccactttgcc tggccaacag aacacttctg ccgagaggaa gtgtgtggtg gccaggaact    4920
cagattctgg agccagaatg gtgcaggctc aaggtcaacc ctgtgtgatc tcaggcttcc    4980
ctatggagcc tctccagcct cagtctccct tgtttcagtt tcctcatcta caaaacaatg    5040
ttaatagtca aatggtgcct atcctataag gctcttggga ggattcagtg agttaatttg    5100
agtaatgctt aggatagtgt ctattaccac tggctgctat ttattatttc tgttatgagt    5160
gatactctgt acttgtacac ttttatttct gtctgtttta aattaacagc acaacagacc    5220
ataacactgc agtatattga atttatttta taattaacat agcatattat aaactaatat    5280
agcttaaatg tttatgtagg atttctgaca tgaaattgca ttagatcata gatgttcaga    5340
gttggtatat aacagcccct gagaatgtag taactcagca gagaccagaa ggtcagagaa    5400
atgaccactg agtattttg aaactctttt gttttcttcc aaatagtgat tcttagggct    5460
cctgagaggc agatggaaca atcattaaca ttccacttta taaatcggga agttgagacc    5520
aaggaaagta gtttgaataa gctcacagta gttaatgagg gggccagtgc tggaccaatt    5580
ggccagcact ggtcattgac ttattcatcc atcattcatt tattcagcca gaatctatta    5640
ggtgcttcat acatatttgc ttaaagtttg ttgtgttcat agagctttgc acacggtagg    5700
tactccataa acatttgttg atgaaataag tgagttactg aatgaatgat tgaattagaa    5760
tgacactgca gtgttaaaat gggctgggtt ggggaacatt ttagttttg tttttgtctg    5820
ttttccaaaa atgtatgtgt tgttcacatg agtctggata accctagatt gagattgatg    5880
acataaataa atttgtcttc aaggctgcac taaagctggc tcacatggct aggtatttac    5940
agagcagaag tggtgcagtc ctctctgatt agttgcacgt acagaagaca tattcgttat    6000
tggactgacc ttagtttctc ttataatttg ttaggggaat tgaatcagcc catctgagaa    6060
gttacaagat tgtgtcttgt catctttaaa agttcagcaa tgtgatgtgg tacagatggt    6120
ctgagggggtt tggagaaggt agcctagatc cctagggccc agagaagaca ggatgtgaac    6180
agaggaagta catggattgg tgaagaaaag aaatgggata actcatgggt caagaagaa    6240
atcatgatgg aaatcagaaa atattcagaa ccatacaata atgagaatat tatttatcaa    6300
```

```
aatctattgg atgcagctaa agcaggacat aggggggaaat ttacaacctt aggtgcctag    6360
attaggaaag aaggaaggca tttgtttatt tatttgttta tttatttatt tgagatgggg    6420
gtctcactgt gtcacccagg ctgctggagt gcagtagcac gatcataaat cactgaagtc    6480
tcgaacttct gggctgaagt gatcctcccg cctcagcctt ccaagtaggt gggacacagg    6540
ctagcaccac cataccaggc taatttttt tttgtagaca cagggtcttg ctatgttgag    6600
gtctcaaact cctgggctca agtaatcctc ctccctcggc ttcccaaagt gctgggatta    6660
caggcatgag ccactgcgcc catctaaggc tgaattttaa tgagctaaga attcatctta    6720
agaaagggct aaatagacag caaaagcaaa cattgaaggt tgggactgag ctgagtgggt    6780 agcaggatg ggagacaaca gatctgagga gagcaggaga ttttgaaagg attgcactgc    6840
ctgaggttta agcctttaga atccagctct ctctgagctc cctttgagct ctgacattct    6900
gtgactctga tttggtggcc ttcccttagt ggccttactg atttcatttg gatggtgctt    6960
gtggtatatc caaccaacat gtcttcccaa atggcctttt aatttcctat aaagaagtag    7020
ttgtcattga ttgcaggtta gggacagaaa atgctgtgga atgaaacaaa atgcaagtta    7080
aagaactaaa ttccaaaaat acccattgct actattgact gagtgaattc ctactgtgtg    7140
ccagacactg tacccagtcc attccctgta ttgttttatt taagcctcac aagggtatag    7200
tgtgactaca ctgtttctta acaatgaaga aactgcccaa atcgcccatc tgggaagcgg    7260
cccagctaga atttgaatcc aggcctgttt tcctccagag cttgtgctat tctctgtctg    7320
tcataaaatg tgggggcttt gtgtggtaaa cttgctcagt tgggcatagc agttgttagg    7380
aaacctgagg ctggtaacac cagctgtaat accagctgtc cgtctgactc atgcaactgt    7440
taaagttgat agggctgagg tgtcagactg agctctgaat tgcctgattc ctataacaat    7500
attaacttaa acattttta aattgggaaa tgcaccatgc atacagaaga gtgtgtatat    7560
ttcatatgta tagtgtaaac tgttcccatc acccaggtta aaaacagga tgttgccagt    7620 acctggggcc ttcttaact gcaactgcta gaggtaaaca ctggcttgac ttttgtgtaa    7680
atcatctctt tgccttctt taatgtttta gcatctttta aaataaatcc ccaaataatg    7740
tattgttcta ttttgaaaaa ctgagtagca agccaaaaat agctgtgtaa agaaaggtca    7800
cttaaattag ctgggtgca gtggctcaag ccttttaatcc cagtactttg ggaggctgag    7860
gcaggtggat cacaaggtca ggagatcgag accatcctgg ccaacatgga gaaacccgt    7920 ctctactaaa aatacaaaaa attagccaag aatagtggca tgtgcctgta gtcccagcta    7980
ctcgggaggc tgaggcagga gaatcgcttg aacccgggag gcagatgttg cagtgagctg    8040
agatcgcact gcttgaaccc gggaggcaga ggttgcagtg agccaagatc gcaccactgc    8100
actctagcct gggtcacaga gcaagactct gtctcaaaaa aaaaaaaaa aaaagaaag    8160 gttactattg ccttttctta gatgaaggtt cccaaggcag ggaaagctaa gtggagtctc    8220
agggacttgg tctggctttt ccttccctgg gaatttataa ggacctcttc tgggaagtca    8280
gtcggcaatg ccatgaatga gtctggggaa atattgggct cattgcaact ggagggtctg    8340
gtaggactga tgtgaattag gtgctgtgtc cggaggaaaa tggccagagg aagtgggctg    8400 cttttgtacag tcagtggtaa agttgccaaa ggctattata gctcacagga atgggccaag    8460
gctaaacact cctgtggagt gaaatgaatg tcctcagctg actgaggcag cgggagttga    8520
gaagaaacga tattagttca tggtgaagac aagtcaaata tagataaagg ttagggtcag    8580
gcttgcctgg acatctagga gataactgcc ctcaacttgt ttgaatcttg agtcactgct    8640
ccattttgtt tgaactggtg gccatctact tatagtatac agccatcaac ctgagatttc    8700
```

```
cctacatggt cttcctgcct tggtctcctg tatcctgaat cctatggcct cttcttccct    8760
ggtttactac attttgctag accgtatcct ccagtcaatt ccttagaatg aatgtatgaa    8820
agttaaaatt tctgaggtct cacatgtctt aaagttccct catactggat tgatagtttg    8880
gctgggtata aaattctggg ctggccatca ttttccttca gaattttgat tgcattattc    8940
cattatcctc tcttttcaat attgcttcta agaattccaa aaccttttt ttttttttctt    9000
tttgagacag tgtctcactc tgtcacccag gctggaatgc agtagtgtga tctcagctca    9060
ctgcaacctc cacctcctgg gtttaagcga ttcttcttcc tcagcctcct gagcagctgg    9120
gattacaggc acccaccacc acacccttta gtagagatgg ggttttgcta tgttggccag    9180
gctggtcttg aacttctgac tttaggtgat ctgcctactt cggcctccca aagtgctggg    9240
attaaaggcg tgagccacca cacccagcct ccaaaaccat tttaaaactc tttctggaag    9300
cttttaaaat tttcttttag tccccagaat tttaaaattt caattatgtg ccttggtgtt    9360
cttccattat attagtcacc caagaggtac tttcaatctg gaaacttctc tatgttttgg    9420
gaaatgttct tgattagttt acaggtgatt tcttcctctc cattttatct cttctctttt    9480
catgaaacta ctattaattc aatgttagaa ttccttgact gatcatttaa ttttcttcta    9540
ttttccatct ctgtgtcttt ttgctctact tttctatgat agtcacagct ctatctttaa    9600
actcttgagt ttttcattt tgatgtcatg attttaattt gcaagaggta ggtttgactg    9660
attctttttt gtagtatctt actcttgttt tatggatgca acatcttctt tgacttaagg    9720
atcataagat aggtgggttc tttgtttgtt tgtttgactg ttttttcaccc tatgtaaact    9780
ttttctacaa gtttctttcc ccttcccccc tttttggctt ctatctccca cattagatgc    9840
tttctctggg ctcatgatac tctttggttt tcttttctcaa gattgacagg taggactta    9900
aaacttgttg agcatgcggg tgaaacttgt ctaccatgaa tttcactgta gatattttgg    9960
agattgacag tgtttatatc tttagatctc acctcctggg ttgatcaagt tatctgagta   10020
caccacagac cttttgcctg gggataaacc agaaatctgt ttcagaaacc actttgattc   10080
agtcttcctt gttttagtca tttccttcag ttccggaggt ccgtcatgct gatcattcca   10140
gagccctta cagatcctag ggtacacact gcatggtttt caactttctt gttttgggt   10200
taagatttgg ctttcaggag tctcctcagt ccgttactat tcattcaatc agcaagtcct   10260
tgagcacctg atttgtgcca gacattcttc taggtgttag ggatacctca gtgaacaaaa   10320
cagacaaaaa tctttgtctt ggaaatacac acactccagt caggggagag ggacaataag   10380
ccaaaggaag gaaattacag cgtgtgctag aaggtgataa gtgctgtaga aagtaagtaa   10440
agtgggtttg ggagttgaga gtttgggaag gggataaatg atggcaattg taaatagagt   10500
agtcagagtt ctcacttaga aggtgaaatt caagtaaaga cttgaaggag gacagggaat   10560
tagccacatg gatggctagg ggaaggcttc caagctgaga ggacagccag agccaaggcc   10620
cagaggcagg agcatacctg gtagttttag gaaacaggag gccaggatgc tgagtggagt   10680
aagaggggc atgaaggag aaacttgggt ccacgtggtt ctagacaggt attttgtct   10740
gttttgggcc ctgaaggtta ctattggact tggactctta ctctgaggaa ataggacgc   10800
tattgggacg tttgtacagg agcaatgtga cctgagtttt gtttgtaaag gattagactc   10860
tggctgtggc attaaggcta ggctgtgggg gcaggaacag aagcagggg accagttttg   10920
cagcctgtgc agcttccag ataagcaggg attgtggctt ggaggaggat ggtatagagg   10980
aggtgacaag aaatgactct atgtctggta tgtagatatt ggccacagat ggcatttgag   11040
cactagagac ctggctggtc cacatggagt ttccataagc acataataca catcagattt   11100
```

```
caaagactta atatgaaaaa aaaaatttaa cgggccccgg gaattttttt cttttttttt    11160 tttttttgaga cccagtcttg ctctgtcacc caggctggag tgcagtggtg tgatctcggc   11220
tcactgcaac ctccgcctcc caggttcaag tgattctcct gcctcagcct cctgagtacc    11280
tgggactaca ggcacctgcc accacgcctg gctaattttt tgtattttta gtagtgatgg    11340
ggtttcacca tgttgtccag gctggtctgg aactccggac cttaggggat ctacccgcct    11400
tggcctccca aattgctggg attacaggca tgagccacca tgctcagcca tatcttgcta    11460
ttttctacat ggattacatg ttgaaatggt aatgttttgg ctattgtgga ttaaatagaa    11520
tatatgatta aagttgattt catctatttc ttttaacttt aaaaaatatg tctgttagag    11580
gatttgaaat tccacatgcg gcttgcattt gtgacctgca tttcatttct gtggaacagt    11640
gccctttttg ggacatgctt tgaaggtgga gtcaacagga tttggcagat tacagacgag    11700
aggcttcaag ggtgactcca agacttcggg gcagagcacc tggaagaaag gggttaatat    11760
tagccaagat gaggaaggct gtcggtttgg caggtgcatg ggcaggttag gagtttagtt    11820
ttgaatatgt tggaggtgtt tatgaaactt ttaagtggag atggaaaata ggcagttgga    11880
tgtgcaagtc cagggttcag ggagacagtt caggctggag atgaagatgt gggagtctga    11940
ggagagattg tattcaaata ttcaatccat gagacttgat gaaatcactt ctcttccaaa    12000
tgatttacag cctgcagaat cattttccct atctttgtag gttatgtct tcattttgtt    12060 tcatttattt ttcagttatt cactgttttta gtgagttttg agtaggagcc agattggatg    12120
catgcgttca attcaccatc caacactgta ttaactactt gaaactcatg tggttgttcg    12180
gttgtttttt tgaccttttta ttctggatgg aagagagatg cttatgaagt tgcagtaatc   12240
agtaagcctt cccacattgc tccatcagcc ttcctggaag aataatgtct tctgcctttc    12300
ctgtaggcaa gaaggctgct tgatcttgcc acggtgaaag cgaatggatt ggctgccttc    12360
cttctacaac atgttcagga attaccagtc ccattggccc tgcctttgga aggtaggtgt    12420
atgttctcag ttaatcagaa agggaagggc agtcagtgca gatccatggt taagagcaga    12480
acacacctcg gttaacatcc catatgctgg cagtatagcc tccctatgac tcaatttcct    12540
tgttttaagg ctagcaccac cccgtctcat tgggattttg ggagcattaa aaggacaaaa    12600
gcgtgtaatg ttagctatta gctttcatta tctcccacac agtatactga caattgggct    12660
accatatatt gagggctaac taaggtgtt acttaccatc caaactctca ttatctgtac     12720
cgaaaagata tggacacatg ttttgagtta gggctggtat ctcttgatct ctgaaattta    12780
gcagctcaca atgggaaact caagaaccaa gtggatctag agactctggt atccctcagt    12840
gcccagggtc accacccaaa ctcaggaaca ggaggggctt ggaccgcacc acttgaacat    12900
accaggcatc ctgccaggtg ctttatggac aatgtctacc ctttgcaaca accctgagaa    12960
gtaggtggtg ttttttttcca ccttatagat gtggaaactg gcagggagg ttaagtgacg    13020 agggaggga agatgggtct gattgtaaat tgtccccacc tacactttct cttttcttgg     13080
gagaagaaat gtcagttgta aagagagagt gcaagcctgg cactctttag ggcttgttcc    13140
tacaccactg tagggaaagc tcattggcac tgaagccccc tgagctgtgt gtggtgctgg    13200
cagatgggtc tatcaccctg gactgtgtcc tctgggcagc aagcaagcct gtgggcgggg    13260
tggctggaag tctgtgcctg gcactcgcga gtgcaccgtc tcattgaaga acaggatcta    13320
aacatcagtg cgccacagca gggtgcgcgg cacggagtgc aggccctggt ttggcccttg    13380
gttgaggttt gctgttgaca tcatcaagca cagctagtca ctgtaagacc aggccagggt    13440
gcaagattcc ccacacttct aaaggtgaca attggtgtat ttatttctct ataaaatgac    13500
```

```
attttttttt tctggagaat tttagtatca ttggtgatga ctggaaaacc tgcatcagaa    13560
atcaggtcgg aagaggaaga tatatatctg atatgtactg gagaggaaga tatctatctt    13620
atggtctaag ttcagggatc ctggtatatt cagagggcag aaagctcagc aataatcatc    13680
aactctggga acagaggtga cataaacaca gggcgtcccc tttgtgtgac tgcagatagt    13740
catcagtgag ctcagagctc tatgaaaatt acttgctagt ttttgggttg aaaatagtgg    13800
gccagtgttt ggttggggc agtgaggctg tgatggcggg ggaccatgcc aagctcctac    13860
cagcctggga cgctaaacca gcacttcccc atttcctgaa aggggaacta aactctgaca    13920
caggaaatgg tttgcttgca ttactttcag gatgagaaag aagagcact ggccttccaa    13980 acacacccg tgcatgaaaa ctctccctgc atggggtgca tggggaggat ggggaagtgg    14040
aggcaggatc acagactctt gttcgagtgc tcagctgggg caccccggtg accccgaggc    14100
cttcccttgc taggtccacc cagatcaatc aggatcatct ccccatctcg aagtttaact    14160
ttatcacatc tcagagttcc ttttgccacg taaggtaaca tattcacagg ttctgagaat    14220
ccggacatgg acatctttga gggtctattg ttgtgcctac tatatccatg aataataatg    14280
ataataagca ccatttttg agagtttgcc atgtcagata ttcttttaaa ctgtatttta    14340
tctcgctgcc tcctgaaaaa atccttccag gtgtatattg tccccatttt tacagatgag    14400
agaactgagg cccagaaagg ctaaatggct tgcccaagtg tatggtggac ccaggttttc    14460
aaactcaggt gtgtctggct tcagagactg ggctcctgag cccttaagcc ctttgttccc    14520
ctttagaaaa agtcacctga ggctgagtgg tgaagggatt tatccaaagc cacccggcca    14580
ctatggcagg acagatatca gaatacaggt cttccgatcc cagcccagag cccttcccg    14640 tcatctagaa ctcctcctgg tgtcagtaat gataacggca gtcactgatg tcttttgagc    14700
acttactttg tgttgagcac ttacactgtg ctaagcactt gacataggtc atcttagttg    14760
atccgtgtaa aactctgtga ggtagtgacc aacatttctc ccaccttaca gaggtggaaa    14820
ctgagggtta ggaagtttcc ttgactgtcc tcaaagtgca cagcttgtga atggaggagc    14880
caggatgggc gcccgctggc tctcctatcc cttcagttat gtcagcgtcc cccgcagcag    14940
cccattgtct ggttaggtcc cgtcttcacc atggtgccac cttcatctgc ctcttcttct    15000
gccttccagc tgccacatgc aagaagtata tggccaagct gaggaccacg gtgtctgctc    15060
agtctcgctt cctcagtacc tatgatggag cagagacgct ctgcctggag gacatataca    15120
cagagaatgt cctggaggtc tgggcagatg tgggcatggc tggatccccg cagaagagcc    15180
cagccaccct gggcctggag gagctcttca gcacccctgg ccacctcaat gacgatgcgg    15240
acactgtgct ggtggtgggt gaggcgggca gtggcaagag cacgctcctg cagcggctgc    15300
acttgctgtg ggctgcaggg caagacttcc aggaatttct ctttgtcttc ccattcagct    15360
gccggcagct gcagtgcatg gccaaaccac tctctgtgcg gactctactc tttgagcact    15420
gctgttggcc tgatgttggt caagaagaca tcttccagtt actccttgac cacccctgacc   15480 gtgtcctgtt aaccttttgat ggctttgacg agttcaagtt caggttcacg gatcgtgaac    15540
gccactgctc cccgaccgac cccacctctg tccagaccct gctcttcaac cttctgcagg    15600
gcaacctgct gaagaatgcc cgcaaggtgg tgaccagccg tccggccgct gtgtcggcgt    15660
tcctcaggaa gtacatccgc accgagttca acctcaaggg cttctctgaa cagggcatcg    15720
agctgtacct gaggaagcgt catcatgagc ccggggtggc ggaccgcctc atccgcctgc    15780
tccaagagac ctcagccctg cacggttttgt gccacctgcc tgtcttctca tggatggtgt    15840
ccaaatgcca ccaggaactg ttgctgcagg agggggggtc cccaaagacc actacagata    15900
```

```
tgtacctgct gattctgcag cattttctgc tgcatgccac ccccccagac tcagcttccc    15960
aaggtctggg acccagtctt cttcggggcc gcctccccac cctcctgcac ctgggcagac    16020
tggctctgtg gggcctgggc atgtgctgct acgtgttctc agcccagcag ctccaggcag    16080
cacaggtcag ccctgatgac atttctcttg gcttcctggt gcgtgccaaa ggtgtcgtgc    16140
cagggagtac ggcgccsctg gaattccttc acatcacttt ccagtgcttc tttgccgcgt    16200
tctacctggc actcagtgct gatgtgccac cagctttgct cagacacctc ttcaattgtg    16260
gcaggccagg caactcacca atggccaggc tcctgcccac gatgtgcatc caggcctcgg    16320
agggaaagga cagcagcgtg gcagctttgc tgcagaaggc cgagccgcac aaccttcaga    16380
tcacagcagc cttcctggca gggctgttgt cccgggagca ctggggcctg ctggctgagt    16440
gccagacatc tgagaaggcc ctgctccggc gccaggcctg tgcccgctgg tgtctggccc    16500
gcagcctccg caagcacttc cactccatcc cgccagctgc accgggtgag gccaagagcg    16560
tgcatgccat gcccgggttc atctggctca tccggagcct gtacgagatg caggaggagc    16620
ggctggctcg gaaggctgca cgtggcctga atgttgggca cctcaagttg acattttgca    16680
gtgtgggccc cactgagtgt gctgccctgg cctttgtgct gcagcacctt cggcggcccg    16740
tggccctgca gctggactac aactctgtgg gtgacattgg cgtggagcag ctgctgcctt    16800
gccttggtgt ctgcaaggct ctgtagtgag tgttactggg cattgctgtt caggtatggg    16860
ggagcaccat caaggctaag tgtgggagca ccgagctggg ctctagaagt ctgggcccag    16920
cttcgcctct gccaccctgc tttgcaacac tgcccagatc ccttccsttc tgggccttaa    16980
tttcaatatg tgatgatgac agccacactt tattgactgg cctatgtgct gggtctggtg    17040
ctatgctttc cggaatgacc tcatctaatc tctacaacca ccctgggggg taggcaggaa    17100
tgttattatc tccattatcc ttgacttgag gctcagagaa gtgaagtaac ttgtccagga    17160
aatggcagag ctggggttca caaattgcat cattctgatt acaggttttc tgcctcccac    17220
cagtctatgg atacacttca gaggctccct gaaaaccttg aggtcacttg cagaaagttt    17280
tgtgtagtat gtgtccgtat caggaacaac accaaatcag aggtgacttg tgccccatca    17340
gagactttaa caccccaacc agatgggaat ttcaggaccc aagaaataga agtggctgc    17400 agggttacaa ctactgttgg attcctgagg tagcacagtg tccaaacagg atttcagcac    17460
tacccgtatt gcttagagcc ccagccaaag atgtgaggtt ttgcccttttg gagaatctgt    17520 gccctgaac tcgggggcct ctttccacat cttgggggca ggcaagggca gagggtgtgc    17580
ctaggcctgc ggatcagcat gcgacagatt ccccaacatc cttccagctt gaaagggat    17640 tgccctgctt ctatttagaa cctataggaa agcagaagtt ctagattgaa gttaaaattg    17700
attcccagcc tccagggct ttgggctaca cctggatgac cttaattgac cctaagcatg    17760
ggacaaacca cttcctgaga gtattaggat ggtatacatc ttctctgggg gcaaagcaac    17820
aagatttatt tttcatcatg gaccaaacac atggatatccc actagaaact gtgtagtgaa    17880
ttttgttaac cctgacatag gaccatggt ctttaggtta aagcataata acaacataat    17940
acataacata tatagcgaat atatatatgt attatatgca atgaatgtaa atatgattat    18000
acccatcatg gtcttggagg aaacagatga cacacttaaa atgggtgttt tgaggagagt    18060
ttgaaaaaca gattgtttac aagcatgggg caggagttag gaagagtgag agggttggtg    18120
caggggcctg gggttagtaa cagctggggg agggtagact tgaagggggga aggggaggga    18180 gactaattag ctggggggaa ggtatggaga cggctgcctg agcttctgca aagtggaaga    18240
atactgcttg gccctaactc ctcacccca ctcttgctcg tggccagcgc cttccaccag    18300
```

```
ctggacccat cagggaggcc gagtgggctg tctgctggag tagtccccag gcatcagcct   18360
cccaggagcc agggacgggt agagaagggg gagagtggat ctggccaggc aaatggaaaa   18420
cagccagcac caaactctat ttccctagga gggaggatca tgatactttg agtgggaatt   18480
tggaaacctg tctgttggag caatttccct gatagaaata agaatgtgca ttttcctggg   18540
tagtagactc agttttacc ccaagaggcc aggcatcact ggcctgtgtg atcctcatag   18600
gccagtccat ctctggaatt cttgaatgga tcatccatcc ttgattaggg atgtcccgt    18660 gattaccagg gtgtgcagaa gggctctggg aaacctgtgg gtctgtctct gtgttcagag   18720
aaaggtgagg gtggcctggt tctagctcat ggtgctcaga ctgtggtgtg taaaggcact   18780
cgtggcaatg cagattcctg ggcctgcctc tagtgattcc cattcagtag gtttggggtg   18840
gggcccagga aatctatatt tttcacagac accctggtg attctgatac aagtggtctc    18900
gccctgggag aactactggt ctgcagcaac cagcttggtt ttccattagc aattactgtc   18960
cttgagcgag ttttactgct cttcaccta cacacactaa aactgccaag gccgtagggg    19020 agggaagca accatgaggt tgctgtgagt gcactgtgtg tgtgtgtgtg tgtgtgtgtg    19080
tgtgtgtgtg tgtatgagag agagagagag attgagaaag agaggaaggg aggaaggggg   19140
agggcacagg ctcctctccc acagtgccaa cctgcctctc tcccacttga agcgtttcca   19200
tgccaactga aatcctcagc ctctaggaaa ccctatatac acagtgcccc tatataggtt   19260
tctttagact ctggctctct cagactctag agtgatggct ttaaaagttt tatgttaccc   19320
acagagagag agcacgcacc accatgtaaa catggaacct aagtttcaca aaatgacttc   19380
gctttatgaa ctctgagaca ctctgctctc ttctgttctg ttctatttcc atttagaaa    19440 tgctgctcag gaccttcaaa atgatttgca tgacctgcaa cctgcagtct gaaaaatcac   19500
tgcactacag aagtggccat aagaggccct gagggagaag ctgcacaatg tcatggttaa   19560 gagtgggtt tggagccaag ccgcctaggc tcaaagcctt tatgtgccgt acaaccttgg    19620
caaagtcact tcgcttgtct gtgcctcagt ttctttctca cgaatgctca taataatggt   19680
tcccatttca ctggcttgtt gtgaggatga aatagtgtta ttattgagaa gtggtaaggg   19740
tagtgatcag tgctagcgat catgattcta ggtgacttt actgtgtacc gggtgctcac    19800
aaggctttat gtgcacagcc tggtgaggct gataatacta ttgttccctc ttttttttt    19860 ttggaaacgg agtctcgttc tgttgcccag gctgggggta cagtggcaca atctcggctc   19920
atgcaatctc tgcctcccgg gttcacgcca ttctcctgcc tcagcctccc aagtagctgg   19980
gactacaggc gcctgccacc acgcccggct aattttttttg tattttttggt agcgacaggg   20040 tttcactgtg ttaaccagga tggtctcgat ctcctgacct cgtgatccgc ccgcctcggc   20100
ctcccaaagt gctgggatta caggcgtgag ccaccgtgcc cggcctgttc cctcttttat   20160
agatgaagag accagcaaat aactagtaag tcgctgatca ggatcacaat atccagctga   20220
ggcactccag agcctgagct gttaaccatt cagtcagggc ctcccaagtt tgcctaaaga   20280
taaagaatca tgtgcacagt tgttaaaata tacagattcc tgggcccac cccgcagata    20340 cttgattgcc agctccaggg tatgggcctg agaatctgtc ttttagggaa gctttcagat   20400
gatgttgtga tcaggtgagt tttgggaatg gtgccccaag aggagtggca gacagggctt   20460
gctcggcagg gactagcctg ttggagtggt gccattgggg ttaaggactg ggcagcaggg   20520
cctcactaac cacagcctat atgcctgttt ctgaagtttt ggccactctc atccagctgg   20580
tctactgtct gctgacctag atgatggtaa attgtcccca ggggtagcct gtctagttca   20640
ggctgcacct ttcgcatata tcagctcctt tccaccatca tcccctttgt gaggctgctg   20700
```

```
tgattatcat gttccttttg cagagatgga aacattgcct caaattagct ctgtcatttc   20760
ctaaggattc cagggttctt tagtaggggg tctggatcct acgtcctggg ccatcccat    20820
catagtgcac cacgtcacct ccctggccag ggaccgtggg gtctccactt ttttggggtg   20880
ctccatctat gcagggtttc ctggaagcac agatgctggc acttcaggga tgaatgaaag   20940
tcttttgggg ggatttgtag attttttct tgtcttacta gctccatttt caaatgtatt    21000
tattttgtct ctttagtttg cgcgataaca atatctcaga ccgaggcatc tgcaagctca   21060
ttgaatgtgc tcttcactgc gagcaattgc agaagttagc gtaagtcagc ctgggctgtg   21120
gacaatgggc tccaagtgcc ctggtctcac cccaggtcgt gcagcctggg aagctgtgag   21180
tgatgggctg gggcagggc  tgtttgcatg atgggggtg caggtgattc ctgcccagag    21240
gggaagggca accctgggat ttggtgctca ctgtccaatg tgctttgctt ctgtgtctcc   21300
tctcttctgg aactgaacag tctattcaac aacaaattga ctgacggctg tgcacactcc   21360
atggctaagc tccttgcatg caggcagaac ttcttggcat tgaggtgagc ccaggttttc   21420
cttattccct ggaaactatt ttttgccccca ttcctgagtc agtctgatct ggtcttggcc   21480
tggcactgcc cacactggct cctgacctcc tgattgaatg cagggacagt gtctcatttt   21540
aagcaggggt tctctaatgc tgtgatctcc ccagtaaact ctggactagc tctgctgagg   21600
acttcctgtc ttttgacctt tagcccgtag ggcaagaaag cttttctagg ccccttcct    21660
tttctgtgtc taagagtgtc acagcttttct ggggttactg agttccacga tgcatgttga   21720
gctcgtcctg gtggggagg catacacagt tacttgccac cccagctgtg gcagcgagtt    21780
gctgcaacac tcccaggagg tcctttcacc actcagagca tgcaaggttt gcagtccatc   21840
tggttctgca tttctgctac tccagtgtct cccagtttca acaggagtct ctctctctcc   21900
tacctgatgc ctttaaattg cccctctagc tggccgctgg gttggcctgg cttctctctc   21960
cttctctctc tctcagatat tcttgcctcc tgtgatttgt gaggcagtaa aaaaagacaa   22020
agtaaagaat tgcttccatc tattcttttta cctcttgggc tgggtttgtg gatgggagcc    22080
gccatttaa  aatggcgggc cacatagctc agtctcggca agggctactg agatcagaac    22140
cacaggtgcc aatttgtaca aaggactcag tcctgctacc actgcctgat ccctcagact   22200
cacaagcctg gaataggctg tggccagacc tggctggccc atccctgaga agggtgctag   22260
tttcagaaat ggaggctgag tttgtggcca acacagtagt cctccggtat gtgcaggaga   22320
gatgttctaa gaccccagtg gatgcctgaa accatggaga gtatcaagcc ctacacatac   22380
catgcttttc ccaataccta cacacctgca ataaagtgta gtttataaat taggctcagt   22440
aagagagtaa tagcaactca taataaaata gaacaattat aacaatcaat atactataat   22500
aacactatgt gaatgtggac tctctccatc tccctcaaaa tatcttcttg tactgtactc   22560
accccttcttc ttgggaagat gtgtggtggt aaaatgcctg tgtgatggga ggaagtgagg   22620
tggatgacgc atgcagcact gtgctctagc gctgggctgc tgttgacctg accacacttc   22680
agaaggagaa tcatctgctc ccagagatcc ctaatctttg agcaacaatg aggtcggcag   22740
ctggatgtca ggagcagacg atcttgatga ttaccaaatg ggagcgtata gagcgtggat   22800
gcgctggacg gggggctgat tcacgtcctg ggtgggatgg agctggatgg cacgtgatca   22860
gaatagcatg caatttaaaa tgtatgaatt gtttatctct agaattttcc atttaatatt   22920
tttggactgc agttgatttc agataactga aaccatagaa ggcgaagctg cggataagca   22980
gggggcaggg attaccgtat atcattgtaa tagagagcac aggctctgga gccagactgc   23040
ccgaggtttg aaccctcatt agctgcgtga cctcaggtca gcccaatgtc tgtgtgcctc   23100
```

```
cgtttccect  tctgtagaat  ggaggtaata  accctggcta  cctcacaggc  tgtagtgatg   23160
agcaagcaag  ttaatccaca  tgaagggctg  caccgtctgg  caggggcttt  atatagtaag   23220
cgagtggctg  aaagatgatg  ggtaaatcac  acaagcactc  agcttgtttc  tccttatgtg   23280
agtccggtcc  tccaagcagg  gattcaatgt  gccacccatt  tattgggaaa  agtcctaaa   23340 aggggaagtg  gggaagggag  ctggggaggg  ctgggaggtg  tgtccctgag  tgaaggagag   23400
agggaaggaa  ggaaggttga  gactgggcac  cttggacttc  agtgcagtcc  taagacatct   23460
tggcaaggct  gatgaggagt  tcttgaacca  aattcaccag  gcaggggagc  ctgatgtctc   23520 aggcagggc  tggcaagtgc  agatgcgagg  atgttagatt  ttggagcaca  gcagctgggg   23580
cccttggcta  cctccaagga  gctgaggctg  gagacctgaa  aggcgagttc  tcctagctgc   23640 cacaccectt  ctccaaggat  acaataatat  ctgccttata  ggattgttgt  gagctgagtg   23700
gcttgacgtt  ccttgaaaga  atgaaagcgt  atagttatcc  caggaagcct  agggttgcag   23760
gtgagagctc  tggggcttct  ccgaagctct  ccgaggtgtc  tggattcagt  tgcagcagga   23820
gccttccttg  ctgggatctt  ccccaccec  tagccttggc  cctccctctc  tccttccttt   23880
ctggaaggct  cagtgggccc  cacccctccc  tccagccacc  tggacctgcc  cagcgctctt   23940
gtgcaacagg  taaagcctac  ctgtagcaac  aacagatctg  ggaaggctgc  agagggcacg   24000
atggggtctg  gatcgagggc  ggctgagacc  agagggaaag  gtgtgaccct  gagtcaccct   24060
cgctgtcccg  gggaaaccac  ctcccaggac  agctgcctac  tgtggctcct  gcctggaatt   24120
gtcacactgc  tgtgcaaaca  gcgtcccgct  gccccttttcc  ctttgctggg  ggaaaatgaa   24180
gttgtgggag  ccgctgagta  aactagacct  agcagcgagg  gcacctgatg  tggctgctgc   24240
ctcccgggca  ggtcttcaat  gctttcttcc  tgtgtttccc  tggccagggc  acagacggcc   24300 ctcctttct  gcctgccgct  gtgttctctc  agcctcctct  gtcttccctt  ccaggctggg   24360
gaataactac  atcactgccg  cgggagccca  agtgctggcc  gaggggctcc  gaggcaacac   24420
ctccttgcag  ttcctggggt  aggttggatt  ccaggaagag  ggacctgcat  ggagggctt   24480 gggactttg  aggatttagg  ggcaggtgaa  actcttcagc  caggaggccc  cagaggcagc   24540
ccagctccag  tggggaggac  aagccaggga  gagagtgggc  ggcccttgac  tgccaccttc   24600
atacttggtc  tatgcctgac  aaacaggaag  tttgggatgt  tggggctagg  ggaggacagt   24660
gcccacgagc  tggtgacagg  aagccctctg  atcctcaggg  ggcgctaggg  ctgtacttta   24720
gctgcatatt  aaaaccacct  ggaagcttct  aaacactatt  gccaggcctc  ccaccccaga   24780
ctgatgaaat  gcaaatatct  aggtgcaagg  cccaggtatc  aggagtttta  aaaagcttcc   24840
caggggatgt  acagccaggg  gtgaggaccc  ctgacctaag  aaagagaagg  aaatggggaa   24900
ggataggaag  gcacccagga  taagaggggc  tgtgctaggt  ccctcggagc  tcttgctccc   24960
tgtaggacca  tgctagggcc  tgccaggag  gggagtaccc  caacctgcag  ccccagggtg   25020
ggcttcctct  gtttgctagg  cacccaggct  tgcacctgtg  ctgtttccag  cagcctctct   25080
cctatcctgt  catgcectag  tgtgaactgg  agtccatttg  acaagaactg  ggagttttag   25140
aacctgggac  tgtaggaaga  gagaataacc  ttagggccta  ggtgttccag  cccatttcac   25200
agggaggcaa  gttgccccca  agctcagttt  tttgttttgt  tttgttttgt  ttgagatgta   25260
gtctcactct  gttgcccagg  ctagagtgca  gtggcacgat  cttggctcac  tgcaacctcc   25320
gcctccttgg  ttcaagcgat  tcacctgcct  cagcttctca  agtagctggg  attataggca   25380
cccaccacca  cgcccagcta  attttttgtat  ttttagtaga  gacagggttt  caccatgttg   25440
gcccggctgg  tcttgaactc  ctgatctcag  atgatccgcc  cgcctcggcc  tcccaaagtg   25500
```

```
ctgggattac aggtgtgagc caccgcaccc ggcccccaag ctcagtttga gccacaaatg   25560
ggactatgtt gctctagaaa tcaacatctt ttccacactg cattagtagc aacagagtct   25620
agaacaaagg aggccacagc cccactgaac tctcttctgc ttgaggtcac atctgccaca   25680 tcagggtat ttacctcttt caacacatat ttattagggc acctgtctgg gccaggcgtt    25740
gtgctaaaac ccccaaacgc tgtcatatga tacaaagtgt tctgtaactt gcttggtttt   25800
tttttttgtt tgtttgtttg ttttgttttg ttttgttgt tgtttttttt tgcttcgcca    25860
tatattatag gaatttttt aggtcattat gacctcttta tttacttaat tatctatttaa   25920 tttattttac taatatttac agaaagggtc tcactctgtc acccaggctg gagtgcagtg   25980
gttgcaatca tagctcattg tagccttgaa ctcctgagct caagtgatct tcctacctcg   26040
gcctcctgag tagctgggac tacaggcaca agccaccatg cctggccgat atttttatgt   26100
tttgtagaga cggggtctca ctatgttgcc caggctggtc tcaaactcct gggctcaggt   26160
gatcctccct cctttgcctc ccaaagtatt gggattacac aagtgagcca ccttgctcag   26220
cctgacctca ttttcaaag agctgcagag tgttacataa tgtatttaac tggtcacttt    26280
ttgatgacta ttaagttgtt ttcaggtttt ttgttattac agtgtcatat ccctggggca   26340
cagagcagtg ctggcacata gccagagctc aatcgataca tacctaatga atgaaagtac   26400
agtggacatc ctaattcagc cattctttgc taacttgtgt acatacctgt ccagggtagg   26460
tccctagaat acagtcaata agtcagaagg tgtgagttgg gatctaccct ttggaaaggg   26520
atgttttcaa actacagtga gtcagaggag gatggcccag aagctgggg agttgaagct    26580 gatggcgtga aggaattagg ggtgttagga agaagcagga gataaagagc tagcttgcag   26640
aagaagtgtt agacttgtta tgggcaggta ctggagggta gctaaggact gtgggtggc    26700 agttaccagg aagcgtatct gaactaagtg tcagaaaaag tgtcacaact gtaaattact   26760
cttgtcagtg agttcctgtc cttaagggtt agggctgggt agccctctac tattctctaa   26820
gtctgtaatg taaagccact gaaaactctt gggttaagtt tggccatccc acccaaaaga   26880
tggaggcagg tccactttgc tgggaccagg agccccagtg aggccactct gggattgagt   26940
ggtcctgccc ctctggctgg gactgcagag ggaggaggac tgttagttca tgtctagaac   27000
acatatcagg tactcactga cactgtctgt tgactctttt ggccttttca gattctgggg   27060
caacagagtg ggtgacgagg gggcccaggc cctggctgaa gccttgggtg atcaccagag   27120
cttgaggtgg ctcaggtaag cttcagagtc tatcctgcag ttttcttggg gagatcaggt   27180
gaagagggag gagctggggc cagttctgaa ggtctttgaa ctttatttct accccacaat   27240
gttaggcaat ggagtaagga aaaaagacca ttggatttca agagaggaca cttgagtctt   27300
tctgggtgac ttggaaatgt cccttgtcct ctcagggttt tgatacagta tctgtaaatt   27360
gaagatattg ggctggatca ggtacatttt atcttaaggg ccaattccaa tccattggta   27420
gtgggtgccc agtgcaccac attaaaaaga attctaaggc tgcacctggg cttaagaag    27480 agcactataa tcaattagtg atgtctaaaa aagctaaaaa aaaaaaaaa gagcactgca    27540 ttcaattagt gatgtctaaa aagggtagaa aaaaaaaaaa aaagaaaaaa gaaagagcac   27600
cgcaatcaat tagtgatgtc tgaaatggag cagaccagga gagcaccacg aattttgccc   27660
tccataggtt agctcatctc tgaggtcttt ccctgctctg atactttt gttccatgat     27720 tacctccagc ctggtgggga acaacattgg cagtgtgggt gcccaagcct tggcactgat   27780
gctggcaaaa aacgtcatgc tagaagaact ctggtgagtt tgggggattc tctgctctgg   27840
ggaagtggat cacaatctct gttgatcccc tggcctcatc cataggagcg gttgtgtgga   27900
```

```
cagacaaagg tggatgattg agtgattgac tgattgattg attgtgtttg tctttatatg   27960
tactgagtgg tatgaagctt atagagcctg gtatgtacat gctaattttt ttatttaata   28020
aaatatatgg gtttgctggt ttggtgactg cctccacatg gcataagtgt taagagcaca   28080
gactctgtaa tcaagcaggc cgtgatctta ggcaagttaa ataacaattt cagaatctca   28140
agtttcatgt ctgtaaaatg agggtaagaa tacttccaac cataaaggat ttttgcaaga   28200
attagataaa gtagtgcctg tgaagacctt aatatagtgc ctggcatatt tgtaagtgct   28260
ccataaatgt taaattagaa taatggcagg gttactacta ctattactgc tgctgctgct   28320
gctgctgctg ctacaactac tatagtactg tgactactac tactaataaa gttttgttat   28380
tttaaagtga ttttgagttc ctaggagcac tgggtattca agtcttaggt cattttggaa   28440
ggtgtaatgg agttttgata gttgaaagag gaaccatgaa tcatgcttat actgttgacc   28500
tgaagcagat tctaagtttc tcatccttta gatgccacta gtatagtttt ctgacatgtt   28560
ctgggcagct tcagattatg tcaggagat aaaatactga atgtttgatt ttcccgggaa   28620
gcagaaaggc actgcaacat atgggcattg ccataaacag attttatgga tggaccttgg   28680
ctgttgcagg gcttactagc tctactcaag tatgattgat tctatcctga ctggattttg   28740
ccacttggaa tttcttagta gaggagaacc ttgttatgag agcatcagtt atgattactg   28800
ttaaaagaaa aactttaggc aaattaaatt tagcagaact ggtttgaaca tacagcaatt   28860
tatgaattgg gcagcattca gaactgggag tgctccaccc agcaaggtag gcaagcagta   28920
tctatagaca ggaaaaggaa gtgatgtaca aaacagcttg attggttgca gctgggcatt   28980
tgccttatat gggcatggtg tgatgaggca ttttctttat atggatatag actgatcagc   29040
tggtagactg tgactgactg aagcctggct gctgtgattg gctaagactt agctgtttgt   29100
tataaggata tgttgttagg ttgcagtttg ctacatagga actcaaagta cagaggcagt   29160
ctcaggccaa atttagttta actatatgtt aagctgcagg tgacagaata cctccatcta   29220
tagaggttta aacaaggaaa gggtttattt tttcctgtat aggcagctgg atgtaggcag   29280
tgtagggttt gtacagtggc tacaagaggc caggaggggg ctcagctctg tctcattctc   29340
ttcctgttcc atcatcctta gcctgtaact tcattcacat ggttggttgt ctcatgatca   29400
caggatggct gctccaggtg cagcactact tctgtattcc cggattcgat ctatataccc   29460
aggaaagcca tctgggttct ctcctttaaa aagcattcct ggaagcccca cctgtcgact   29520 tcccttatg tatcaaccat gtgtatgtca cttgaccaac ccacttgtat gttgtttgac   29580
cagccctggc tgcaatggag agtgggaaat acagtttttt caccaagtgc atggctgtcc   29640
aaatgaaatg agacttccat taataaggaa gaaaggaaag atggagatca ggaagctggg   29700
ggatcaggga acttattaca ttgagagccc ttggagtgaa ttctcttgca aatatgtccc   29760
tggaattgag aatccccaca acgtctttat ctgttctttc tttatccatg agtttgggtt   29820
ttcagatgtt ggatttccta tatggggggc atgtgagttc atcatcttcc ataatcaatg   29880
ttgtatcaac tggatttttct ctcttcttct caccagcctg gaggagaacc atctccagga   29940
tgaaggtgta tgttctctcg cagaaggact gaagaaaaat tcaagtttga aaatcctgaa   30000
gtaaggaacc cataagcagg aaacaggaca ataattgctg gcctttggaa ggggcatttc   30060
tgattaagat ctgggccgct ctccgctggg ctaactcatg tgaggtggcc tggtagaaca   30120
gcttgccttg gtctaggtgg acaaggattc cagtgcaagt tgtttatctg ggaggtggtc   30180
ccagtaaatg ctgataggag agtggtgaag tgagatgggg aagtgaaggt aaccaataaa   30240
ggggagttat caagccagtt atcaatgagg gaaattggag ctcagtactc tggggcactc   30300
```

```
ctggagccag tgcagaacac acatggtcac ctacccaacc aatgggcaag aaagccatgg   30360
catttatcca ccaaccctct gtccttccta tgttgatgtg cgctcatggg gcactgattc   30420
tccagcactt ccagctcacc ctcacccagc tgaacatgct tctggggtca ggagaatggc   30480
ctcaggcaga gagtggcagg tcttctctgc aagcagtggc tggggaggtg atgtgatggg   30540
gagtactgtg gcctcctcca gtggctgact cagtggcttg ggacttgtgc cacaaagaga   30600
tggacagctc aggtgaacat gaacccacct agtgaccatc atgggtttgt cagggtgctc   30660
tctgaggctg atgccaaaat tcttatttca agtagacctc aggaaccccca tcagatggct   30720 cctttttgctg gaggaaagtg gcatctgcct aggcaaatgt ggtcctagga aaacgcttgc   30780
ctttagagac agacagacag acagctgcct ctgtgagtgc cagctttgct gccaggctgc   30840
tacccactct ggcgacactc atttgtgttg ctttcacaag ctaggaagtt tccaaatatt   30900
tggagaaaac acttccacta attatttggg tggaaatggg ctgggaagtt ggggtgaagc   30960
ccggatgtgt ctgagccaga tgccagcttt gcactgaggg tcggcctttg ggaataccaa   31020
gcccattatc aaccaggtgt ggatatggca ggtttgtctt ccctccttgt cacagcctta   31080
ctccacttga ctcccatgga tgccaggcaa tgaggctggg gttggtccca tgccaccctg   31140
tcatcagcct tattttttcag catcctaaac tatatcatcc cccacaaaaa ttgaacttct   31200
gatatatctt ttataaaaaa gagaaatgcc tacatctttc ttttccagga ttagtttctg   31260
ccaagagttg gttgagagcc caggcttgct gggtgcagtg gctcacacct gtaatcccag   31320
cactttggga ggctgaggcg ggtggatcac ctgaggtggg gagttccata ccagcctgac   31380
caacatggag aaaccccatc tctactaaaa atacaaaatt agccgggcgt ggtggcatac   31440
acctgtaatc ccatctactc aggaagctga ggcaggagaa tcacttgaac ctgggaggtg   31500
gaggttgcca tgagccaaga tcacaccatt gcaccctaga ctggacaaga gagaaacttc   31560
catctcaaaa aaaaaaaaaa ggatgagaaa ataataatt taaaaaaaag agtccaggct   31620
ctggaaccag acagcctggg tcttaccccct gctccaccat taccagccag ttcttcttgg   31680
atgagtgcct cagttgcctc aagtgtaaat ggagataatg gctggacctt cattataggc   31740
catgagcatt cactgagaga atgtagctaa caaaagtgag ttgtaggttg gagcaaaagt   31800
aattgtggtt tcagaccatg aactttaaat tattataact aggctaaaat acatctttat   31860
taatcaaaat aggaaccatt aaaatcaaca cattttttgcc aataagaaat aagtttgttt   31920
attcctgtag cataaaaatt catgcttcgg gattcaacaa actcttggaa agcatttttct   31980 gcatcctcct ggttgtggaa gcattttttcc tgcagaaagt tgtcaagatt cttgaagaaa   32040
tggtagtcag ttggctagag gtcaggtaaa tatggcggat gaggcaaaac ttcatagtcc   32100
aattcattca acttttgaag ctttggttgt gtgacatgca gtccggttgt tgtcgcggag   32160
aattggaccc tttctgttga cgaatgccgg ttgcaggtgt tgcagttttc agtgcatctc   32220
attgacttgc cgagcatact tctcatatgt aatggtttcg cagggattca gaaagctgta   32280
ggggatcaga ctagcagcag accaccagtg accatgacct ttttttttttg gtgcgaattt   32340 gcctttggga agtgctttgg agcttcttct cggtccaacc actgagctag tcattgccag   32400
ttgtataaaa tccacttttc atcgcacgtc acaatcagat caagaaatgg ttcgctgttg   32460
ttgtgtagaa taagagaaga tgacacttca aaatgacgat tttcttggtt ttcactcagc   32520
tcatgaggca cacacttatc gaggttttttc acctttccaa tttgcttcaa atgctgaatg   32580
accatggaat ggtcgatgtt gagttctcaa gtagttgtaa gaaaatcagc tttgatgatt   32640
gctctcaatt ggtcattgtc agcttctgat ggcctgccag tacactcctc atcttcaagg   32700
```

```
ctcttatctc cttcgcaaaa cttcttgaac caccactgca ctatacgtta gttagcagtt    32760
cctgggccaa atgcattgct gatgttgtga gttgtctccg ctgctttaca acccattttg    32820
aattcaaata agaaaattgc ttgaatttgc tttttgtcta acatcatttt catagtctaa    32880
aataaatata aataaacag aaagtattaa gtcattagca aaaaatcata aagtgagaat    32940
tgtgcattaa aatgatgtat agcataacca catttattta agaatgtatt ccaatatcaa    33000
atggcaaatt tcaacaatgc aaaaactgca attacttttg caccaatcta atagaagttc    33060
aataaatact ggcaattaca attggcattg ccttagggtc aacttgtaag acattcctga    33120
aattgtggga aaggggggagg acctggagtg gacattattg gaaggcaaag ctgtaaccaa    33180
aagagcaacc tggaaacac atgactcctc tgttgctgtc cctggcccta tcctgtctcc    33240
cctccctgtt gtcagctacc tcatatgttc tctaatctct gtctctgtgc cctcaaagac    33300 cccctgaaa atagaaatat tactgctcat tggttatttt ctatcaatta agtactgtat    33360
tagtccgttt tcatgctgat gataaagata tacccaagac tgggcacttt atgaaagaaa    33420
gagttttatt gaacttacag ttccacgtgg ctggggaggt ctcacaatca tggctgaagg    33480
tgaaaggcac atctcacatg gcagcagaca ggagaagagg gcttgttcag ggaaactccc    33540 cttttaaaa ccatcagata tcatgaaact tatttactgt aatgagaaca ggatgggatt    33600
caattacctt ccactgggtc gctcccacaa acgtgggaa ttcaagagat ttgggtgggg    33660
acacagccaa accatatcaa gtactgtgca agtgttttag gcatgcagag agtggtgggt    33720
cttcccagca agcagagtgt ggggaggtaa tgggggactg gtggctgact taatggccca    33780
ggacccatgc cacaaggaga tggatggtgg atgtgaatag gagcctgctt acacccatca    33840
caatttagat tcttatgctc gatggcacgg gtactctttt aggcccattt taccaatgag    33900
gagattggga ctaatttgct cgagatcaaa aaagaagtgg tgtaggtggg atttaaaccc    33960
aggatgtcta gcactaaaat gcaggtactt aaccactatc ctaagggagt ggctacttaa    34020
tttgataaac tcatctagtg aatggaagag agacggttac atttcactga tggtactgag    34080
cctttgttga tgagctcatt gggaatctca gacatgagca ggatgtgtct aagggacagg    34140
tgggcttcag tagactggct aactcctgca gtctctttaa ctggacagtt tcaagaggaa    34200
aaccaagaat ccttgaagct caccattgta tcttcttttc caggttgtcc aataactgca    34260
tcacctacct aggggcagaa gccctcctgc aggcccttga aaggaatgac accatcctgg    34320
aagtctggta aggcccctgg gcaggcctgt tttagctctc cgaacctcag ttttctatc    34380 tgtaaaatgg ggtgacggga gagaggaatg gcagaatttt gaggatccct tctgattctg    34440
acattcagtg agaatgattc tgcatgtgaa ggatctgatt ctctgtctaa gaaagaagtc    34500
tttacctctt taagtaggga gcaatgattt cattttaaa ccttgactat ttattcagca    34560
acttctctgc tctatgagat agtgtaggaa tggggatgtg gttgaagaat gaaagaaaa    34620 gtcagctccc gccctcctag aaattgcatc tgccttcaca ggtcaaggat attggatcag    34680
accttctgcg gttctgaatg gagattacac aggttaggag caggttgcac agtgtttcca    34740
attctctata attaaagcca tagactttca tgtattgaaa aaagcaagaa ttgcattctt    34800
gacagattct ttcattgcct taaaaagaat gactagcctt gggagtctgg gcagctgggt    34860
ccagtgttgt agactttctc tctgctgagc cacagcttca aagatttgtc cttcttgttt    34920
ccagggatct atttctcaga caataagtaa aggctttccc tggcctaatg tgctgtaagt    34980
gaatgctact atatatgttc caggcactgg gctagagact aatatttaaa agccaggaaa    35040
tttcctatag aaaatctata tctcagggtt ttctcaaaag agctgggaac tctggatgcc    35100
```

```
cattcatgat tccagtagtt aaccagagta caagaagggc tgagtcttct cagatgggca    35160
aacccactct ggctgactgc agatccacca agcctattgt cttagaccag gacccttttgg   35220 caactcattc ccataagcct gtgacccttg ctttaaatat gcaggccttg tcttctctca    35280
aaaagcacat caaggctgca gcgaatgcag atatcaaatg atgaagttaa aaacaaaagc    35340
tttgctgggc gtggcagctc acacctgtaa tcctagcact tgggaggct gaggcaggag     35400 gatcacttta ggccagaggt tcaacaccag accttgtctc tcaaaaaata aaaaattcag    35460
ctgggtgcgg tgtagttcct agccacttgg gaggctggga tggaaggatc ccttgaaccc    35520
aggagttcaa ggctgcagtg ggccatgatt gcatcactgc acaggcgaca gaattagatc    35580
ccatctctta aaaaaataaa aaatttaaaa gtgacttcaa aaatctatgc tgtgatggag    35640 agattttcc ttctgtatga ttgtgatagc tctgtggcct atgacgtcat caggttctgg     35700
gcaaagtgta ggttttctgt ttctttgttt ttgaaaccat tgcacagtcc taagaaacat    35760
cacattctgg gtcctgggca ccagccaaca tgaggtgagg gcaccagggt ttgctcattg    35820
cattcttgac agattctctt attgccttaa aagaatcac tggccttggg gagtctgtgg     35880
ctggctgggt gcagtgttgt ggactctctc tgcagagtca tggagccttg ttcagaatgc    35940
ttcctgagct gccctggttg gccaagggta aaaacagccc tgacttccct gcaagaaaca    36000
ctgcagctgg gccagagagt cagcccatcc caggcatggg tttaaaaagt ggaggctttt    36060
gtttgaaagc cctgctctaa ttttgtcctc actcaaacct ctgttcactt gatctgcttt    36120
aggctccgag ggaacacttt ctctctagag gaggttgaca agctcggctg cagggacacc    36180
agactcttgc tttgaagtct ccgggaggat gttcgtctca gtttgtttgt gagcaggctg    36240
tgagtttggg ccccagaggc tgggtgacat gtgttggcag cctcttcaaa atgagccctg    36300
tcctgcctaa ggctgaactt gttttctggg aacaccatag gtcacctta ttctggcaga     36360 ggagggagca tcagtgccct ccaggataga cttttcccaa gcctacttt gccattgact     36420 tcttcccaag attcaatccc aggatgtaca aggacagccc ctcctccata gtatgggact    36480
ggcctctgct gatcctccca ggcttccgtg tgggtcagtg gggcccatgg atgtgcttgt    36540
taactgagtg cctttttggtg gagaggcccg gcctctcaca aaagacccct taccactgct    36600
ctgatgaaga ggagtacaca gaacacataa ttcaggaagc agctttcccc atgtctcgac    36660
tcatccatcc aggccattcc ccgtctctgg ttcctcccct cctcctggac tcctgcacac    36720
gctccttcct ctgaggctga aattcagaat attagtgacc tcagctttga tatttcactt    36780
acagcacccc caaccctggc acccagggtg ggaagggcta caccttagcc tgccctcctt    36840
tccggtgttt aagacatttt tggaagggga cacgtgacag ccgtttgttc cccaagacat    36900 tctaggttttg caagaaaaat atgaccacac tccagctggg atcacatgtg gacttttatt    36960
tccagtgaaa tcagttactc ttcagttaag ccttttggaaa cagctcgact ttaaaaagct    37020
ccaaatgcag ctttaaaaaa ttaatctggg ccagaatttc aaacggcctc actaggcttc    37080
tggttgatgc ctgtgaactg aactctgaca acagacttct gaaatagacc cacaagaggc    37140
agttccattt catttgtgcc agaatgcttt aggatgtaca gttatggatt gaaagtttac    37200
aggaaaaaaa attaggccgt tccttcaaag caaatgtctt cctggattat tcaaaatgat    37260
gtatgttgaa gcctttgtaa attgtcagat gctgtgcaaa tgttattatt ttaaacatta    37320
tgatgtgtga aaactggtta atatttatag gtcactttgt tttactgtct taagtttata    37380
ctcttataga caacatggcc gtgaacttta tgctgtaaat aatcagaggg gaataaactg    37440
ttg                                                                 37443
```

<210> SEQ ID NO 4
<211> LENGTH: 1315
<212> TYPE: DNA
<213> ORGANISM: Homo sapiens
<220> FEATURE:
<223> OTHER INFORMATION: IBD1prox cDNA
<220> FEATURE:
<221> NAME/KEY: CDS
<222> LOCATION: (117)..(1121)
<223> OTHER INFORMATION: IBD1prox

<400> SEQUENCE: 4

```
cgatcagaag caggtcacac agcctgtttc ctgttttcaa acggggaact tagaaagtgg      60
cagcccctcg gcttgtcgcc ggagctgaga accaagagct cgaagggcc atatga cac     119
                                                                His
                                                                1 tcc tcc cgg acc cct gga cac aca cag ccc tgg aga ctg gag cct tgg      167
Ser Ser Arg Thr Pro Gly His Thr Gln Pro Trp Arg Leu Glu Pro Trp
        5                   10                  15 agc atg gca agt cca gag cac cct ggg agc cct ggc tgc atg gga ccc      215
Ser Met Ala Ser Pro Glu His Pro Gly Ser Pro Gly Cys Met Gly Pro
    20                  25                  30 ata acc cag tgc acg gca agg acc cag cag gaa gca cca gcc act ggc      263
Ile Thr Gln Cys Thr Ala Arg Thr Gln Gln Glu Ala Pro Ala Thr Gly
35                  40                  45 ccc gac ctc ccg cac cca gga cct gac ggg cac tta gac aca cac agt      311
Pro Asp Leu Pro His Pro Gly Pro Asp Gly His Leu Asp Thr His Ser
 50                  55                  60                  65 ggc ctg agc tcc aac tcc agc atg acc acg cgg gag ctt cag cag tac      359
Gly Leu Ser Ser Asn Ser Ser Met Thr Thr Arg Glu Leu Gln Gln Tyr
                70                  75                  80 tgg cag aac cag aaa tgc cgc tgg aag cac gtc aaa ctg ctc ttt gag      407
Trp Gln Asn Gln Lys Cys Arg Trp Lys His Val Lys Leu Leu Phe Glu
            85                  90                  95 att gct tca gct cgc atc gag gag aga aaa gtc tct aag ttt gtg gtg      455
Ile Ala Ser Ala Arg Ile Glu Glu Arg Lys Val Ser Lys Phe Val Val
        100                 105                 110 tac caa atc atc gtc atc cag act ggg agc ttt gac aac aac aag gcc      503
Tyr Gln Ile Ile Val Ile Gln Thr Gly Ser Phe Asp Asn Asn Lys Ala
    115                 120                 125 gtc ctg gaa cgg cgc tat tcc gac ttc gcg aag ctc cag aaa gcg ctg      551
Val Leu Glu Arg Arg Tyr Ser Asp Phe Ala Lys Leu Gln Lys Ala Leu
130                 135                 140                 145 ctg aag acg ttc agg gag gag atc gaa gac gtg gag ttt ccc agg aag      599
Leu Lys Thr Phe Arg Glu Glu Ile Glu Asp Val Glu Phe Pro Arg Lys
                150                 155                 160 cac ctg act ggg aac ttc gct gag gag atg atc tgt gag cgt cgg cgc      647
His Leu Thr Gly Asn Phe Ala Glu Glu Met Ile Cys Glu Arg Arg Arg
            165                 170                 175 gcc ctg cag gag tac ctg ggc ctg ctc tac gcc atc cgc tgc gtg cgc      695
Ala Leu Gln Glu Tyr Leu Gly Leu Leu Tyr Ala Ile Arg Cys Val Arg
        180                 185                 190 cgc tcc cgg gag ttc ctg gac ttc ctc acg cgg ccg gag ctg cgc gag      743
Arg Ser Arg Glu Phe Leu Asp Phe Leu Thr Arg Pro Glu Leu Arg Glu
    195                 200                 205 gct ttc ggc tgc ctg cgg gcc ggc cag tac ccg cgc gcc ctg gag ctg      791
Ala Phe Gly Cys Leu Arg Ala Gly Gln Tyr Pro Arg Ala Leu Glu Leu
210                 215                 220                 225 ctg ctg cgc gtg ctg ccg ctg cag gag aag ctc acc gcc cac tgc cct      839
Leu Leu Arg Val Leu Pro Leu Gln Glu Lys Leu Thr Ala His Cys Pro
                230                 235                 240
```

-continued

```
gcg gcc gcc gtc ccg gcc ctg tgc gcc gtg ctg ctg tgc cac cgc gac      887
Ala Ala Ala Val Pro Ala Leu Cys Ala Val Leu Leu Cys His Arg Asp
            245                 250                 255 ctc gac cgc ccc gcc gag gcc ttc gcg gcc gga gag agg gcc ctg cag      935
Leu Asp Arg Pro Ala Glu Ala Phe Ala Ala Gly Glu Arg Ala Leu Gln
        260                 265                 270 cgc ctg cag gcc cgg gag ggc cat cgc tac tat gcg cct ctg ctg gac      983
Arg Leu Gln Ala Arg Glu Gly His Arg Tyr Tyr Ala Pro Leu Leu Asp
    275                 280                 285 gcc atg gtc cgc ctg gcc tac gcg ctg ggc aag gac ttc gtg act ctg     1031
Ala Met Val Arg Leu Ala Tyr Ala Leu Gly Lys Asp Phe Val Thr Leu
290                 295                 300                 305 cag gag agg ctg gag gag agc cag ctc cgg agg ccc acg ccc cga ggc     1079
Gln Glu Arg Leu Glu Glu Ser Gln Leu Arg Arg Pro Thr Pro Arg Gly
                310                 315                 320 atc acc ctg aag gag ctc act gtg cga gaa tac ctg cac tga              1121
Ile Thr Leu Lys Glu Leu Thr Val Arg Glu Tyr Leu His
                325                 330 gccggcctgg accccgcag ggacgctgga gatttggggt caccatggct cacagtgggc    1181
tgtttggggt tcttttttt tattttcct tttcttttt gttatttgag acagtcttgc     1241
tctgtcaccc agactgaagt gcagtggctc aattatgtct cactgcagcc tcaaactcct   1301
gggcacaagc aatc                                                     1315

<210> SEQ ID NO 5
<211> LENGTH: 334
<212> TYPE: PRT
<213> ORGANISM: Homo sapiens
<220> FEATURE:
<223> OTHER INFORMATION: IBD1prox

<400> SEQUENCE: 5

His Ser Ser Arg Thr Pro Gly His Thr Gln Pro Trp Arg Leu Glu Pro
 1               5                  10                  15

Trp Ser Met Ala Ser Pro Glu His Pro Gly Ser Pro Gly Cys Met Gly
            20                  25                  30

Pro Ile Thr Gln Cys Thr Ala Arg Thr Gln Gln Glu Ala Pro Ala Thr
        35                  40                  45

Gly Pro Asp Leu Pro His Pro Gly Pro Asp Gly His Leu Asp Thr His
    50                  55                  60

Ser Gly Leu Ser Ser Asn Ser Ser Met Thr Thr Arg Glu Leu Gln Gln
65                  70                  75                  80

Tyr Trp Gln Asn Gln Lys Cys Arg Trp Lys His Val Lys Leu Leu Phe
                85                  90                  95

Glu Ile Ala Ser Ala Arg Ile Glu Glu Arg Lys Val Ser Lys Phe Val
            100                 105                 110

Val Tyr Gln Ile Ile Val Ile Gln Thr Gly Ser Phe Asp Asn Asn Lys
        115                 120                 125

Ala Val Leu Glu Arg Arg Tyr Ser Asp Phe Ala Lys Leu Gln Lys Ala
    130                 135                 140

Leu Leu Lys Thr Phe Arg Glu Glu Ile Glu Asp Val Glu Phe Pro Arg
145                 150                 155                 160

Lys His Leu Thr Gly Asn Phe Ala Glu Glu Met Ile Cys Glu Arg Arg
                165                 170                 175

Arg Ala Leu Gln Glu Tyr Leu Gly Leu Leu Tyr Ala Ile Arg Cys Val
            180                 185                 190

Arg Arg Ser Arg Glu Phe Leu Asp Phe Leu Thr Arg Pro Glu Leu Arg
```

```
                    195                 200                 205
Glu Ala Phe Gly Cys Leu Arg Ala Gly Gln Tyr Pro Arg Ala Leu Glu
    210                 215                 220

Leu Leu Leu Arg Val Leu Pro Leu Gln Glu Lys Leu Thr Ala His Cys
225                 230                 235                 240

Pro Ala Ala Val Pro Ala Leu Cys Ala Val Leu Leu Cys His Arg
                245                 250                 255

Asp Leu Asp Arg Pro Ala Glu Ala Phe Ala Ala Gly Glu Arg Ala Leu
                260                 265                 270

Gln Arg Leu Gln Ala Arg Glu Gly His Arg Tyr Tyr Ala Pro Leu Leu
    275                 280                 285

Asp Ala Met Val Arg Leu Ala Tyr Ala Leu Gly Lys Asp Phe Val Thr
    290                 295                 300

Leu Gln Glu Arg Leu Glu Glu Ser Gln Leu Arg Arg Pro Thr Pro Arg
305                 310                 315                 320

Gly Ile Thr Leu Lys Glu Leu Thr Val Arg Glu Tyr Leu His
                325                 330

<210> SEQ ID NO 6
<211> LENGTH: 8135
<212> TYPE: DNA
<213> ORGANISM: Homo sapiens
<220> FEATURE:
<221> NAME/KEY: exon
<222> LOCATION: (1)..(161)
<220> FEATURE:
<221> NAME/KEY: exon
<222> LOCATION: (3812)..(3950)
<220> FEATURE:
<221> NAME/KEY: exon
<222> LOCATION: (5426)..(5577)
<220> FEATURE:
<221> NAME/KEY: exon
<222> LOCATION: (7273)..(8135)

<400> SEQUENCE: 6
cgatcagaag caggtcacac agcctgtttc ctgttttcaa acggggaact tagaaagtgg      60
cagcccctcg gcttgtcgcc ggagctgaga accaagagct cgaagggggcc atatgacact    120 cctcccggac ccctggacac acacagcccct ggagactgga ggtcagtatt tgatcccaag    180
ctcagctgtc ctctgcctgc tgtggcctga gtccccttct cctggggccc tgcctggcac    240
ctgctggggg cagggtggga gggggaagag ttagtgacag ccgctgtgtc tggagctctc    300
cttagcacac tgaggcagag gaagggacag ctcctggacc ttccatcacc tccattcctt    360
ttgaaatgct aggcgcttgt acaacccatc ttgggcctgg agaataagtc accacacctg    420
tgtttctcaa aagaacagtg tcaggggaacc cctgcctcag cacagcctta gaggactcat   480
ggaaaatgca gaatccaggc ctgttcaatg gcaccttcct atgttagcag ccaggaaacc    540
tgctcttgga caagccccctg ggatcccacc cccacccccac cagggggattc ttacacacac  600 tgggttggga gcccctggct ttggcaaggc ttctcaggtg agcgtccagt tgttggaggg    660
tacccaccct ttccccaaga gaggcagcca cacatccaac atcctgggat ctctgtctcc    720
cagcgtgggc catgtgcttt atttcacccc ctagaggctc atcccccatg aaaagtcctc    780
cgcaggccct cagaaagata gtgtggcctc tgtgtgccca gcagaagaag gactggactt    840
ggcagtcagc tcttggagag ggggtggtta ggacacctgg ggacaggagg aggagaatga   900
ctgtctgtgc acacacggct ggaaggtaca ggaaggctggg aagctgctct gtccccctggg 960 ccaactacag gccccccaggc caacagcaac aaacacttttaa gtattttgtt ataaagtcaa 1020
```

```
gaaatctttg ctacagaggg tgaggagagg gaaggaaagg gccatggaac cgtctatgtg    1080
gctatcccca gagagctttt agagtgacag gattgctttc ccatttcaca gatgaggaaa    1140
ctgaggcctg gagagggatg ggaagctacc caaggcccca tggatacacc agtgcacaac    1200
tctttccttc cccctcctct ttaaatgggt gattcccaat gaaacctgta agagacaacc    1260
ataagggagc tgactgtggc tgctgaattt gattttattc taaggcctgg ttttataatc    1320
agctttctca gtctttactg gagtgtcaag ccgaggcatc atttctaggg tcttacaggg    1380
tctctgggcc aatagtgccc tgcttctgac ctggagccag ctgcctggtc atgaaagcag    1440
atctgcaaag gctggggccc ctgaggccaa ggccactcgc catcacccat tttacagaag    1500
tgctgagcat aggagtgccc tgggccccca agaatcccag ccaccaagaa tcacgtaaac    1560
catccactgt ctcacttagg caccagtcag aatgtaggga acccacccct agtcatccat    1620
catcttatca acaggacggg gcttgtagcc acatttatca ggtagggaaa ctgaagccta    1680
gagatattaa agcacttgct taaggacaca cggttggtca ggatggaagg cgatgtctcc    1740
tgactccctg acaggcacaa gagacaagcg agaggtgccc gtgacggcat gctcaagaac    1800
gtgcagccct gggccagcca ggcccctgct ccgtgcctct gtttgcccat ctgtaaaagg    1860
tgaggttgga tcgagggtcc ctgagggccg cccactggat ggctgtgcag agccaaacgg    1920
agaaggcccc agggttcctt tcacccgaca cagcaagcac ttcccccctga agtgcaggct    1980 ccaggcccca gctgacctcc cctctcccag gccagcggct ctcacccctg gagcaaggga    2040
caggcgctgg ctgtgctcag ggacatgcat gactcccgcc cccatctgtg ctcagggggt    2100
gccagggagg cactggctct atctttctct aggccgtagt cagcccaggg gttcagacca    2160
agagcccaga atccaacaga tcagagttca agtcccagct ctacctctat gttccactgg    2220
cagcttcctc aggtcatttg caccttcctt gtcttgaatt tccatgccta accagtatac    2280
cagctactcc ctccagccga tctaatgttt taattgtccc tttctctaag ttgtctcaaa    2340
catttgtaat tctattccaa tccaccttaa tttagtcatt tatttcacaa atatttctgg    2400
aaacatctag cacttaacag acactaaaag cgggggtact acacagtccc tgggatggac    2460
agggccctga gctgaggctt cagagtctgc ctgactgaat cctcaccccca gccttgtgaa    2520 cgtgggttct gttattatcc ccaatttata ggaaacagaa gcacagagaa gttgagtcac    2580
ttgccagcta ccaggtcatc ccttccactt atccgggtca cagacagagt tattatgtaa    2640
accagatccc agctgcctgt tctccctccc tgagtaaggt ggagagaatt ctgaagtcag    2700
cccagcctgg gtctgtatcc tgcccaccac tcaccagctc ctcatctttg gcaactctaa    2760
gtctcagttc ccttatcata aaagggagat gtaaacagtc ctgagtgcag acagtgttca    2820
ggttagtgca agagtgtgtg ctgggtgtga agtgcacagc cagcacgtca caagcactgg    2880
agacaaattc agctttgctt gttgcgcaca ctcaccagct gcgtgacttt agacctcagt    2940
tttctcatct gttatgtggt ggtaatgata gacttttgtg agcattaaac tagattaggg    3000
gctatggaga acctagatgg gtatgaagtg ggtataataa gctatcagtt aattttgctg    3060
atagatagat tattgattga ttgatcgata gaagattcat accagtatct acctgctctg    3120
aacactgacc tttctttttt tcttttttgag atggtcttgt tctgtcaccc agactggagt    3180
gcagtggcat catcatagct cactgcagcc tcagtctctt gggcttaagg gatcctcctg    3240
tctcagcctc ccaagtagct gggaccacag gcgtgcatcc tggataattt ttttttattt    3300
tttctagaga cggggtctca ctacattggc caggctggtc tcaaattcct gggctcaagt    3360
gatccttcta acccagcctc ccaaagcgct gggattacag gcatgagtgg ccatgttcaa    3420
```

```
cttgaacact gagacttcat tcgcatgtgt aacataaaac tgagtatcta gacaagccag    3480
catctttctt tcaagtaatc actaaagcca atacttttac ttgaaatcat ctcatttaaa    3540
actctgagca atacgtaagg atcacctcaa taacatatgg atcatcgcaa taggtgaagg    3600
gtcttctctg ccttggagta acctgcccag caaaggggca gacccagatt tgggatctgg    3660
cagctgggag agtggggaag gttgagccgt ggggcccttg tcattccctc tgcctgccag    3720
gagggggcat gacacagctc ctaggcaccc caggagccac cgggaacccc aactggagtg    3780
ggtcctcact gttctctttt tcctctggca gccttggagc atggcaagtc cagagcaccc    3840
tgggagccct ggctgcatgg gacccataac ccagtgcacg gcaaggaccc agcaggaagc    3900
accagccact ggccccgacc tcccgcaccc aggacctgac gggcacttag gtgggcttga    3960
ggcttgagac tcggtctggg ggagaggtct gaagacattc aaagtacaaa tgtgggtcac    4020
tttgggggat gcagcaagag gcccgggcag ctcttgtaac ttgggttatc ccaaaacaga    4080
cactgagaca cagatctagt gcaagctgtt tatccgggag acggtcctag gagtcatggc    4140
aggggagtgg gaatggaagg aaagggcaag aggccagggc aggacatcag tgaacagata    4200
ggcacggtag gtggctgaag ctcaaccccca gcggggtct tctgggagac cctgaacat    4260 atctctgggt tgtcctatcc taggggtgag gaagccgggc tgttatctac cagtcctgcc    4320
ctgcatagga gaagggacgc tcctgggcct gctgctatgg ccctagaaag ccctcaggga    4380
agccagtggc atgttctgga aaagtgggtg ccaagagggc acggtccagc ctggggcatg    4440
gacagcatct gctgtagtgc catctcctgg aacagatctt tcttacagt ccttcgagat    4500 gccctattca ataccgtctc tgttcctggc cctatgcagg gcactggaga aacagaaaca    4560
ggaagaaatc aaacactgca ctagtcctga ggtttggtag agaaacagat cagtgagaaa    4620
cagttacacg tgccacgaga aataaataaa taaaatgaaa aacctgtagg aacaaggtgg    4680
gaagctctta ctctaatgcc aaggggcatt tgcagtgatg tggggctgg gtcttgaagg    4740 gtagactgga aaagggctgg gacccatgcc cttttgcaata aaatgcacaa ttatttgtgc    4800
ttcttaagaa cctcagagtg gcgcagggct caagtggggt ttaagaaaca ctgtgttcgt    4860
tttccaggcg tggaaataga ggggttggatg caaggcagag cagtgcacgt ccgagaagag    4920
cccggcatgt gggcagttag atgagaaggt taggaagggc cagcccgctg aggctggaac    4980
ataacatcct cctcactgcc tcccctgccc actgatgtgt gctcaaggag tcgtggcaac    5040
agtcacgaag tcagggctgc agggagcaca gaaacacaca agccaccgtc tctgcttgtc    5100
cagagcaggg atttcaccat ggccaatcta cagaccagaa gtggacgatg caaagtgccc    5160
gcaccgcatt ccaaagctgt gaaaccactt ggggggtgatg ggctatttgg gattgtcggt    5220
ggtagggtgg attctgccag gctgggcaca gaggtctgtc tgatgcccca attgggccta    5280
taaatggcgg ggtgggagag agggatattc aatactcttc aggagttctg atatgccatc    5340
tcagatagac ccagccatct ccccaagccc atgcctcgga agtgcactga cagggtgcag    5400
atccttaagg gtgttgtcct tccagacaca cacagtggcc tgagctccaa ctccagcatg    5460
accacgcggg agcttcagca gtactggcag aaccagaaat gccgctggaa gcacgtcaaa    5520
ctgctctttg agatcgcttc agctcgcatc gaggagagaa aagtctctaa gtttgtggta    5580
agcagagatt gggaaatggt ggagcctctt tcactctgct tccttcctgg ccctgaataa    5640
gtcttgtaga gcctcaggtt tcccaactat gaaatgggtc aacacactaa ctcacagctt    5700
tcttctggag aaaatggcca aagagcaaga tttcaggctc agcacctgct agggtctgtg    5760
aggattcgaa ccatataagt catatttctt ggtcccaaga aggaaatagc ccagtttaat    5820
```

-continued

```
cccatcttat caggtgtcag tcacctgtgt cctttcttca ccaattttgc catatcactg      5880
tatctgttct aattattatt acttattttt ttctttaaat tggatcactt tttaaaaaca      5940
tgaagcacat ttatttcaaa gagaaatacc ttaaatggaa aaccaatatc acatggcaca      6000
aagcaaaagt aacatactag aaaagtcgat acaaggaaag tcaatacaag gaaagctatg      6060
tgctgttatt aaattctagc tggttactgt ggcttcggga aagccctgtg cctgggagct      6120
gctcctctcc ctgttagaat ggaattttag cttgtgttaa gggatgttaa agactgccta      6180
agagccacac ttcatccttc tccttcactt acctgggacc gggataaata acatagctac      6240
cactgaatgc caatggcatg ccgggcacag ctccatgtgg tttcagtgca ttaactcatt      6300
taatcctcac tgggtgaggt aggcactatg cctatccttg ttttatgaat gagaaaagtg      6360
agactcggag aggttaaatt actcatctaa aaccacacag ctagaccatg gtagggctat      6420
aattacaacc catgcaatct ggctctggag tcagatgcat gggttataat tgcccttaat      6480
atataattgc ccgtaatcag gattctcttg aaagatgatt gaaaggatt gattttctta       6540 ccatataacg gcatcaccag tgtacctaaa tgatgttata ttgtacgtaa aactaattcc      6600
caagtgtgaa acatttggaa aacacagcat ctcagttcag aaaacagagg cccagtttta      6660
gcaagtaaag ccaagaggga ccccagcagc ctgcagggca ggaccctctg cccttctcc       6720 tcccagatgt ccccaccttg ctgtgttgtt gttccagggt tgactcagct gatgccaata      6780
gcaatttaaa acagaattgg gccaggtgca gtggctcatg cctgtaatcc cagcactttg      6840
ggaggcccag gtaggaggat cgcttgagcc caggagttgg agaccagcct gggcaacaca      6900
gccagacccc atctttaaa aagaatcaaa aaatctgcca ggtagtgggt gtgcctgtag       6960
tcccagctac tcaggaggct caggtgggca ggtcaattga gcccataagt tcaaggttgc      7020
agtgaggtat gatcgcatca ctgtactcca gcctgggtaa cagtgcgaga ccctgtctct      7080
aaaaataaat aaataaataa ataaataaat aaataaacaa acaaacaaac aaacaaacaa      7140
tcaattgcat ataaggatcg cccgtttca gggcatgctt tacaccggcc tggttaactt       7200
tactctgggt gtgctccgtc cgccgcagcc cccgccggga ggtggccaca gctctctctg      7260
gttgcgccct aggtgtacca aatcatcgtc atccagactg ggagctttga caacaacaag      7320
gccgtcctgg aacggcgcta ttccgacttc gcgaagctcc agaaagcgct gctgaagacg      7380
ttcagggagg agatcgaaga cgtggagttt cccaggaagc acctgactgg gaacttcgct      7440
gaggagatga tctgtgagcg tcggcgcgcc ctgcaggagt acctgggcct gctctacgcc      7500
atccgctgcg tgcgccgctc ccgggagttc ctggacttcc tcacgcggcc ggagctgcgc      7560
gaggctttcg gctgcctgcg ggccggccag tacccgcgcg ccctggagct gctgctgcgc      7620
gtgctgccgc tgcaggagaa gctcaccgcc cactgccctg cggccgccgt cccggccctg      7680
tgcgccgtgc tgctgtgcca ccgcgacctc gaccgccccg ccgaggcctt cgcggccgga      7740
gagagggccc tgcagcgcct gcaggcccgg gagggccatc gctactatgc gcctctgctg      7800
gacgccatgg tccgcctggc ctacgcgctg ggcaaggact tcgtgactct gcaggagagg      7860
ctggaggaga gccagctccg gaggcccacg ccccgaggca tcaccctgaa ggagctcact      7920
gtgcgagaat acctgcactg agccggcctg gaccccgca gggacgctgg agatttgggg      7980
tcaccatggc tcacagtggg ctgtttgggg ttctttttt ttattttcc ttttcttttt        8040 tgttatttga cacagtcttg ctctgtcacc cagactgaag tgcagtggct caattatgtc      8100
tcactgcagc ctcaaactcc tgggcacaag caatc                                 8135
```

<210> SEQ ID NO 7

```
<211> LENGTH: 16
<212> TYPE: DNA
<213> ORGANISM: Artificial Sequence
<220> FEATURE:
<223> OTHER INFORMATION: Description of Artificial Sequence:PCR primer
      for D16S3120 (AFM326vc5) polymorphism marker

<400> SEQUENCE: 7
ctgggtgcga ttgctc                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence:PCR primer
      for D16S3120 (AFM326vc5) polymorphism marker

<400> SEQUENCE: 8
ccaggcccca tgacag                                                    16

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S298 (AFMa189wg5) polymorphism marker

<400> SEQUENCE: 9
tggtcccggc ccaatcccaa tgctt                                          25

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:PCR primer
      for D16S298 (AFMa189wg5) polymorphism marker

<400> SEQUENCE: 10
ttcctcatgt ataaattggg tgtggcca                                       28

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S299 polymorphism marker

<400> SEQUENCE: 11
acagagtgag gaccccatct ctatc                                          25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S299 polymorphism marker

<400> SEQUENCE: 12
tccaactgct gggattacag gcaca                                          25

<210> SEQ ID NO 13
<211> LENGTH: 22
<212> TYPE: DNA
```

```
<213> ORGANISM: Artificial Sequence
<220> FEATURE:
<223> OTHER INFORMATION: Description of Artificial Sequence:PCR primer
      for SPN polymorphism marker

<400> SEQUENCE: 13
agtccccgag accagggcaa ac                                            22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:PCR primer
      for SPN polymorphism marker

<400> SEQUENCE: 14
tccatttctg cagtacacat gca                                           23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S383 polymorphism marker

<400> SEQUENCE: 15
ctctccccat agaaggcatc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S383 polymorphism marker

<400> SEQUENCE: 16
ggatagagac gttctcttaa                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S753 (GGAA3G05) polymorphism marker

<400> SEQUENCE: 17
caggctgaat gacagaacaa                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S753 (GGAA3G05) polymorphism marker

<400> SEQUENCE: 18
attgaaaaca actccgtcca                                               20

<210> SEQ ID NO 19
<211> LENGTH: 25
<212> TYPE: DNA
<213> ORGANISM: Artificial Sequence
<220> FEATURE:
```

<223> OTHER INFORMATION: Description of Artificial Sequence:PCR primer
      for D16S3044 (AFMa222za9) polymorphism marker

<400> SEQUENCE: 19
atactcactt ttagacagtt caggg                                          25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:PCR primer
      for D16S3044 (AFMa222za9) polymorphism marker

<400> SEQUENCE: 20
ggctcagttc ctaaccagtt c                                              21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S409 (AFM161xa1) polymorphism marker

<400> SEQUENCE: 21
agtcagtctg tccagaggtg                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S409 (AFM161xa1) polymorphism marker

<400> SEQUENCE: 22
tgaatcttac atcccatccc                                                20

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:PCR primer
      for D16S3105 (AFMb341zc5) polymorphism marker

<400> SEQUENCE: 23
gatcttccca aagcgcc                                                   17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:PCR primer
      for D16S3105 (AFMb341zc5) polymorphism marker

<400> SEQUENCE: 24
tcccgtcagc caagcta                                                   17

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S261 (MFD24) polymorphism marker

<400> SEQUENCE: 25
aagcttgtat ctttctcagg                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S261 (MFD24) polymorphism marker

<400> SEQUENCE: 26
atctaccttg gctgtcattg                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S540 (GATA7B02) polymorphism marker

<400> SEQUENCE: 27
cctccataat catgtgagcc                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S540 (GATA7B02) polymorphism marker

<400> SEQUENCE: 28
aatctcccca actcaagacc                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S3080 (AFMb068zb9) polymorphism marker

<400> SEQUENCE: 29
ggatgcctgc tctaaatacc                                                   20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:PCR primer
      for D16S3080 (AFMb068zb9) polymorphism marker

<400> SEQUENCE: 30 cccagggtc aaacttaat                                                     19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:PCR primer
      for D16S517 (AFMa132we9) polymorphism marker

<400> SEQUENCE: 31

-continued

```
ggtttgaaag tatctccagg g                                           21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:PCR primer
      for D16S517 (AFMa132we9) polymorphism marker

<400> SEQUENCE: 32
ggtttgaaag tatctccagg g                                           21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S411 (AFM186xa3) polymorphism marker

<400> SEQUENCE: 33
gtgcatgtgt tcgtatcaac                                             20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S411 (AFM186xa3) polymorphism marker

<400> SEQUENCE: 34
tcatctccaa aggagtttct                                             20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:PCR primer
      for D16S3035 (AFMa189wg5) polymorphism marker, PCR or ligation
      oligonucleotide primer for D16S3035 biallelic polymorphism marker

<400> SEQUENCE: 35
aaagccaacc ttgcttca                                               18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S3035 (AFMa189wg5) polymorphism marker, PCR or ligation
      oligonucleotide primer for D16S3035 biallelic polymorphism marker

<400> SEQUENCE: 36
tcttggaaac aggtaagtgc                                             20

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:PCR primer
      for D16S3136 (AFMa061xe5) polymorphism marker, PCR or ligation
      oligonucleotide primer for D16S3136 biallelic polymorphism marker
```

```
<400> SEQUENCE: 37
attgccctca agaacagc                                                18

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence:PCR primer
      for D16S3136 (AFMa061xe5) polymorphism marker, PCR or ligation
      oligonucleotide primer for D16S3136 biallelic polymorphism marker

<400> SEQUENCE: 38
gtgctatgcc atcccag                                                 17

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S541 (GATA7E02) polymorphism marker

<400> SEQUENCE: 39
ccacaccagc gttttctaa                                               20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:PCR primer
      for D16S541 (GATA7E02) polymorphism marker

<400> SEQUENCE: 40
cacactttac acacacctat accc                                         24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:PCR primer
      for D16S3117 (AFM288wb1) polymorphism marker

<400> SEQUENCE: 41
aagccatatt aggtctgtcc at                                           22

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence:PCR primer
      for D16S3117 (AFM288wb1) polymorphism marker

<400> SEQUENCE: 42
gcttgggtta aatgcgtgt                                               19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S416 (AFM210yg3) polymorphism marker

<400> SEQUENCE: 43
```

```
agcagtttgg gtaaacattg                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S416 (AFM210yg3) polymorphism marker

<400> SEQUENCE: 44
aaatatgcct tctggaggtg                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S770 (GGAA20G02) polymorphism marker

<400> SEQUENCE: 45
ggaggatcag gggagtttat                                                 20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:PCR primer
      for D16S770 (GGAA20G02) polymorphism marker

<400> SEQUENCE: 46
caaagtaaat gaatgtctac tgcc                                            24

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:PCR primer
      for D16S2623 (GATA81B12) polymorphism marker

<400> SEQUENCE: 47
ccaactctgt agtttcaaag agc                                             23

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S2623 (GATA81B12) polymorphism marker

<400> SEQUENCE: 48
tcacagccta cttgcttggt                                                 20

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S390 polymorphism marker

<400> SEQUENCE: 49
gacagcctca aatgaaatat aacac                                           25
```

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S390 polymorphism marker

<400> SEQUENCE: 50
gctctcagct agggtagttg tttat                                       25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S419 (AFM225zf2) polymorphism marker
<220> FEATURE:
<221> NAME/KEY: modified_base
<222> LOCATION: (20)
<223> OTHER INFORMATION: n = g, a, c, t, other or unknown

<400> SEQUENCE: 51
atttttaagg aatgtaaagn acaca                                       25

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S419 (AFM225zf2) polymorphism marker

<400> SEQUENCE: 52
gaccaggagt cagtaaaagg                                             20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S771 (GGAA23C09) polymorphism marker

<400> SEQUENCE: 53
gtccaaaaca ccaccctcta                                             20

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:PCR primer
      for D16S771 (GGAA23C09) polymorphism marker

<400> SEQUENCE: 54
gaagtagatc agtcatcttg ctgc                                        24

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence:PCR primer
      for D16S408 (AFM137xf8) polymorphism marker

<400> SEQUENCE: 55
tcctctgggg gattcactc                                               19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S408 (AFM137xf8) polymorphism marker

<400> SEQUENCE: 56
gggacatcac caagcacaag                                              20

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:PCR primer
      for D16S508 (AFM304xf1) polymorphism marker

<400> SEQUENCE: 57
caggaaaata aatctaacac acata                                        25

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:PCR primer
      for D16S508 (AFM304xf1) polymorphism marker

<400> SEQUENCE: 58
cctgtgggca ctgataaata                                              20

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for ADCY7int7 biallelic
      polymorphism marker

<400> SEQUENCE: 59
cccagccccc atctcaccg                                               19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for ADCY7int7 biallelic
      polymorphism marker

<400> SEQUENCE: 60
cccagccccc atctcacca                                               19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for ADCY7int7 biallelic
      polymorphism marker

```
<400> SEQUENCE: 61
ctgcggagga ggctgctgg                                                  19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for hb133D1f biallelic
      polymorphism marker

<400> SEQUENCE: 62
tcactcccac caccctttc                                                  19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for hb133D1f biallelic
      polymorphism marker

<400> SEQUENCE: 63
agaagtttag tgtggcgtgg                                                 20

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg35ExC biallelic
      polymorphism marker

<400> SEQUENCE: 64
gccatctccc caagccc                                                    17

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg35ExC biallelic
      polymorphism marker

<400> SEQUENCE: 65
tcgatgcgag ctgaagcg                                                   18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg35ExC biallelic
      polymorphism marker

<400> SEQUENCE: 66
tcgatgcgag ctgaagca                                                   18

<210> SEQ ID NO 67
<211> LENGTH: 20
<212> TYPE: DNA
<213> ORGANISM: Artificial Sequence
<220> FEATURE:
```

-continued

<223> OTHER INFORMATION: Description of Artificial Sequence:PCR or
      ligation oligonucleotide primer for CTG35ExA biallelic
      polymorphism marker

<400> SEQUENCE: 67
tgaatgttaa agggctctgg                                              20

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for CTG35ExA biallelic
      polymorphism marker

<400> SEQUENCE: 68
ttggttctca gctccggcg                                               19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for CTG35ExA biallelic
      polymorphism marker

<400> SEQUENCE: 69
ttggttctca gctccggca                                               19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for Ctg25Ex1 biallelic
      polymorphism marker

<400> SEQUENCE: 70
agaaaccggg ctggctgtg                                               19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence:PCR or
      ligation oligonucleotide primer for Ctg25Ex1 biallelic
      polymorphism marker

<400> SEQUENCE: 71
gcattgcctt ttgatctcta c                                            21

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP3-2931 biallelic
      polymorphism marker

<400> SEQUENCE: 72
tgggctcttc tgcgggga                                                18

<210> SEQ ID NO 73

```
<211> LENGTH: 18
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP3-2931 biallelic
      polymorphism marker

<400> SEQUENCE: 73
tgggctcttc tgcggggg                                                18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP3-2931 biallelic
      polymorphism marker

<400> SEQUENCE: 74
tgcctcttct tctgccttcc                                              20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-5ag/ola biallelic
      polymorphism marker

<400> SEQUENCE: 75
cgagctgtac ctgaggaagc gt                                           22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-5ag/ola biallelic
      polymorphism marker

<400> SEQUENCE: 76
cctgagctgt acctgaggaa gcgc                                         24

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-5ag/ola biallelic
      polymorphism marker

<400> SEQUENCE: 77
catcatgagc ccggggtggc                                              20

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-3ac/ola biallelic
      polymorphism marker

<400> SEQUENCE: 78
```

```
tttctcttgg cttcctggtg cgt                                           23
```

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-3ac/ola biallelic
      polymorphism marker

<400> SEQUENCE: 79

```
accttctctt ggcttcctgg tgcgg                                         25
```

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence:PCR or
      ligation oligonucleotide primer for ctg2931-3ac/ola biallelic
      polymorphism marker

<400> SEQUENCE: 80

```
gccaaaggtg tcgtgccagg gctcca                                        26
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP1 biallelic polymorphism
      marker

<400> SEQUENCE: 81

```
atctgagaag gccctgctct                                               20
```

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP1 biallelic polymorphism
      marker

<400> SEQUENCE: 82

```
atctgagaag gccctgctcc                                               20
```

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for SNP1 biallelic polymorphism
      marker

<400> SEQUENCE: 83

```
cccacactta gccttgatg                                                19
```

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for Ctg22Ex1 biallelic -continued polymorphism marker

<400> SEQUENCE: 84
atgagttagc ccagcggag                                                19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for Ctg22Ex1 biallelic
      polymorphism marker

<400> SEQUENCE: 85
attgagagcc cttggagtg                                                19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for hb27G11F biallelic
      polymorphism marker

<400> SEQUENCE: 86
tgatttcgta agacaagtg                                                19

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:PCR or
      ligation oligonucleotide primer for hb27G11F biallelic
      polymorphism marker

<400> SEQUENCE: 87
agcaaattct aggagttatg                                               20

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence:PCR or
      ligation oligonucleotide primer for KIAA0849ex9 biallelic
      polymorphism marker

<400> SEQUENCE: 88
agctgagatg tccggatcg                                                19

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence:PCR or
      ligation oligonucleotide primer for KIAA0849ex9 biallelic
      polymorphism marker

<400> SEQUENCE: 89
agctgagatt ccggatca                                                 18

<210> SEQ ID NO 90
<211> LENGTH: 20
<212> TYPE: DNA

-continued

```
<213> ORGANISM: Artificial Sequence
<220> FEATURE:
<223> OTHER INFORMATION: Description of Artificial Sequence:PCR or
      ligation oligonucleotide primer for KIAA0849ex9 biallelic
      polymorphism marker

<400> SEQUENCE: 90
gtcctcttaa cttcccttcc                                                  20
```

GENES INVOLVED IN INTESTINAL INFLAMMATORY DISEASES AND USE THEREOF

CROSS-REFERENCES TO RELATED APPLICATIONS

This application claims priority to U.S. application Ser. No. 10/240,046 (allowed), filed Jan. 15, 2003, which application was a 371 National Stage application of PCT/FR01/00935, filed Mar. 27, 2001, which application claims priority to FR 0003832, filed Mar. 27, 2000, all of which are incorporated by reference in their entirety.

The present invention relates to genes involved in inflammatory and/or immune diseases and certain cancers, in particularly cryptogenetic inflammatory bowel diseases, and also to the proteins encoded by these genes. The present invention also relates to methods for diagnosing inflammatory diseases.

Cryptogenetic inflammatory bowel diseases (IBDs) are diseases characterized by an inflammation of the digestive tract, the cause of which is unknown. Depending on the location and the characteristics of the inflammation, two different nosological entities are distinguished: ulcerative colitis (UC) and Crohn's disease (CD). UC was described by S Wilkes in 1865, whereas the first case of regional ileitis was reported by Crohn in 1932. In reality, it is possible that these two diseases go back much further.

IBDs are chronic diseases which evolve throughout life and which affect approximately 1 to 2 individuals per 1000 inhabitants in western countries, which represents between 60000 and 100000 individuals suffering from these diseases in France. They are diseases which appear in young individuals (peak instance is in the third decade), progressing via attacks interspersed with remissions, with frequent complications such as undernutrition, retarded growth in children, bone demineralization and, in the end, malignant degeneration to colon cancer. No specific treatment exists. Conventional therapeutics make use of anti-inflammatories, of immunosuppressors and of surgery. All these therapeutic means are, themselves, a source of considerable iatrogenic morbidity. For all these reasons, IBDs appear to be a considerable public health problem.

The etiology of IBDs is currently unknown. Environmental factors are involved in the occurrence of the disease, as witnessed by the secular increase in incidence of the disease and the incomplete concordance in monozygous twins. The only environmental risk factors currently known are 1) tobacco, the role of which is harmful in CD and beneficial in UC, and 2) appendectomy which has a protective role for UC.

Genetic predisposition has been suspected for a long time due to the existence of ethnic and familial aggregation of these diseases. In fact, IBDs are more common in the Caucasian population, and in particular in the Jewish population of central Europe. Familial forms represent from 6 to 20% of IBD cases. They are particularly common when the disease begins early. However, it is studies in twins which have made it possible to confirm the genetic nature of these diseases. In fact, the concordance rate between twins for these diseases is greater in monozygous twins than in dizygous twins, which pleads strongly in favor of a hereditary component to IBDs, in particular to CD. In all probability, IBDs are complex genetic diseases involving several different genes, interacting with one another and with environmental factors. IBDs can therefore be classified within the context of multifactor diseases.

Two major strategies have been developed in order to demonstrate the IBD-susceptibility genes. The first is based on the analysis of genes which are candidates for physiopathological reasons. Thus, many genes have been proposed as potentially important for IBDs. They are often genes which have a role in inflammation and the immune response. Mention may be made of the HLA, TAP, TNF and MICA genes, lymphocyte T receptor, ICAM1, interleukin 1, CCR5, etc. Other genes participate in diverse functions, such as GAI2, motilin, MRAMP, HMLH1, etc. In reality, none of the various candidate genes studied has currently definitively proved itself to have a role in the occurrence of IBDs.

The recent development of human genome maps using highly polymorphic genetic markers has enabled geneticists to develop a nontargeted approach over the entire genome. This approach, also called reverse genetics or positional cloning, makes no hypothesis regarding the genes involved in the disease and attempts to discover them through systematic screening of the genome. The method most used for complex genetic diseases is based on studying identity by decendance of the affected individuals of the same family. This value is calculated for a large number (300-400) of polymorphism markers distributed evenly (every 10 cM) over the genome). In the case of excess identity between affected individuals, the marker(s) tested indicate(s) a region supposed to contain a gene for susceptibility to the disease. In the case of complex genetic diseases, since the model underlying the genetic predisposition (number of genes and relative importance of each of them) is unknown, the statistical methods to be used will have to be adjusted.

The present invention relates to the demonstration of the nucleic acid sequence of genes involved in IBDs, and other inflammatory diseases, and also the use of these nucleic acid sequences.

In the context of the present invention, preliminary studies by the inventors have already made it possible to locate a CD-susceptibility gene. Specifically, the inventors (Hugot et al., 1996) have shown that a CD-susceptibility gene is located in the pericentromeric region of chromosome 16 (FIG. 1). It was the first gene for susceptibility to a complex genetic disease located by positional cloning and satisfying the strict criteria proposed in the literature (Lander and Kruglyak, 1995). This gene was named IBM (for inflammatory bowel disease 1). Since then, other locations have been proposed by other authors, in particular on chromosomes 12, 1, 3, 6 and 7 (Satsangi et al., 1996; Cho et al., 1998). Although they have been located, it has currently not been possible to identify any of these IBD-susceptibility genes.

Some authors have not been able to replicate this location (Rioux et al., 1998). This is not, however, surprising in the case of complex genetic diseases in which genetic heterogeneity is probable.

It is interesting to note that, according to the same approach of positional cloning, locations have also been proposed on chromosome 16 for several immune and inflammatory diseases, such as ankylosing spondylarthritis, Blau's syndrome, psoriasis, etc. (Becker et al., 1998; Tromp et al., 1996). All these diseases may then share the same gene (or the same group of genes) located on chromosome 16.

A maximum of genetic linkage tests is virtually always located at the same position, in the region of D16S409 or D16S411, separated only by 2 cM. This result contradicts the considerable size (usually greater than 20 cM) of the confidence interval which can be attributed to the genetic location according to an approach using nonparametric linkage analyses.

Comparison of the statistical tests used in the studies by the inventors shows that the tests based on complete identity by decendance (Tz2) are better than the tests based on the mean of identity by decendance (Tz) (FIG. 1). Such a difference can be explained by a recessive effect of IBD1.

Several genes known to be in the pericentromeric region of chromosome 16, such as the interleukin 4 receptor, CD19, CD43 or CD11, appear to be good potential candidates for CD. Preliminary results do not however plead in favor of these genes being involved in CD.

In particular, the present invention provides not only the sequence of IBD1 gene, but also the partial sequence of another gene, called IBD1prox due to it being located in proximity to IBD, and demonstrated as reported in the examples below. These genes, the cDNA sequence of which corresponds, respectively, to SEQ ID No. 1 and SEQ ID No. 4, are therefore potentially involved in many inflammatory and/or immune diseases and also in cancers.

The peptide sequence expressed by the IBD1 and IBD1prox genes is represented by SEQ ID No. 2 and SEQ ID No. 5, respectively; the genomic sequence of these genes is represented by SEQ ID No. 3 and SEQ ID No. 6, respectively.

Thus, a subject of the present invention is a purified or isolated nucleic acid, characterized in that it comprises a nucleic acid sequence chosen from the following group of sequences:

a) SEQ ID No. 1, SEQ ID No. 3, SEQ ID No. 4 and SEQ ID No. 6;
b) the sequence of a fragment of at least 15 consecutive nucleotides of a sequence chosen from SEQ ID No. 1, SEQ ID No. 3, SEQ ID No. 4 or SEQ ID No. 6;
c) a nucleic acid sequence having a percentage identity of at least 80%, after optimal alignment, with a sequence defined in a) or b);
d) a nucleic acid sequence which hybridizes, under high stringency conditions, with a nucleic acid sequence defined in a) or b);
e) the complementary sequence or the RNA sequence corresponding to a sequence as defined in a), b), c) or d).

The nucleic acid sequence according to the invention defined in c) has a percentage identity of at least 80%, after optimal alignment, with a sequence as defined in a) or b) above, preferably 90%, most preferably 98%.

The terms "nucleic acid", "nucleic acid sequence", "polynucleotide", "oligonucleotide", "polynucleotide sequence" and "nucleotide sequence", terms which will be employed indifferently in the present description, are intended to denote a precise series of nucleotides, which may or may not be modified, making it possible to define a fragment or a region of a nucleic acid, which may or may not comprise unnatural nucleotides, and which may correspond equally to a double-stranded DNA, a single-stranded DNA and transcription products of said DNAs. Thus, the nucleic acid sequences according to the invention also encompass PNAs (Peptide Nucleic Acids), or the like.

It should be understood that the present invention does not relate to the nucleotide sequences in their natural chromosomal environment, that is to say in the natural state. They are sequences which have been isolated and/or purified, that is to say they have been taken directly or indirectly, for example by copying, their environment having been at least partially modified. Thus, nucleic acids obtained by chemical synthesis are also intended to be denoted.

For the purpose of the present invention, the term "percentage identity" between two nucleic acid or amino acid sequences is intended to denote a percentage of nucleotides or of amino acid residues which are identical between the two sequences to be compared, obtained after the best alignment, this percentage being purely statistical and the differences between the two sequences being distributed randomly and over their entire length. The term "best alignment" or "optimal alignment" is intended to denote the alignment for which the percentage identity determined as below is highest. Sequence comparisons between two nucleic acid or amino acid sequences are conventionally carried out by comparing these sequences after having aligned them optimally, said comparison being carried out by segment or by "window of comparison" so as to identify and compare local regions of sequence similarity. The optimal alignment of the sequences for the comparison may be carried out, besides manually, by means of the local homology algorithm of Smith and Waterman (1981), by means of the local homology algorithm of Neddleman and Wunsch (1970), by means of the similarity search method of Pearson and Lipman (1988), by means of computer programs using these algorithms (GAP, BESTFIT, BLAST P, BLAST N, FASTA and TFASTA in the Wisconsin Genetics Software Package, Genetics Computer Group, 575 Science Dr., Madison, Wis.). In order to obtain the optimal alignment, the BLAST program is preferably used, with the BLOSUM 62 matrix. The PAM or PAM250 matrices may also be used.

The percentage identity between two nucleic acid or amino acid sequences is determined by comparing these two sequences aligned optimally, the nucleic acid or amino acid sequence to be compared possibly comprising additions or deletions with respect to the reference sequence for optimal alignment between these two sequences. The percentage identity is calculated by determining the number of identical positions for which the nucleotide or the amino acid residue is identical between the two sequences, dividing this number of identical positions by the total number of positions compared and multiplying the resultant number by 100 so as to obtain the percentage identity between these two sequences.

The expression "nucleic acid sequences having a percentage identity of at least 80%, preferably 90%, more preferably 98%, after optimal alignment with a reference sequence" is intended to denote the nucleic acid sequences which, compared to the reference nucleic acid sequence, have certain modifications, such as in particular a deletion, a truncation, an extension, a chimeric fusion and/or a substitution, in particular of the point type, and the nucleic acid sequence of which exhibits at least 80%, preferably 90%, more preferably 98%, identity, after optimal alignment, with the reference nucleic acid sequence. They are preferably sequences whose complementary sequences are capable of hybridizing specifically with the sequence SEQ ID No. 1 or SEQ ID No. 4 of the invention. Preferably, the specific or high stringency hybridization conditions will be such that they ensure at least 80%, preferably 90%, more preferably 98%, identity, after optimal alignment, between one of the two sequences and the sequence complementary to the other.

Hybridization under high stringency conditions means that the conditions of temperature and of ionic strength are chosen such that they allow the hybridization between two complementary DNA fragments to be maintained. By way of illustration, high stringency conditions for the hybridization step for the purposes of defining the polynucleotide fragments described above are advantageously as follows.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a solution of 0.15 M NaCl+0.015 M sodium citrate), 50% of formamide, 7% of sodium dodecyl sulfate (SDS), 10×Denhardt's, 5% of dextran sulfate and 1% of salmon sperm DNA; (2) hybridization per se for 20 hours at a temperature which depends on the length of the probe (i.e.: 42° C. for a probe>100 nucleotides in length), followed by 2 washes of 20 minutes at 20° C. in 2×SSC+2% SDS and 1 wash of 20 minutes at 20° C. in 0.1×SSC+0.1% SDS. The final wash is carried out in 0.1×SSC+0.1% SDS for 30 minutes at 60° C. for a probe>100 nucleotides in length. The high stringency hybridization conditions described above for a polynucleotide of defined length may be adjusted by those skilled in the art for longer or shorter oligonucleotides, according to the teaching of Sambrook et al., 1989.

Among the nucleic acid sequences having a percentage identity of at least 80%, preferably 90%, more preferably 98%, after optimal alignment, with the sequence according to the invention, preference is also given to the variant nucleic acid sequences of SEQ ID No. 1 or of SEQ ID No. 4, or of fragments thereof, that is to say all the nucleic acid sequences corresponding to allelic variants, that is to say individual variations of the sequence SEQ ID No. 1 or SEQ ID No. 4. These natural mutated sequences correspond to polymorphisms present in mammals, in particular in humans and, in particular, to polymorphisms which may lead to the occurrence of a pathological condition. Preferably, the present invention relates to the variant nucleic acid sequences in which the mutations lead to a modification of the amino acid sequence of the polypeptide, or of fragments thereof, encoded by the normal sequence of SEQ ID No. 1 or SEQ ID No. 4.

The expression "variant nucleic acid sequence" is also intended to denote any RNA or cDNA resulting from a mutation and/or variation of a splice site of the genomic nucleic acid sequence the cDNA of which has the sequence SEQ ID No. 1 or SEQ ID No. 4.

The invention preferably relates to a purified or isolated nucleic acid according to the present invention, characterized in that it comprises or consists of one of the sequences SEQ ID No. 1 or SEQ ID No. 4, of the sequences complementary thereto, or of the RNA sequences corresponding to SEQ ID No. 1 or SEQ ID No. 4.

The probes or primers, characterized in that they comprise a sequence of a nucleic acid according to the invention, are also part of the invention.

Thus, the present invention also relates to the primers or the probes according to the invention which may make it possible in particular to demonstrate or to distinguish the variant nucleic acid sequences, or to identify the genomic sequence of the genes the cDNA of which is represented by SEQ ID No. 1 or SEQ ID No. 4, in particular using an amplification method such as the PCR method or a related method.

The invention also relates to the use of a nucleic acid sequence according to the invention, as a probe or primer, for detecting, identifying, assaying or amplifying a nucleic acid sequence.

According to the invention, the polynucleotides which can be used as a probe or as a primer in methods for detecting, identifying, assaying or amplifying a nucleic acid sequence are a minimum of 15 bases, preferably 20 bases, or better still 25 to 30 bases in length.

The probes and primers according to the invention may be labeled directly or indirectly with a radioactive or nonradioactive compound using methods well known to those skilled in the art, in order to obtain a detectable and/or quantifiable signal.

The polynucleotide sequences according to the invention which are unlabeled can be used directly as a probe or primer.

The sequences are generally labeled so as to obtain sequences which can be used in many applications. The primers or the probes according to the invention are labeled with radioactive elements or with nonradio-active molecules.

Among the radioactive isotopes used, mention may be made of $^{32}P$, $^{33}P$, $^{35}S$, $^{3}H$ or $^{125}I$. The nonradioactive entities are selected from ligands such as biotin, avidin, streptavidin or dioxygenin, haptens, dyes and luminescent agents, such as radioluminescent, chemiluminescent, bioluminescent, fluorescent or phosphorescent agents.

The polynucleotides according to the invention may thus be used as a primer and/or probe in methods using in particular the PCR (polymerase chain reaction) technique (Rolfs et al., 1991). This technique requires choosing pairs of oligonucleotide primers bordering the fragment which must be amplified. Reference may, for example, be made to the technique described in U.S. Pat. No. 4,683,202. The amplified fragments can be identified, for example after agarose or polyacrylamide gel electrophoresis, or after a chromatographic technique such as gel filtration or ion exchange chromatography, and then sequenced. The specificity of the amplification can be controlled using, as primers, the nucleotide sequences of polynucleotides of the invention and, as matrices, plasmids containing these sequences or else the derived amplification products. The amplified nucleotide fragments may be used as reagents in hybridization reactions in order to demonstrate the presence, in a biological sample, of a target nucleic acid of sequence complementary to that of said amplified nucleotide fragments.

The invention is also directed toward the nucleic acids which can be obtained by amplification using primers according to the invention.

Other techniques for amplifying the target nucleic acid may advantageously be employed as an alternative to PCR (PCR-like) using a pair of primers of nucleotide sequences according to the invention. The term "PCR-like" is intended to denote all the methods using direct or indirect reproductions of nucleic acid sequences, or else in which the labeling systems have been amplified; these techniques are, of course, known. In general, they involve amplifying the DNA with a polymerase; when the sample of origin is an RNA a reverse transcription should be carried out beforehand. A large number of methods currently exist for this amplification, such as, for example, the SDA (strand displacement amplification) technique (Walker et al., 1992), the TAS (transcription-based amplification system) technique described by Kwoh et al. (1989), the 3SR (self-sustained sequence replication) technique described by Guatelli et al. (1990), the NASBA (nucleic acid sequence based amplification) technique described by Kievitis et al. (1991), the TMA (transcription mediated amplification) technique, the LCR (ligase chain reaction) technique described by Landegren et al. (1988), the RCR (repair chain reaction) technique described by Segev (1992), the CPR (cycling probe reaction) technique described by Duck et al. (1990), and the Q-beta-replicase amplification technique described by Miele et al. (1983). Some of these techniques have since been improved.

When the target polynucleotide to be detected is an mRNA, an enzyme of the reverse transcriptase type is advantageously used, prior to carrying out an amplification reaction using the primers according to the invention or to carrying out a method of detection using the probes of the invention, in order to obtain a cDNA from the mRNA contained in the biological sample. The cDNA obtained will then serve as a target for the primers or the probes used in the amplification or detection method according to the invention.

The probe hybridization technique may be carried out in many ways (Matthews et al., 1988). The most general method consists in immobilizing the nucleic acid extracted from the cells of various tissues or from cells in culture, on a support (such as nitrocellulose, nylon or polystyrene), and in incubating the immobilized target nucleic acid with the probe, under well-defined conditions. After hybridization, the excess probe is removed and the hybrid molecules formed are detected using the appropriate method (measuring the radioactivity, the fluorescence or the enzymatic activity linked to the probe).

According to another embodiment of the nucleic acid probes according to the invention, the latter may be used as capture probes. In this case, a probe, termed "capture probe", is immobilized on a support and is used to capture, by specific hybridization, the target nucleic acid obtained from the biological sample to be tested, and the target nucleic acid is then detected using a second probe, termed "detection probe", labeled with a readily detectable element.

Among the advantageous nucleic acid fragments, mention should thus be made in particular of antisense oligonucleotides, i.e. oligonucleotides, the structure of which ensures, by hybridization with the target sequence, inhibition of expression of the corresponding product. Mention should also be made of sense oligonucleotides, which, by interacting with proteins involved in regulating the expression of the corresponding product, will induce either inhibition or activation of this expression.

In both cases (sense and antisense), the oligonucleotides of the invention may be used in vitro and in vivo.

The present invention also relates to an isolated polypeptide, characterized in that it comprises a polypeptide chosen from:
a) a polypeptide of sequence SEQ ID No. 2 or SEQ ID No. 5;
b) a variant polypeptide of a polypeptide of sequence defined in a);
c) a polypeptide homologous to a polypeptide defined in a) or b), comprising at least 80% identity with said polypeptide of a);
d) a fragment of at least 15 consecutive amino acids of a polypeptide defined in a), b) or c);
e) a biologically active fragment of a polypeptide defined in a), b) or c).

For the purpose of the present invention, the term "polypeptide" is intended to denote proteins or peptides.

The expression "biologically active fragment" is intended to mean a fragment having the same biological activity as the peptide fragment from which it is deduced, preferably within the same order of magnitude (to within a factor of 10). Thus, the examples show that the IBD1 protein (SEQ ID No. 2) has a potential role in apoptosis phenomena. A biologically active fragment of the IBD1 protein therefore consists of a polypeptide derived from SEQ ID No. 2, also having a role in apoptosis. The examples below propose biological functions for the IBD1 and IBD1prox proteins, as a function of the peptide domains of these proteins, and thus allow those skilled in the art to identify the biologically active fragments.

Preferably, a polypeptide according to the invention is a polypeptide consisting of the sequence SEQ ID No. 2 (corresponding to the protein encoded by the IBD1 gene) or of the sequence SEQ ID No. 5 (corresponding to the protein encoded by IBD1prox) or of a sequence having at least 80% identity with SEQ ID No. 2 or SEQ ID No. 5 after optimal alignment.

The sequence of the polypeptide has a percentage identity of at least 80%, after optimal alignment, with the sequence SEQ ID No. 2 or SEQ ID No. 5, preferably 90%, more preferably 98%.

The expression "polypeptide, the amino acid sequence of which has a percentage identity of at least 80%, preferably 90%, more preferably 98%, after optimal alignment, with a reference sequence" is intended to denote the polypeptides having certain modifications compared to the reference polypeptide, such as in particular one or more deletions and/or truncations, an extension, a chimeric fusion and/or one or more substitutions.

Among the polypeptides, the amino acid sequence of which has a percentage identity of at least 80%, preferably 90%, more preferably 98%, after optimal alignment, with the sequence SEQ ID No. 2 or SEQ ID No. 5 or with a fragment thereof according to the invention, preference is given to the variant polypeptides encoded by the variant nucleic acid sequences as defined previously, in particular the polypeptides, the amino acid sequence of which has at least one mutation corresponding in particular to a truncation, deletion, substitution and/or addition of at least one amino acid residue compared with the sequence SEQ ID No. 2 or SEQ ID No. 5 or with a fragment thereof, more preferably the variant polypeptides having a mutation associated with the pathological condition.

The present invention also relates to the cloning and/or expression vectors comprising a nucleic acid or encoding a polypeptide according to the invention. Such a vector may also contain the elements required for the expression and, optionally, the secretion of the polypeptide in a host cell. Such a host cell is also a subject of the invention.

The vectors characterized in that they comprise a promoter and/or regulator sequence according to the invention are also part of the invention.

Said vectors preferably comprise a promoter, translation initiation and termination signals, and also regions suitable for regulating transcription. It must be possible for them to be maintained stably in the cell and they may optionally contain particular signals specifying secretion of the translated protein.

These various control signals are chosen as a function of the cellular host used. To this effect, the nucleic acid sequences according to the invention may be inserted into vectors which replicate autonomously in the chosen host, or vectors which integrate in the chosen host.

Among the systems which replicate autonomously, use is preferably made, depending on the host cell, of systems of the plasmid or viral type, the viral vectors possibly being in particular adenoviruses (Perricaudet et al., 1992), retroviruses, lentiviruses, poxviruses or herpesviruses (Epstein et al., 1992). Those skilled in the art are aware of the technology which can be used for each of these systems.

When integration of the sequence into the chromosomes of the host cell is desired, use may be made, for example, of systems of the plasmid or viral type; such viruses are, for example, retroviruses (Temin, 1986), or AAVs (Carter, 1993).

Among the nonviral vectors, preference is given to naked polynucleotides such as naked DNA or naked RNA according to the technology developed by the company VICAL, bacterial artificial chromosomes (BACs), yeast artificial chromosomes (YACs) for expression in yeast, mouse artificial chromosomes (MACs) for expression in murine cells and, preferably, human artificial chromosomes (HACs) for expression in human cells.

Such vectors are prepared according to the methods commonly used by those skilled in the art, and the clones resulting therefrom can be introduced into a suitable host using standard methods, such as, for example, lipofection, electroporation, heat shock, transformation after chemical permeabilization of the membrane, or cell fusion.

The invention also comprises host cells, in particular the eukaryotic and prokaryotic cells, transformed with the vectors according to the invention, and also the transgenic animals, preferably the mammals, except humans, comprising one of said transformed cells according to the invention.

These animals may be used as models, for studying the etiology of inflammatory and/or immune diseases, in particular of the inflammatory diseases of the digestive tract, or for studying cancers.

Among the cells which can be used for the purpose of the present invention, mention may be made of bacterial cells (Olins and Lee, 1993), but also yeast cells (Buckholz, 1993) as well as animal cells, in particular mammalian cell cultures (Edwards and Aruffo, 1993), and especially Chinese hamster ovary (CHO) cells. Mention may also be made of insect cells in which it is possible to use methods employing, for example, baculo viruses (Luckow, 1993). A preferred cellular host for expressing the proteins of the invention consists of COS cells.

Among the mammals according to the invention, animals such as rodents, in particular mice, rats or rabbits, expressing a polypeptide according to the invention are preferred.

Among the mammals according to the invention, preference is also given to animals such as mice, rats or rabbits, characterized in that the gene encoding the protein of sequence SEQ ID No. 2 or SEQ ID No. 5, or the sequence of which is encoded by the homologous gene in these animals, is not functional, has been knocked out or has at least one mutation.

These transgenic animals are obtained, for example, by homologous recombination on embryonic stem cells, transfer of these stem cells to embryos, selection of the chimeras affected in the reproductive lines, and growth of said chimeras.

The transgenic animals according to the invention may thus overexpress the gene encoding the protein according to the invention, or their homologous gene, or express said gene into which a mutation is introduced. These transgenic animals, in particular mice, are obtained, for example, by transfection of a copy of this gene under the control of a promoter which is strong and ubiquitous, or selective for a tissue type, or after viral transcription.

Alternatively, the transgenic animals according to the invention may be made deficient for the gene encoding one of the polypeptides of sequence SEQ ID No. 2 or SEQ ID No. 5, or their homologous genes, by inactivation using the LOXP/CRE recombinase system (Rohlmann et al., 1996) or any other system for inactivating the expression of this gene.

The cells and mammals according to the invention can be used in a method for producing a polypeptide according to the invention, as described below, and may also be used as a model for analysis.

The cells or mammals transformed as described above can also be used as models in order to study the interactions between the polypeptides according to the invention, and the chemical or protein compounds involved directly or indirectly in the activities of the polypeptides according to the invention, this being in order to study the various mechanisms and interactions involved.

They may in particular be used for selecting products which interact with the polypeptides according to the invention, in particular the protein of sequence SEQ ID No. 2 or SEQ ID No. 5 or variants thereof according to the invention, as a cofactor or as an inhibitor, in particular a competitive inhibitor, or which have an agonist or antagonist activity with respect to the activity of the polypeptides according to the invention. Preferably, said transformed cells or transgenic animals are used as a model in particular for selecting products for combating pathological conditions associated with abnormal expression of this gene.

The invention also relates to the use of a cell, of a mammal or of a polypeptide according to the invention, for screening chemical or biochemical compounds which may interact directly or indirectly with the polypeptides according to the invention, and/or which are capable of modulating the expression or the activity of these polypeptides.

Similarly, the invention also relates to a method for screening compounds capable of interacting, in vitro or in vivo, with a nucleic acid according to the invention, using a nucleic acid, a cell or a mammal according to the invention, and detecting the formation of a complex between the candidate compounds and the nucleic acid according to the invention.

The compounds thus selected are also subjects of the invention.

The invention also relates to the use of a nucleic acid sequence according to the invention, for synthesizing recombinant polypeptides.

The method for producing a polypeptide of the invention in recombinant form, which is itself included in the present invention, is characterized in that the transformed cells, in particular the cells or mammals of the present invention, are cultured under conditions which allow the expression of a recombinant polypeptide encoded by a nucleic acid sequence according to the invention, and in that said recombinant polypeptide is recovered.

The recombinant polypeptides, characterized in that they can be obtained using said method of production, are also part of the invention.

The recombinant polypeptides obtained as indicated above can be in both glycosylated and nonglycosylated form, and may or may not have the natural tertiary structure.

The sequences of the recombinant polypeptides may also be modified in order to improve their solubility, in particular in aqueous solvents.

Such modifications are known to those skilled in the art, such as, for example, deletion of hydrophobic domains or substitution of hydrophobic amino acids with hydrophilic amino acids.

These polypeptides may be produced using the nucleic acid sequences defined above, according to the techniques for producing recombinant polypeptides known to those skilled in the art. In this case, the nucleic acid sequence used is placed under the control of signals which allow its expression in a cellular host.

An effective system for producing a recombinant polypeptide requires having a vector and a host cell according to the invention.

These cells can be obtained by introducing into host cells a nucleotide sequence inserted into a vector as defined above, and then culturing said cells under conditions which allow the replication and/or expression of the transfected nucleotide sequence.

The methods used for purifying a recombinant polypeptide are known to those skilled in the art. The recombinant polypeptide may be purified from cell lysates and extracts or from the culture medium supernatant, by methods used individually or in combination, such as fractionation, chromatography methods, immunoaffinity techniques using specific monoclonal or polyclonal antibodies, etc.

The polypeptides according to the present invention can also be obtained by chemical synthesis using one of the many known forms of peptide synthesis, for example techniques using solid phases (see in particular Stewart et al., 1984) or techniques using partial solid phases, by fragment condensation or by conventional synthesis in solution.

The polypeptides obtained by chemical synthesis and which may comprise corresponding unnatural amino acids are also included in the invention.

The mono- or polyclonal antibodies, or fragments thereof, chimeric antibodies or immunoconjugates, characterized in that they are capable of specifically recognizing a polypeptide according to the invention, are part of the invention.

Specific polyclonal antibodies may be obtained from a serum of an animal immunized against the polypeptides according to the invention, in particular produced by genetic recombination or by peptide synthesis, according to the usual procedures.

The advantage of antibodies which specifically recognize certain polypeptides, variants or immunogenic fragments thereof according to the invention is in particular noted.

The mono- or polyclonal antibodies, or fragments thereof, chimeric antibodies or immunoconjugates characterized in that they are capable of specifically recognizing the polypeptides of sequence SEQ ID No. 2 or SEQ ID No. 5 are particularly preferred.

The specific monoclonal antibodies may be obtained according to the conventional method of hybridoma culture described by Köhler and Milstein (1975).

The antibodies according to the invention are, for example, chimeric antibodies, humanized antibodies, or Fab or $F(ab')_2$ fragments. They may also be in the form of immunoconjugates or of labeled antibodies, in order to obtain a detectable and/or quantifiable signal.

The invention also relates to methods for detecting and/or purifying a polypeptide according to the invention, characterized in that they use an antibody according to the invention.

The invention also comprises purified polypeptides, characterized in that they are obtained using a method according to the invention.

Moreover, besides their use for purifying the polypeptides, the antibodies of the invention, in particular the monoclonal antibodies, may also be used for detecting these polypeptides in a biological sample.

They thus constitute a means for the immunocytochemical or immunohistochemical analysis of the expression of the polypeptides according to the invention, in particular the polypeptides of sequence SEQ ID No. 2 or SEQ ID No. 5, or a variant thereof, on specific tissue sections, for example using immunofluorescence, gold labeling and/or enzymatic immunoconjugates.

They may in particular make it possible to demonstrate abnormal expression of these polypeptides in the biological specimens or tissues.

More generally, the antibodies of the invention may advantageously be used in any situation where the expression of a polypeptide according to the invention, normal or mutated, must be observed.

Thus, a method for detecting a polypeptide according to the invention, in a biological sample, comprising the steps of bringing the biological sample into contact with an antibody according to the invention and demonstrating the antigen-antibody complex formed, is also a subject of the invention, as is a kit for carrying out such a method. Such a kit in particular contains:
- a) a monoclonal or polyclonal antibody according to the invention;
- b) optionally, reagents for constituting a medium suitable for the immunoreaction;
- c) the reagents for detecting the antigen-antibody complex produced during the immunoreaction.

The antibodies according to the invention may also be used in the treatment of an inflammatory and/or immune disease, or of a cancer, in humans, when abnormal expression of the IBD1 gene or of the IBD1prox gene is observed. Abnormal expression means overexpression or the expression of a mutated protein.

These antibodies may be obtained directly from human serum, or may be obtained from animals immunized with polypeptides according to the invention, and then "humanized", and may be used as such or in the preparation of a medicinal product intended for the treatment of the above-mentioned diseases.

The methods for determining an allelic variability, a mutation, a deletion, a loss of heterozygocity or any genetic abnormability of the gene according to the invention, characterized in that they use a nucleic acid sequence, a polypeptide or an antibody according to the invention, are also part of the invention.

The invention in fact provides the sequence of the IBD1 and IBD1prox genes involved in inflammatory and/or immune diseases, and in particular IBDs. One of the teachings of the invention is to specify the mutations, in these nucleic acid or polypeptide sequences, which are associated with a phenotype corresponding to one of these inflammatory and/or immune diseases.

These mutations can be detected directly by analysis of the nucleic acid and of the sequences according to the invention (genomic DNA, RNA or cDNA), but also via the polypeptides according to the invention. In particular, the use of an antibody according to the invention which recognizes an epitope bearing a mutation makes it possible to distinguish between a "healthy" protein and a protein "associated with a pathological condition".

Thus, the study of the IBD1 gene in various inflammatory and/or immune human diseases thus shows that sequence variants of this gene exist in Crohn's disease, ulcerative colitis and Blau's syndrome, as demonstrated by the examples. These sequence variations result in considerable variations in the deduced protein sequence. In fact, they are either located on very conserved sites of the protein in important functional domains, or they result in the synthesis of a truncated protein. It is therefore extremely probable that these deleterious modifications lead to a modification of the function of the protein and therefore have a causal effect in the occurrence of these diseases.

The variety of diseases in which these mutations are observed suggests that the IBD1 gene is potentially important in many inflammatory and/or immune diseases. This result should be compared with the fact that the pericentromeric region of chromosome 16 has been described as containing genes for susceptibility to various human diseases, such as ankylosing spondylarthritis or psoriatic arthropathy. It may therefore be considered that IBD1 has an important role in a large number of inflammatory and/or immune diseases.

In particular, IBD1 can be associated with granulomatous inflammatory diseases. Blau's syndrome and CD are in fact diseases which are part of this family. It is therefore hoped that variations in the IBD1 gene will be found for the other diseases of the same family (sarcoidosis, Behcet's disease, etc.).

In addition, the involvement of IBD1 in the cellular pathways leading to apoptosis raises the question of its possible carcinogenic role. In fact, it is expected that a dysregulation of IBD1 may result in a predisposition to cancer. This hypothesis is supported by the fact that a predisposition to colon cancer exists in inflammatory bowel diseases. IBD1 may in part explain this susceptibility to cancer and define new carcinogenic pathways.

The precise description of the mutations which can be observed in the IBD1 gene thus makes it possible to lay down the foundations of a molecular diagnosis for the inflammatory or immune diseases in which this role is demonstrated. Such an approach, based on searching for mutations in the gene, will make it possible to contribute to the diagnosis of these diseases and possibly to reduce the extent of certain additional examinations which are invasive or expensive. The invention lays down the foundations of such a molecular diagnosis based on searching for mutations in IBD1.

The molecular diagnosis of inflammatory diseases should also make it possible to improve the nosological classification of these diseases and to more clearly define subgroups of particular diseases by their clinical characteristics, the progressive nature of the disease or the response to certain treatments. By way of example, the dismantling of the existing mutations may thus make it possible to classify the currently undetermined forms of colitis which represent more than 10% of inflammatory bowel diseases. Such an approach will make it possible to propose an early treatment suitable for each patient. In general, such an approach makes it possible to hope that it will eventually be possible to define an individualized treatment for the disease, depending on the genetic area of each disease, including curative and preventive measures.

In particular, preference is given to a method of diagnosis and/or of prognostic assessment of an inflammatory disease or of a cancer, characterized in that the presence of at least one mutation and/or a deleterious modification of expression of the gene corresponding to SEQ ID No. 1 or SEQ ID No. 4 is determined, using a biological specimen from a patient, by analyzing all or part of a nucleic acid sequence corresponding to said gene. The genes SEQ ID No. 3 or SEQ ID No. 6 may also be studied.

This method of diagnosis and/or of prognostic assessment may be used preventively (a study of predisposition to inflammatory diseases or to cancer), or in order to serve in establishing and/or confirming a clinical condition in a patient.

Preferably, the inflammatory disease is an inflammatory disease of the digestive tract, and the cancer is a cancer of the digestive tract (small intestine or colon).

The teaching of the invention in fact makes it possible to determine the mutations which exhibit a linkage disequilibrium with inflammatory diseases of the digestive tract, and which are therefore associated with such diseases.

The analysis may be carried out by sequencing all or part of the gene, or by other methods known to those skilled in the art. Methods based on PCR, for example PCR-SSCP, which makes it possible to detect point mutations, may in particular be used.

The analysis may also be carried out by attaching a probe according to the invention, corresponding to one of the sequences SEQ ID No. 1, 3, 4 or 6, to a DNA chip, and hybridization on these microplates. A DNA chip containing a sequence according to the invention is also one of the subjects of the invention.

Similarly, a protein chip containing an amino acid sequence according to the invention is also a subject of the invention. Such a protein chip makes it possible to study the interactions between the polypeptides according to the invention and other proteins or chemical compounds, and may thus be useful for screening compounds which interact with the polypeptides according to the invention. The protein chips according to the invention may also be used to detect the presence of antibodies directed against the polypeptides according to the invention in the serum of patients. A protein chip containing an antibody according to the invention may also be used.

Those skilled in the art are also able to carry out techniques for studying the deleterious modification of the expression of a gene, for example by studying the mRNA (in particular by Northern blotting or with RT-PCR experiments, with probes or primers according to the invention), or the protein expressed, in particular by Western blotting, using antibodies according to the invention.

The gene tested is preferably the gene of sequence SEQ ID No. 1, the inflammatory disease for which the intention is to predict susceptibility being a disease of the digestive tract, in particular Crohn's disease or ulcerative colitis. If the intention is to detect a cancer, it is preferably colon cancer.

The invention also relates to methods for obtaining an allele of the IBD1 gene, associated with a detectable phenotype, comprising the following steps:
  a) obtaining a nucleic acid sample from an individual expressing said detectable phenotype;
  b) bringing said nucleic acid sample into contact with an agent capable of specifically detecting a nucleic acid encoding the IBD1 protein;
  c) isolating said nucleic acid encoding the IBD1 protein.

Such a method may be followed by a step of sequencing all or part of the nucleic acid encoding the IBD1 protein, which makes it possible to predict susceptibility to inflammatory disease or of a cancer.

The agent capable of specifically detecting a nucleic acid encoding the IBD1 protein is advantageously an oligonucleotide probe according to the invention, which may be made up of DNA, RNA or PNA, which may or may not be modified. The modifications may include radioactive or fluorescent labeling, or may be due to modifications in the bonds between the bases (phosphorothioates or methyl phosphonates, for example). Those skilled in the art are aware of the protocols for isolating a specific DNA sequence. Step b) of the method described above may also be an amplification step as described above.

The invention also relates to a method for detecting and/or assaying a nucleic acid according to the invention, in a biological sample, comprising the following steps of bringing a probe according to the invention into contact with a biological sample, and detecting and/or assaying the hybrid formed between said polynucleotide and the nucleic acid of the biological sample.

Those skilled in the art are capable of carrying out such a method, and may in particular use a kit of reagents, comprising:
  a) a polynucleotide according to the invention, used as a probe;
  b) the reagents required for carrying out a hybridization reaction between said probe and the nucleic acid of the biological sample;
  c) the reagents required for detecting and/or assaying the hybrid formed between said probe and the nucleic acid of the biological sample;
which is also a subject of the invention.

Such a kit may also contain positive or negative controls in order to ensure the quality of the results obtained.

However, in order to detect and/or assay a nucleic acid according to the invention, those skilled in the art may also perform an amplification step using primers chosen from the sequences according to the invention.

Finally, the invention also relates to the compounds chosen from a nucleic acid, a polypeptide, a vector, a cell or an antibody according to the invention, or the compounds obtained using the screening methods according to the invention, as a medicinal product, in particular for preventing and/or treating an inflammatory and/or immune disease, or a cancer, associated with the presence of at least one mutation of the gene corresponding to SEQ ID No. 1 or SEQ ID No. 4, preferably an inflammatory disease of the digestive tract, in particular Crohn's disease or ulcerative colitis.

The following examples make it possible to understand more clearly the advantages of the invention, and should not be considered to limit the scope of the invention.

A: The translation produced deduced from the cDNA sequence of the IBD1 candidate gene is identical to that of NOD2 (Ogura et al., 2000). The polypeptide contains 2 CARD domains (CAspase Recruitment Domains), a nucleotide-binding domain (NBD) and 10 repeats of 27 amino acids, leucine-rich motifs (LRR). The consensus sequence of the ATP/GTP-binding site of the motif A (P loop) of the NBD is indicated with a black circle. The sequence changes encoded by the three main variants associated with CD are SNP 8 (R675W), SNP 12 (G881R) and SNP 13 (frame shift 980). The frame shift changes a leucine codon to a proline codon at position 980, which is immediately followed by a stop codon.

B: Rare missense variants of NOD2 in 457 CD patients, 159 UC patients and 103 unaffected, unrelated individuals. The positions of the rare missense variants are indicated for the three groups. The scale on the left indicates the number of each variant identified in the groups under investigation and that on the right measures the frequency of the mutation. The allelic frequencies of the polymorphism V928I was not significantly different (0.92:0.08) in the three groups and the corresponding genotypes were in Hardy-Weinberg equilibrium.

EXAMPLES

Example 1

Fine Location of IBD1

Figure 1:
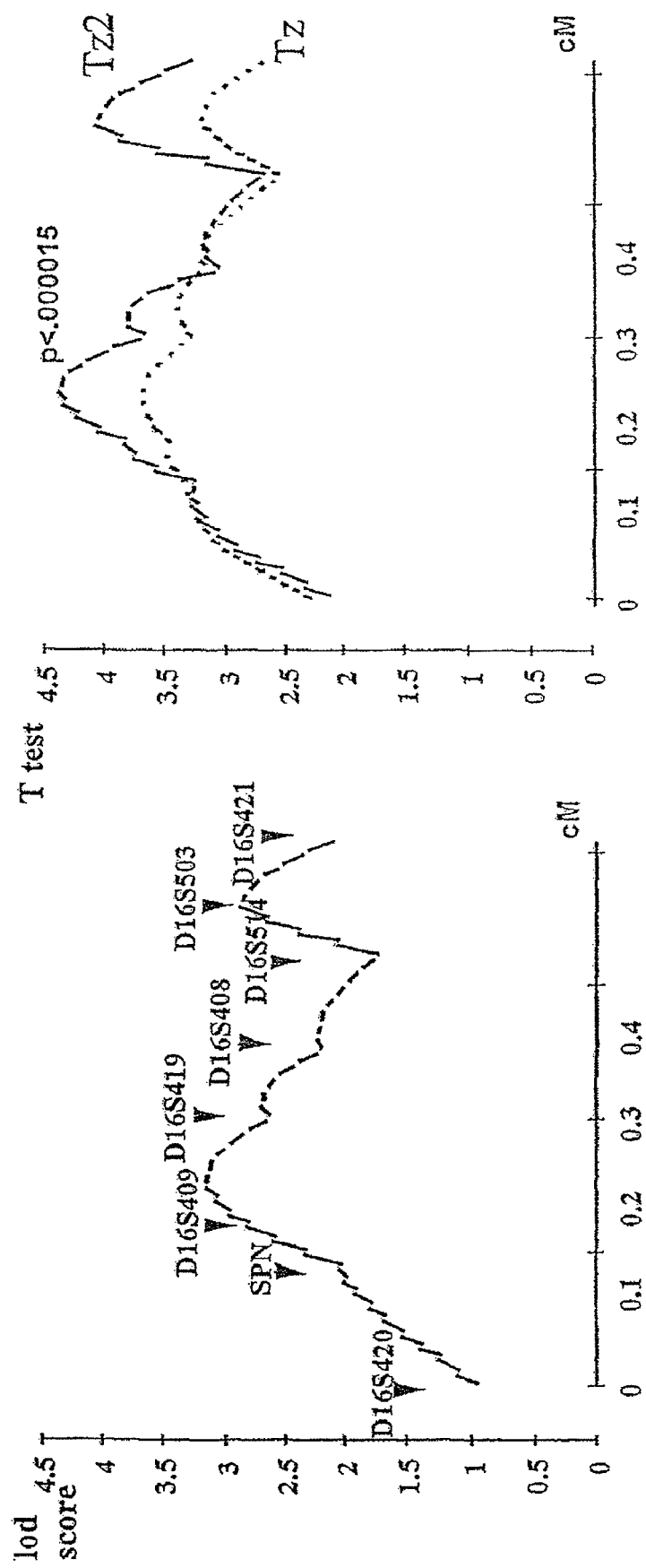
FIG. 1: Nonparametric genetic linkage tests for Crohn's disease in the pericentromeric region of chromosome 16 (according to Hugot et al., 1996). Multipoint linkage analysis based on identity by decendance for the markers of the pericentromeric region of chromosome 16. The genetic distances between markers were estimated using the CRIMAP program. The lod score (MAPMAKER/SIBS) is indicated on the left-hand figure. Two pseudoprobability tests were developed and reported on the right-hand figure. The first (Tz) is analogous to the test of the means. The second (Tz2) is analogous to the test of the proportion of affected pairs sharing two alleles.

The first step toward identifying the IBD1 gene was to reduce the size of the genetic region of interest, initially centered on the marker D16S411 located between D16S409 and D16S419 (Hugot et al., 1996 and FIG. 1). A group of close markers (high resolution genetic map) was used in order to more clearly specify the genetic region, and made it possible to complete the genetic linkage analyses and to search for a genetic linkage disequilibrium with the disease.

The study related to 78 families comprising at least 2 relatives suffering from CD, which corresponded to 119 affected pairs. The families comprising sick individuals suffering from UC were excluded from the study.

Twenty-six genetic polymorphism markers of the microsatellite type were studied. These markers together made up a high resolution map with an average distance between markers of the order of 1 cM in the genetic region of interest. The characteristics of the markers studied are given in table 1.

TABLE 1

Polymorphic markers of the microsatellite type used for the fine location of IBD1

| Name of polymorphism marker | Cumulative distance (cM) | PCR primers |
|---|---|---|
| D16S3120 | 0 | SEQ ID No. 7 |
| (AFM326vc5) | | SEQ ID No. 8 |
| D16S298 | 2.9 | SEQ ID No. 9 |
| (AFMa189wg5) | | SEQ ID No. 10 |
| D16S299 | 3.4 | SEQ ID No. 11 |
| | | SEQ ID No. 12 |
| SPN | 3.9 | SEQ ID No. 13 |
| | | SEQ ID No. 14 |
| D16S383 | 4.3 | SEQ ID No. 15 |
| | | SEQ ID No. 16 |
| D16S753 | 4.9 | SEQ ID No. 17 |
| (GGAA3G05) | | SEQ ID No. 18 |
| D16S3044 | 5.8 | SEQ ID No. 19 |
| (AFMa222za9) | | SEQ ID No. 20 |
| D16S409 | 5.8 | SEQ ID No. 21 |
| (AFM161xa1) | | SEQ ID No. 22 |
| D16S3105 | 6.1 | SEQ ID No. 23 |
| (AFMb341zc5) | | SEQ ID No. 24 |
| D16S261 | 6.8 | SEQ ID No. 25 |
| (MFD24) | | SEQ ID No. 26 |
| D16S540 | 6.9 | SEQ ID No. 27 |
| (GATA7B02) | | SEQ ID No. 28 |
| D16S3080 | 7 | SEQ ID No. 29 |
| (AFMb068zb9) | | SEQ ID No. 30 |
| D16S517 | 7 | SEQ ID No. 31 |
| (AFMa132we9) | | SEQ ID No. 32 |
| D16S411 | 8 | SEQ ID No. 33 |
| (AFM186xa3) | | SEQ ID No. 34 |
| D16S3035 | 10.4 | SEQ ID No. 35 |
| (AFMa189wg5) | | SEQ ID No. 36 |
| D16S3136 | 10.4 | SEQ ID No. 37 |
| (AFMa061xe5) | | SEQ ID No. 38 |
| D16S541 | 11.4 | SEQ ID No. 39 |
| (GATA7E02) | | SEQ ID No. 40 |
| D16S3117 | 11.5 | SEQ ID No. 41 |
| (AFM288wb1) | | SEQ ID No. 42 |
| D16S416 | 12.4 | SEQ ID No. 43 |
| (AFM210yg3) | | SEQ ID No. 44 |
| D16S770 | 13.2 | SEQ ID No. 45 |

TABLE 1-continued

Polymorphic markers of the microsatellite type used for the fine location of IBD1

| Name of polymorphism marker | Cumulative distance (cM) | PCR primers |
|---|---|---|
| (GGAA20G02) | | SEQ ID No. 46 |
| D16S2623 | 15 | SEQ ID No. 47 |
| (GATA81B12) | | SEQ ID No. 48 |
| D16S390 | 16.5 | SEQ ID No. 49 |
| | | SEQ ID No. 50 |
| D16S419 | 20.4 | SEQ ID No. 51 |
| (AFM225zf2) | | SEQ ID No. 52 |
| D16S771 | 21.8 | SEQ ID No. 53 |
| (GGAA23C09) | | SEQ ID No. 54 |
| D16S408 | 25.6 | SEQ ID No. 55 |
| (AFM137xf8) | | SEQ ID No. 56 |
| D16S508 | 38.4 | SEQ ID No. 57 |
| (AFM304xf1) | | SEQ ID No. 58 |

Each marker is listed according to international nomenclature and mostly by the name proposed by the laboratory of origin. The markers appear according to their order on the chromosome (from 16p to 16q). The genetic distance between the markers (in Kosambi centiMorgans, calculated from the experimental data using the Crimap program) is indicated in the second column. The first polymorphic marker is taken randomly as a reference point. The oligonucleotides which were used for the polymerase chain reaction (PCR) are indicated in the third column.

The genotyping of these microsatellite markers was based on automatic sequencer technology using fluorescent primers. Briefly, after amplification, the fluorescent polymerase chain reaction (PCR) products were loaded onto a polyacrylamide gel on an automatic sequencer according to the manufacturer's recommendations (Perkin Elmer). The size of the alleles for each individual was deduced using the Genescan® and Genotyper® software. The data were then kept on an integrated computer base containing the genealogical, phenotypic and genetic data. They were then used for the genetic linkage analyses.

Several quality controls were carried out throughout the genotyping procedure:
independent double reading of the genotyping data,
use of a standard DNA as an internal control for each electrophoretic migration,
control of the size range for each allele observed,
search for mendelian transmission errors,
calculation of the genetic distance between markers (CRI-MAP program) and comparison of this distance with the data from the literature,
further typing of the markers for which recombination between close markers was observed.

Figure 2:
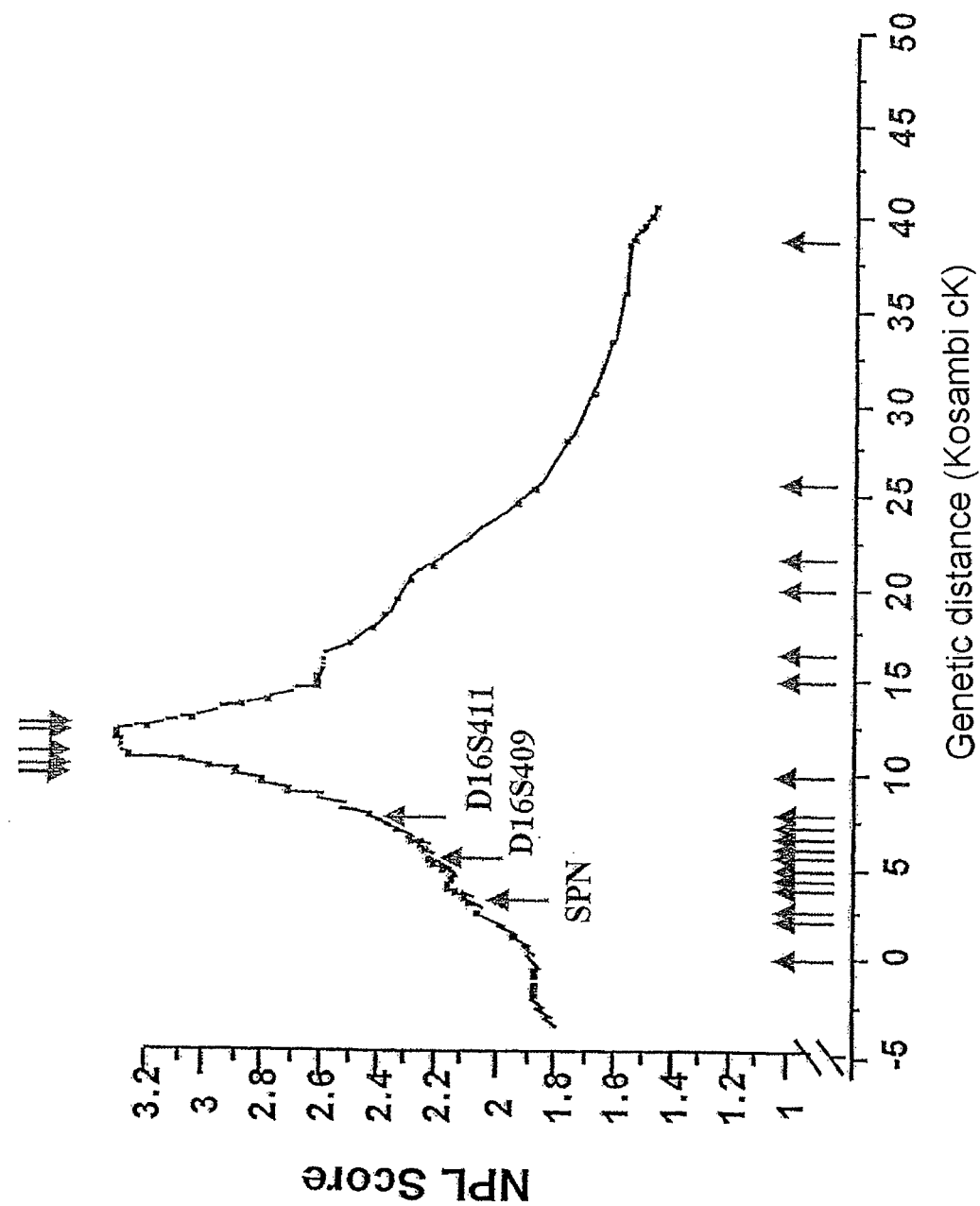
FIG. 2: Multipoint nonparametric genetic linkage analysis. 78 families with several relatives suffering from Crohn's disease were genotyped for 26 polymorphism markers in the pericentromeric region of chromosome 16. The location of each marker is symbolized by an arrow. The order of the markers and the distance separating them derive from the analysis of the experimental data with the Crimap software. The arrows under the curve indicate the markers SPN, D16S409 and D16S411 used in the first study published (Hugot et al., 1996). The arrows located at the top of the figure correspond to the markers D16S3136, D16S541, D16S3117, D16S416 and D16S770 located at the maximum of the genetic linkage test. The typing data were analyzed using the multipoint nonparametric analysis program of the Genehunter software version 1.3. The maximum NPL score is 3.33 (p=0.0004).

The genotyping data were analyzed by multipoint non-parametric genetic linkage methods (GENEHUNTER program version 1.3). The informativeness of the marker system was greater than 80% for the region studied. The test maximum (NPL=3.33; P=0.0004) was obtained for the markers D16S541, D16S3117, D16S770 and D16S416 (FIG. 2).

The typing data for these 26 polymorphism markers were also analyzed so as to search for a transmission disequilibrium. Two groups of 108 and 76 families with one or more sick individuals suffering from CD were studied. The statistical test for transmission disequilibrium has been described by Spielman et al. (1993). In this study, only one sick individual per family was taken into account, and the value of p was corrected by the number of alleles tested for each marker studied.

A transmission disequilibrium was observed for alleles 4 and 5 (size 205 and 207 base pairs, respectively) of the marker D16S3136 (p=0.05 and p=0.01, respectively).

These results, which suggest an association between the marker D16S3136 and CD, led to the construction of a physical map of the genetic region centered on D16S3136 and to establishment of the sequence of a large genomic DNA segment (BAC) containing this polymorphic site. It was then possible to identify and analyze a larger number of polymorphism markers in the region of D16S3136, and also to define and study the transcribed sequences present in the region.

Example 2

Physical Mapping of the IBD1 Region

A contig of genomic DNA fragments, centered on the markers D16S3136, D16S3117, D16S770 and D16S416, was generated from the human genomic DNA libraries of the Jean Dausset foundation/CEPH. The chromosomal DNA segments were identified based on certain polymorphism markers used in fine genetic mapping (D16S411, D16S416, D16S541, D16S770, D16S2623, D16S3035, D16S3117 and D16S3136). For each marker, a bacterial artificial chromosome (BAC) library was screened by PCR so as to search for clones containing the marker sequence. Depending on whether or not the sequences tested were present on the BAC clones, it was then possible to organize the clones among one another using the Segmap software version 3.35.

It was possible to establish, for the BACs, a continuous organization (contig) covering the genetic region of interest, according to a method known to those skilled in the art (Rouquier et al., 1994; Kim et al., 1996; Asakawa et al., 1997). To do this, the ends of the BACs identified were sequenced and these new sequence data were then used to repeatedly screen the BAC libraries. At each screening, the BAC contig then progressed by a step until a continuum of overlapping clones was obtained. The size of each BAC contributing to the contig was deduced from its migration profile on a pulsed field agarose gel.

A BAC contig containing 101 BACs and extending over an overall distance of more than 2.5 Mb, with an average redundancy of 5.5 BACs at each point of the contig, was thus constructed. The average size of the BACs is 136 kb.

Example 3

Sequencing of BAC hb87b10

The BAC of this contig containing the polymorphism marker D16S3136 (called hb87b10), the size of which was 163761 bp, was sequenced according to the "shotgun" method. Briefly, the BAC DNA was fragmented by sonication. The DNA fragments thus generated were subjected to agarose gel electrophoresis and those with a size greater than 1.5 kb were eluted in order to be analyzed. These fragments were then cloned into the m13 phage, which was itself introduced into bacteria made competent, by electroporation. After culturing, the DNA of the clones was recovered and sequenced by automatic sequencing methods using fluorescent primers of the m13 vector on an automatic sequencer.

1526 different sequences with an average size of 600 bp were generated, which were organized with respect to one another using the Polyphredphrap® software, resulting in a sequence contig covering the entire BAC. The sequence thus generated had an average redundancy of 5.5 genomic equivalents. The rare (n=5) sequence gaps not represented in the m13 clone library were filled by generating specific PCR primers, on either side of these gaps, and analyzing the PCR product derived from the genomic DNA of a healthy individual.

Sequence homologies with sequences available in public genetic databases (Genbank) were sought. No known gene could be identified in this region of 163 kb. Several ESTs were positioned, suggesting that unknown genes were contained in this sequence. These ESTs derived from the public genetic databases (Genbank, GDB, Unigene, dbEST) bore the following references: AI167910, AI011720, Rn24957, Mm30219, hs132289, AA236306, hs87296, AA055131, hs151708, AA417809, AA417810, hs61309, hs116424, HUMGS01037, AA835524, hs105242, SHGC17274, hs146128, hs122983, hs87280 and hs135201. The search for putative exons using the GRAIL computer program made it possible to identify several potential exons, polyadenylation sites and promoter sequences.

Example 4

Transmission Disequilibrium Studies 12 biallelic polymorphism markers (SNPs) were identified in a region extending over approximately 250 kb and centered on the BAC hb87b10. These polymorphisms were generated by analyzing the sequence of ten or so independent sick individuals suffering from CD. The sequencing was mostly carried out at known ESTs positioned on the BAC or in the region thereof. Putative exons, predicted by the GRAIL computer program, were also analyzed. The characteristics of the polymorphic markers thus identified are given in table 2.

the oligonucleotide primers used for the polymerase chain reaction or for the ligation (column V)
the size of the products expected during typing (column VI)

199 families comprising 1 or more sick individuals suffering from CD were typed for these 12 polymorphism markers and also for the markers D16S3035 and D16S3136 located on the BAC hb87b10. The families comprising sick individuals suffering from UC were not taken into account. The methods for typing the polymorphisms studied were variable depending on the type of polymorphism, using:

the PCR-RFLP technique (amplification followed by enzymatic digestion of the PCR product) when the polymorphism was located on an enzymatic restriction site.
PCR with primers specific for the polymorphic site: differential amplification of two alleles using primers specific for each allele.
Oligoligation test: differential ligation using oligonucleotides specific for each allele, followed by polyacrylamide gel electrophoresis.

The typing data were then analyzed using a transmission disequilibrium test (TDT computer program of the GENE-HUNTER software version 2). For the families comprising several affected relatives, a single sufferer was taken into account for the analysis. In fact, if several related sufferers are taken into account, this poses the problem of nonindependence of the data in the statistical calculations and can induce an inflation of the value of the test. The sufferer used for the analysis was drawn by lots, within each family, using an automatic randomization procedure. Given this randomization, the value of the statistical test obtained represented only one possible sample derived from the group of families stud-

TABLE 2

Characteristics of biallelic polymorphism markers studied in the region of IBD1

| I | II | III | IV | V | VI |
|---|---|---|---|---|---|
| 1 | KIAA0849ex9 | AS-PCR | | SEQ ID No. 88 to 90 | 116 |
| 2 | hb27G11F | PCR-RFLP | BsrI | SEQ ID No. 86, 87 | 185 |
| | | | | | 116 |
| | | | | | 69 |
| 3 | Ctg22Ex1 | PCR-RFLP | RsaI | SEQ ID No. 84, 85 | 381 |
| | | | | | 313 |
| | | | | | 69 |
| 4 | SNP1 | AS-PCR | | SEQ ID No. 81 to 83 | 410 |
| 5 | ctg2931-3ac/ola | LO | | SEQ ID No. 78 to 80 | 51 |
| | | | | | 49 |
| 6 | ctg2931-5ag/ola | LO | | SEQ ID No. 75 to 77 | 44 |
| | | | | | 42 |
| 7 | SNP3-2931 | AS-PCR | | SEQ ID No. 72 to 74 | 245 |
| 8 | Ctg25Ex1 | PCR-RFLP | BsteII | SEQ ID No. 70, 71 | 207 |
| | | | | | 122 |
| | | | | | 85 |
| 9 | CTG35ExA | AS-PCR | | SEQ ID No. 67 to 69 | 333 |
| 10 | ctg35ExC | AS-PCR | | SEQ ID No. 64 to 66 | 198 |
| 11 | D16S3136 | | | SEQ ID No. 37, 38 | |
| 12 | hb133D1f | PCR-RFLP | TaqI | SEQ ID No. 62, 63 | 369 |
| | | | | | 295 |
| | | | | | 74 |
| 13 | D16S3035 | | | SEQ ID No. 35, 36 | |
| 14 | ADCY7int7 | AS-PCR | | SEQ ID No. 59 to 61 | 140 |

AS-PCR: allele-specific PCR; LO: ligation of oligonucleotides

The 12 biallelic polymorphism markers newly described in this study are listed in this table. For each one of them, the following are indicated:
the locus (column I)
the name (column II)
the genotyping technique used (column III)
the restriction enzyme possibly used (column IV)

ied. So as not to limit the analysis to this one possible sample, and in order to understand more clearly the soundness of the results obtained, for each test, about one hundred random samples were thus generated and analyzed.

The markers were studied separately and then grouped according to their order on the chromosomal segment (KIAA0849ex9 (locus 1), hb27G11F (locus 2), Ctg22Ex1

(locus 3), SNP1 (locus 4), ctg2931-3ac/ola (locus 5), ctg2931-5ag/ola (locus 6), SNP3-2931 (locus 7), Ctg25Ex1 (locus 8), CTG35ExA (locus 9), ctg35ExC (locus 10), d16s3136 (locus 11), hb133D1f (locus 12), D16S3035 (locus 13), ADCY7int7 (locus 14)) (table 2). The haplotypes comprising 2, 3 and 4 consecutive markers were thus analyzed still using the same strategy (100 random samples, taking a single affected individual for each family).

For each sample tested, only the genotypes (or haplotypes) carried by at least 10 parental chromosomes were taken into account. On average, 250 different tests were thus carried out for each sample. It was then possible to deduce the number of tests expected to be positive for each significance threshold and to compare this distribution to the distribution observed. For the healthy individuals, the distribution of the tests is not different from that expected on a random basis ($\chi^2=2.85$, ddl=4, p=0.58). For the sick individuals, on the other hand, there is an excess of positive tests, reflecting the existence of a transmission disequilibrium in the region studied.

The results of the transmission disequilibrium test for each polymorphism marker taken separately or for the haplotypes showing the strongest transmission disequilibriums showed that the following markers and the disease are in linkage disequilibrium: Ctg22Ex1 (locus 3), SNP1 (locus 4), ctg2931-5ag/ola (locus 6), SNP3-2931 (locus 7), Ctg25Ex1 (locus 8) and ctg35ExC (locus 10). These markers extend over a region of approximately 50 kb (positions 74736 to 124285 on the sequence of hb87b10).

The haplotypes the most strongly associated with Crohn's disease themselves also extend over this region. Thus, for the majority of the random samples, the transmission test was positive (p<0.01) for haplotypes combining the following markers:

locus 5-6, locus 6-7, locus 7-8, locus 8-9, locus 9-10, locus 10-11
locus 5-6-7, locus 6-7-8, locus 7-8-9, locus 8-9-10, locus 9-10-11
locus 5-6-7-8, locus 6-7-8-9, locus 7-8-9-10.

The susceptibility haplotype most at risk is defined by the loci 7 to 10. This is the haplotype 1-2-1-2 (table 2).

The markers tested are, as expected, in linkage disequilibrium with respect to one another.

More recently, a new test, the Pedigree Disequilibrium Test (PDT), published in July 2000 (Martin et al., 2000), was used to understand more clearly the meaning of the results obtained with the TDT computer program. This new statistic in fact makes it possible to use all of the information available in a family, both from the sick individuals and from the healthy individuals, and to counterbalance the importance of each relative in an overall statistic for each family. The values of p corresponding to the PDT tests and obtained for an enlarged group of 235 families with one or more relatives suffering from Crohn's disease are given in table 3. This new analysis confirms that the region of the BAC hb87b10 is indeed associated with Crohn's disease.

TABLE 3

Results of the PDT tests carried out on 235 families suffering from Crohn's disease

| LOCUS | VALUE p OF THE PDT TEST |
| --- | --- |
| KIAA0849ex9 | NS |
| hb27g11f | 0.05 |
| ctg22ex1 | 0.01 |
| SNP1 | 0.001 |
| ctg2931-3ac/ola | NS |

TABLE 3-continued

Results of the PDT tests carried out on 235 families suffering from Crohn's disease

| LOCUS | VALUE p OF THE PDT TEST |
| --- | --- |
| ctg2931-5ag/ola | 0.0001 |
| SNP3-2931 | 0.0001 |
| ctg25ex1 | 0.0006 |
| ctg35exA | NS |
| ctg35exC | 0.00002 |
| D16S3136 | NS |
| hb133d1f | NS |
| D16S3035 | NS |

(NS: not significant)

Example 5

Identification of the IBD1 Gene

The published EST groups (Unigene references: Hs 135201, Hs87280, Hs122983, Hs146128, Hs105242, Hs116424, Hs61309, Hs151708, Hs 87296 and Hs132289) present on the BAC hb87b10 were studied in the search for a more complete complementary DNA (cDNA) sequence. For IBD1prox, the clones available in public libraries were sequenced and the sequences were organized with respect to one another. For IBD1, a peripheral blood complementary DNA library (Stratagene human blood cDNA lambda zapexpress ref 938202) was screened with the PCR products generated from known ESTs according to the methods proposed by the manufacturer. The sequence of the cDNAs thus identified was then used for further screening of the cDNA library, and so on, until the presented cDNA was obtained.

The EST hs135201 (UniGene) made it possible to identify a cDNA not appearing on the available genetic databases (Genbank). It therefore corresponds to a new human gene. Comparison of the sequence of the cDNA and of the genomic DNA showed that this gene consists of 11 exons and 10 introns. An additional exon, positioned 5' to the cDNA identified, is predicted by analysis of the sequence with the Grail program. These exons are very homologous to the first exons of the CARD4/NOD1 gene. Taking into consideration all of the exons identified and the putative additional exon, this new gene appears to have a genomic structure very close to that of CARD4/NOD1. Moreover, a transcription initiation site appears upstream of the first putative exon. For all of these reasons, the putative exon was considered to contribute to this new gene. The cDNA reproduced in the annex (SEQ ID No. 1) therefore comprises all of the identified sequence plus the sequence predicted by the computer modeling, the complementary DNA beginning randomly at the first ATG codon of the predicted coding sequence. On this basis, the gene would therefore comprise 12 exons and 11 introns. The intron-exon structure of the gene is reported on SEQ ID No. 3.

The protein sequence deduced from the nucleotide sequence comprises 1041 amino acids (SEQ ID No. 2). This sequence has not been found on the biological databases either (Genpept, pir, swissprot).

Now, more recently, it has not been possible to confirm the putative exon described above. The IBD1 gene therefore effectively comprises only 11 exons and 10 introns and encodes a protein of 1013 amino acids (i.e. 28 amino acids less than initially determined).

Figure 3:
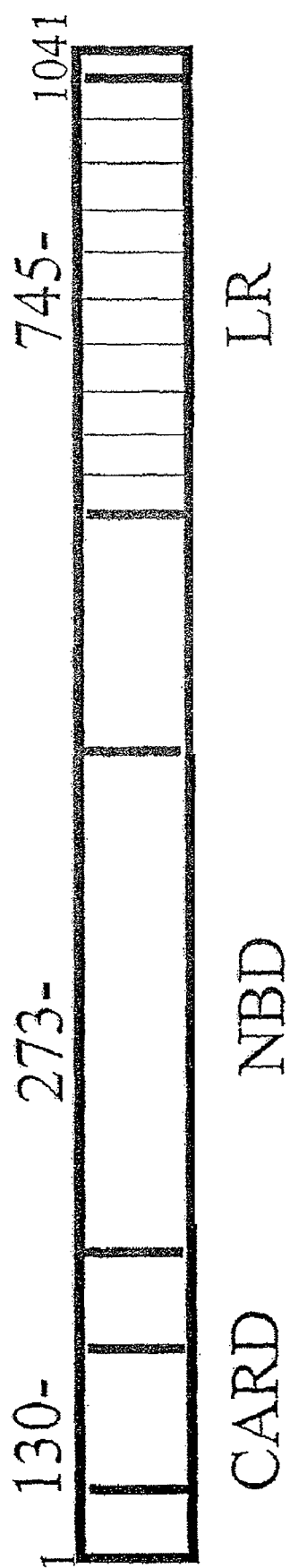
FIG. 3: Diagrammatic representation of the protein encoded by IBD1. The protein encoded by IBD1 is represented horizontally. The various domains of which it is composed are indicated on the figure with the amino acid reference number corresponding to the start and to the end of each domain. The protein consists of a CARD domain, a nucleotide-binding domain (NBD) and leucine-rich motifs (LRR).

The study of the deduced protein sequence shows that this gene contains three different functional domains (FIG. 3):

A CARD domain (Caspase Recruitment Domain) known to be involved in the interaction between proteins regulating apoptosis and activation of the NFkappa B pathway. The CARD domain makes it possible to classify this new protein in the CARD protein family, the most longstanding members of which are CED4, APAF1 and RICK.

An NBD domain (Nucleotide-Binding Domain) comprising an ATP-recognition site and a magnesium-binding site. The protein should therefore very probably have kinase activity.

An LRR domain (Leucine-Rich Domain) presumed to participate in the interaction between proteins, by analogy with other described protein domains.

Moreover, the LRR domain of the protein makes it possible to affiliate the protein to a family of proteins involved in intracellular signaling and present both in plants and in animals.

Comparison of this new gene with previously identified genes available in the public databases shows that this gene is very homologous to CARD4/NOD1 (Bertin et al., 1999; Inohara et al., 1999). This homology relates to the sequence of the complementary DNA, the intron-exon structure of the gene and the protein sequence. The sequence identity of the two complementary DNAs is 58%. A similarity is also observed at the level of the intron-exon structure. The sequence homology at the protein level is of the order of 40%.

The similarity between this new gene and CARD4/NOD1 suggests that, like CARD4/NOD1, the IBD1 protein is involved in the regulation of apoptosis and of the activation of NF-kappa B (Bertin et al., 1999; Inohara et al., 1999). The regulation of cellular apoptosis and activation of NF-kappa B are intracellular signaling pathways which are essential in immune reactions. Specifically, these signal translation pathways are the effector pathways of the proteins of the TNF (Tumor Necrosis Factor) receptor family involved in cell-cell interactions and the cellular response to the various mediators of inflammation (cytokines). The new gene therefore appears to be potentially important in the inflammatory reaction in general.

Several bodies of proof support bacteria-induced deregulation of NF-kB in Crohn's disease. First of all, spontaneous susceptibility to IBD in mice has been associated with mutations in Tlr4, a molecule known to bind to LPS via its LRR domain (Poltorak et al., 1998 and Sundberg et al., 1994) and to be a member of the activators of the NF-kB family. Second, treatment with antibiotics causes a provisional improvement in patients suffering from CD, giving credit to the hypothesis that enteric bacteria may play an etiological role in Crohn's disease (McKay, 1999). Third, NF-kB plays a pivotal role in inflammatory bowel diseases and is activated in lamina propria mononuclear cells in Crohn's disease (Schreiber et al., 1998). Fourth, the treatment of Crohn's disease is based on the use of sulfasalazine and glucocorticoids, which are both known to be NF-kB inhibitors (Auphan et al., 1995 and Wahl et al., 1998).

Even more recently, it has been shown that the IBD1 candidate gene encodes a protein very similar to NOD2, a member of the CED4/APAF1 superfamily (Ogura et al., 2000). The nucleotide and protein sequences of IBD1 and NOD2 in reality only diverge for a small portion right at the start of the two reported sequences. The tissue expressions of Nod2 and IBD1 can, in addition, be superimposed. These two genes (proteins) can therefore be considered to be identical. It has been demonstrated that the LRR domain of Nod2 has binding activity for bacterial lipopolysaccharides (LPS) (Inohara et al., 2000) and that deletion thereof stimulates the NFkB pathway. This result confirms the data of the invention.

The tissue expression of IBD1 was then studied by Northern blotting. A 4.5 kb transcript is visible in most human tissues. The size of the transcript is in accordance with the size predicted by the cDNA. The 4.5 kb transcript appears to be very poorly abundant in the small intestine and the colon. It is, on the other hand, very strongly expressed in white blood cells. This is in agreement with clinical data on transplants which suggest that Crohn's disease is potentially a disease associated with circulating immune cells. In fact, bowel transplantation does not prevent recurrence on the transplant in Crohn's disease, whereas bone marrow transplantation appears to have a beneficial effect on the progression of the disease.

Certain data also call to mind alternative splicing, which may prove to be an important element in the possibility of generating mutants which may play a role in the development of inflammatory diseases.

The promoter of the IBD1 gene has not currently been identified with precision. It is, however, reasonable to think, by analogy with a very large number of genes, that this promoter lies, at least partly, immediately upstream of the gene, in the 5' portion thereof. This genetic region contains transcribed sequences, as witnessed by the presence of ESTs (HUMGS01037, AA835524, hs.105242, SHGC17274, hs.146128, hs.122983, hs.87280). The ATCC clones containing these sequences were sequenced and analyzed in the laboratory, making it possible to demonstrate an exon and intron organization with possible alternative splicings. These data suggest the existence of another gene (named IBD1prox due to its proximity to IBD1). The partial sequence of the complementary DNA of IBD1prox is reported (SEQ ID No. 4), as is its intron-exon structure, on SEQ ID No. 6.

Translation of the cDNAs corresponding to IBD1prox results in a protein containing a homeobox. Analysis of several cDNAs of the gene suggests, however, the existence of alternative splicings. IBD1prox, according to one of the possible alternative splicings, corresponds to the anonymous EST HUMGS01037, the RNA of which is expressed more strongly in differentiated leukocytic lines than in undifferentiated lines.

Thus, it is possible that this gene may have a role in inflammation and cell differentiation. It may therefore also, itself, be considered to be a good candidate for susceptibility to IBD. The association between CD and the polymorphism ctg35ExC located on the coding sequence of IBD1prox supports this hypothesis even though this polymorphism does not cause any sequence variation at the protein level.

Finally, more recently, the existence of a genetic linkage in families suffering from Crohn's disease and not comprising any mutation in the IBD1 gene also, itself, suggests that IBD1prox has a role in addition to IBD1 in genetic predisposition to the disease.

The functional relationship between IBD1 and IBD1prox is not currently established. However, the considerable proximity between the two genes may reflect an interaction between them. In this case, the "head-to-tail" location of these genes suggests that they may have common or interdependent methods of regulation.

Example 6

Identification of IBD1 Gene Mutations in Inflammatory Diseases

In order to confirm the role of IBD1 in inflammatory diseases, the coding sequence and the intron-exon junctions of the gene were sequenced from exon 2 to exon 12 inclusive, in 70 independent individuals, namely: 50 sick individuals suffering from CD, 10 sick individuals suffering from UC, 1 sick individual suffering from Blau's syndrome and 9 healthy controls. The sick individuals studied were mostly familial forms of the disease and were often carriers of the susceptibility haplotype defined by the transmission disequilibrium studies. The healthy controls were of Caucasian origin.

It was thus possible to identify 24 sequence variants on this group of 70 unrelated individuals (table 3).

The nomenclature of the mutations reported refers to the initial sequence of the protein comprising 1 041 amino acids. The more recently proposed nomenclature is easily deduced by removing 28 amino acids from the initial sequence, and therefore corresponds to a protein comprising 1 013 amino acids (cf. example 5).

TABLE 4

Mutations observed in the IBD1 gene

| Exon | Nucleotide variant | Protein variant | Crohn's disease | Ulcerative colitis | Health controls |
|---|---|---|---|---|---|
| 1 | Not tested | | | | |
| 2 | G417A | Silent | | | |
| 2 | C537G | Silent | | | |
| 3 | None | | | | |
| 4 | T805C | S269P | 48/100 | 6/20 | 3/18 |
| 4 | A869G | N290S | 0 | 0 | 1/18 |
| 4 | C905T | A302V | 1/100 | 0 | 0 |
| 4 | C1283T | P428L | 1/100 | 0 | 0 |
| 4 | C1284A | Silent | | | |
| 4 | C1287T | Silent | | | |
| 4 | T1380C | Silent | | | |
| 4 | T1764G | Silent | | | |
| 4 | G1837A | A613T | 1/100 | 0 | 0 |
| 4 | C2107T | R703W | 10/10 | 1/20 | 1/18 |
| 4 | C2110T | R704C | 4/10 | 1/20 | 0 |
| 5 | G2365A | R792Q | 1/100 | 0 | 0 |
| 5 | G2370A | V794M | 0 | 1/20 | 0 |
| 5 | G2530A | E844K | 1/10 | 0 | 0 |
| 6 | A2558G | N853S | 1/100 | 0 | 0 |
| 6 | A2590G | M864V | 1/100 | 0 | 0 |
| 7 | None | | | | |
| 8 | G2725C | G909R | 7/100 | 0 | 0 |
| 8 | C2756A | A919D | 1/100 | 0 | 0 |
| 9 | G2866A | V956I | 2/100 | 1/20 | 3/18 |
| 10 | C2928T | Silent | | | |
| 11 | 3022insC | Stop | 20/100 | 0 | 0 |
| 12 | none | | | | |

The mutations other than silent mutations observed in each exon are reported. They are indicated by the variation in the peptide chain. For each mutation and for each phenotype studied, the number of times where the mutation is observed, related to the number of chromosomes tested, is indicated.

No functional sequence variant was identified in exons 1 to 3 (corresponding to the CARD domain of the protein). Exons 7 and 12 did not show any sequence variation either. Certain variants corresponded to polymorphisms already identified and typed for transmission disequilibrium studies, namely:

Snp3-2931: nucleotide variant T805C, protein variant S269P
ctg2931-5ag/ola: nucleotide variant T1380C (silent)
ctg2931-3ac/ola: nucleotide variant T1746G (silent)
SNP1: nucleotide variant C2107T, protein variant R703W.

Several sequence variations were silent (G417A, C537G, C1284A, C1287T, T1380C, T1764G and C2928T) and did not lead to any modification of the protein sequence. They were not studied further here.

For the 16 non-silent sequence variations, protein sequence variants were observed in 43/50 CD versus 5/9 healthy controls, and 6/10 UC. The existence of one or more sequence variation(s) appeared to be associated with the CD phenotype. Several sequence variations often existed in the same individual suffering from CD, suggesting a sometimes recessive effect of the gene for CD. On the other hand, no composite heterozygote or homozygote was observed among the patients suffering from UC or among the healthy controls.

Some non-silent variants were present both in the sick individuals suffering from UC or from CD and in the healthy individuals. They were the variants S269P, N290S, R703W and V956I located in exons 2, 4 and 9. Further information therefore appears to be necessary before selecting a possible functional role for these sequence variants.

V956I is a conservative sequence variation (aliphatic amino acids).

The sequence variant S269P corresponds to a variation in amino acid class (hydroxylated to immuno acid) at the beginning of the nucleotide-binding domain. This sequence variant and CD are in transmission disequilibrium. It is in fact the polymorphism Snp3 (cf. above).

R703W results in a modification of the amino acid class (aromatic instead of basic). This modification occurs in the intermediate region between the NBD and LRR domains, which is a region conserved between IBD1 and CARD4/NOD1. A functional role may therefore be suspected for this polymorphism. This sequence variation (corresponding to the polymorphic site Snp1) is transmitted to sick individuals suffering from CD more often than at random (cf. above), confirming that this polymorphism is associated with CD. It is possible that the presence of this mutant in healthy individuals reflects incomplete penetrance of the mutation as is expected for complex genetic diseases such as chronic inflammatory bowel diseases.

The variant R704C, located immediately next to R703W, could be identified in both CD and UC. It also, itself, corresponds to a nonconservative variation of the protein (sulfur-containing amino acid instead of basic amino acid) on the same protein region, suggesting a functional effect for R704C which is as important as that for R703W.

Other sequence variations are specific for CD, for UC or for Blau's syndrome.

Some sequence variations are, on the contrary, rare, present in one or a few sick individuals (A613T, R704C, E844K, N853S, M864V, A919D). They are always variations leading to nonconservative modifications of the protein in leucine-rich domains, at positions which are important within these domains. These various elements suggest that these variations have a functional role.

Two sequence variations (G909R and L1008P*) are found in quite a large number of Crohn's diseases (respectively 7/50 and 16/50) whereas they are not detected in the controls or in the individuals suffering from UC.

The deletion/insertion of a guanosine at codon 1008 results in transformation of the third leucine of the alpha helix of the last LRR to proline followed by a STOP codon (L1008P*). This sequence variation therefore leads to an important modification of the protein: decrease in size of the protein (protein having a truncated LRR domain) and modification of a very conserved amino acid (leucine). This sequence modification is associated with CD, as witnessed by a transmission disequilibrium study in 16 families carrying the mutation (P=0.008).

The mutation G909R occurs on the last amino acid of the sixth LRR motif. It replaces an aliphatic amino acid with a basic amino acid. This variation is potentially important given the usually neutral or polar nature of the amino acids in the terminal position of the leucine-rich motifs (both for IBD1 and for NOD1/CARD4) and the conserved nature of this amino acid on the IBD1 and NOD1/CARD4 proteins.

In Blau's syndrome, the sick individuals (n=2) of the family studied carried a specific sequence variation (L470F) located in exon 4 and corresponding to the NBD domain of the protein. In this series, this sequence variant was specific for Blau's syndrome.

In UC, several sequence variants not found in healthy individuals were also identified. The proportion of sick individuals carrying a mutation was smaller than for CD, as expected given the less strongly established linkage between IBD1 and UC, and the supposedly less genetic nature of the latter disease. Sequence variations were common to CD and to UC (R703W, R704C). Others, on the other hand, appeared to be specific for UC (V794M). This observation makes it possible to confirm that CD and UC are diseases which, at least partly, share the same genetic predisposition. It lays down the foundations of a nosological classification for IBDs.

The study of the sequence variants of the IBD1 gene has therefore made it possible to identify several variants having a very probable functional effect (for example: truncated protein) and associated with Crohn's disease, with UC and with Blau's syndrome.

The promoter of the gene is not currently determined. In all probability, however, it is likely to be located in the 5' region upstream of the gene. According to this hypothesis, the sequence variants observed in this region may have a functional effect. This may explain the very strong association between CD and certain polymorphic loci, such as ctg35ExC or Ctg25Ex1.

The invention thus provides the first description of mutations in the family of genes containing a CARD domain in humans. The frequency of these mutations in various inflammatory diseases shows that the IBD1 gene has an essential role in normal and pathological inflammatory processes. This invention provides new paths of understanding and of research in the field of the physiopathology of normal and pathological inflammatory processes. As a result, it makes it possible to envision the development of new pharmaceutical molecules which regulate the effector pathways controlled by IBD1 and which are useful in the treatment of inflammatory diseases and in the regulation of inflammatory processes in general.

Example 7

Bases for a Biological Diagnosis of Susceptibility to Crohn's Disease

More recently, 457 independent patients suffering from Crohn's disease, 159 independent patients suffering from ulcerative colitis and 103 healthy controls were studied in the search for mutations. This study made it possible to confirm the mutations previously reported and to identify additional mutations, reported in FIG. 4. The main mutations were then genotyped in 235 families suffering from Crohn's disease. This more recent study is reported using, as reference, the shorter protein sequence (1 013 amino acids, see example 5), but the prior nomenclature for the mutations is easily deduced from the latter by adding 28 to the number indicating the position of the amino acids.

Among the 5 most common mutations, the conservative mutation V928I (formerly V956I) is not significantly associated with one or the other of the inflammatory bowel diseases, and does not therefore appear to have an important role in the disease.

The mutation S241P (formerly S269P) is in linkage disequilibrium with the other main mutations and does not appear to play an important role, by itself, in susceptibility to inflammatory bowel diseases (data not shown).

Figure 4:
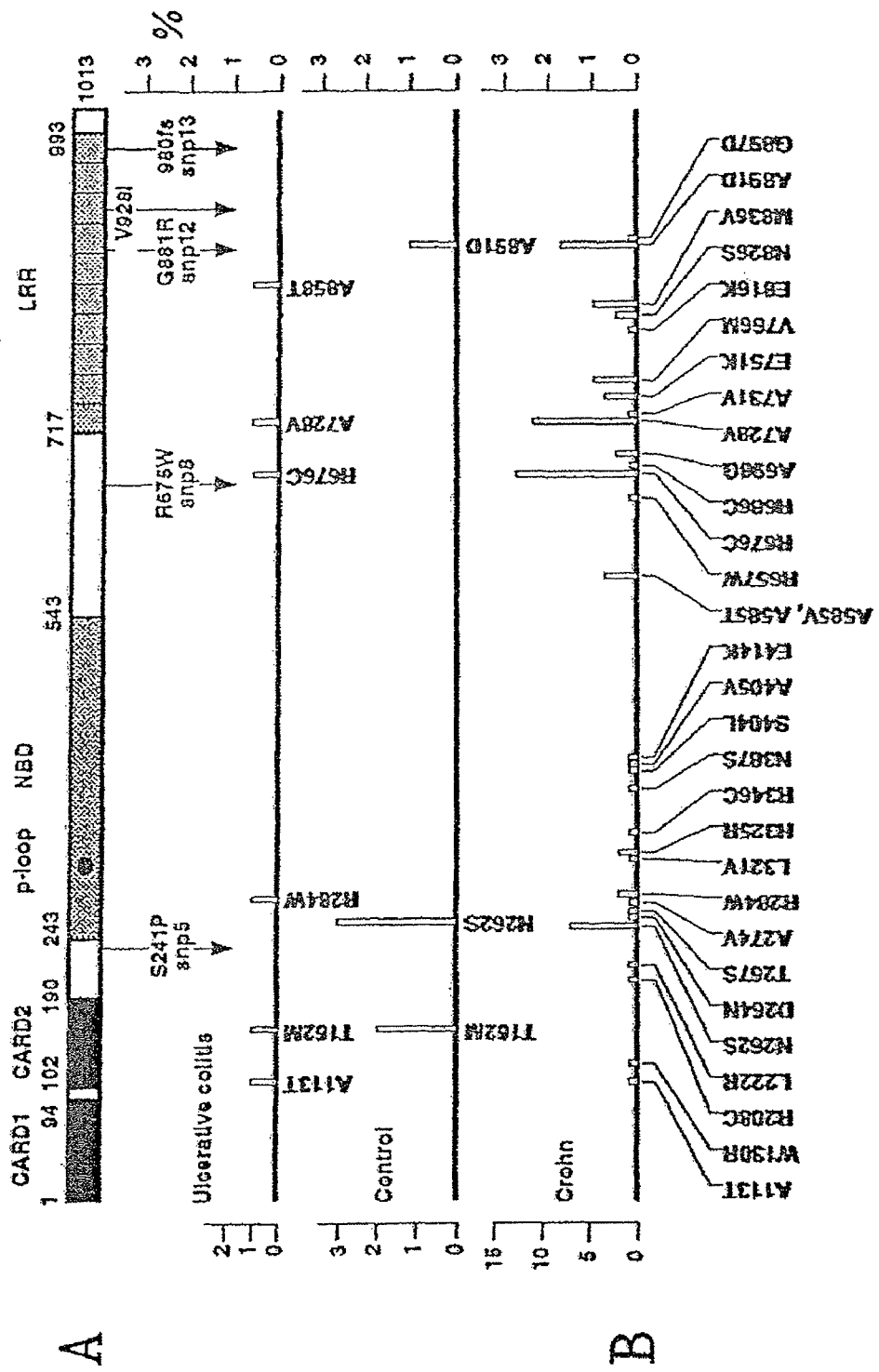
FIG. 4: Diagrammatic representation of the IBD1/NOD2 protein in three variants associated with CD.

Conversely, the other 3 mutations, R675W (formerly R703W), G881R (formerly G909R) and 980fs (formerly L1008P*), are significantly associated with Crohn's disease but not with ulcerative colitis (cf. below). The location in the LRR, or in its immediate proximity, of the 3 common mutations pleads very strongly in favor of a functional mechanism involving this protein domain, probably via a defect in negative regulation of NFkB by the mutated protein. The other mutations are more rare (FIG. 4). These cumulative mutations are present in 17% of the individuals suffering from Crohn's disease versus, respectively, 4% and 5% of the healthy individuals or individuals suffering from ulcerative colitis. A large number of rare mutations are also located in the LRR.

The intrafamily studies of the three polymorphisms most common in Crohn's disease show that all three are associated with the disease (table 5). As expected, for a mutation supposed to be very deleterious, the polymorphism most strongly associated is the truncating mutation. These three polymorphisms are independently associated with Crohn's disease, since it was not possible to identify, on 235 families, chromosomes carrying more than one of these three mutations. The independent nature of these associations considerably supports the hypothesis that the IBD1 gene is clearly involved in genetic predisposition to Crohn's disease.

TABLE 5

Study of the 3 common polymorphisms of IBD1 in 235 families suffering from Crohn's disease

| MUTATION | VALUE p OF THE PDT TEST |
|---|---|
| R675W | 0.001 |
| G881R | 0.003 |
| 980fs | 0.000006 |

The case-control studies confirm this association (table 6). They show that the mutations most common in Crohn's disease are not common in ulcerative colitis.

TABLE 6

Case-control study of the 3 common polymorphisms of IBD1 in inflammatory bowel diseases

| MUTATION | No. OF CHROMOSOMES STUDIED | FREQUENCY OF THE ALLELE AT RISK R675W | FREQUENCY OF THE ALLELE AT RISK G881R | FREQUENCY OF THE ALLELE AT RISK 980fs | TOTAL ALLELES AT RISK |
|---|---|---|---|---|---|
| Healthy controls | 206 | 0.04 | 0.01 | 0.02 | 0.07 |
| Ulcerative colitis | 318 | 0.03 | 0.00 | 0.01 | 0.05 |
| Crohn's disease | 936 | 0.11 | 0.06 | 0.12 | 0.29 |

The study of the dose-effect of these mutations shows that individuals carrying a mutation in the homozygous or composite heterozygous state exhibit a much greater risk of developing the disease than individuals who are not carrying or are heterozygous for these mutations (table 7).

TABLE 7

Relative and absolute risk of Crohn's disease attributable as a function of the genotype of IBD1

| | Distribution GENOTYPE | | | |
|---|---|---|---|---|
| | No VARIANT | SIMPLE HETERO-ZYGOTE | HOMO-ZYGOTE | COMPOSITE HETERO-ZYGOTE |
| Healthy | 88 | 15 | 0 | 0 |
| Ulcerative colitis | 145 | 13 | 1 | 0 |
| Crohn's disease | 267 | 133 | 28 | 40 |
| Attributable risk of CD: | | | | |
| Relative risk | 1 | 3 | 38 | 44 |
| Absolute risk | 0.0007 | 0.002 | 0.03 | 0.03 |

In the general population, a risk of Crohn's disease of 0.001 has been taken as a reference, and it has been presumed that the mutations are in Hardy-Weinberg equilibrium.

The studies mentioned above confirm the prior preliminary data and provide the detailed bases for a biological diagnosis of Crohn's disease by studying the IBD1 variants. In fact, this work:

1) defines the mutations, the frequency of which is greater than 0.001 in a mixed Caucasian population;
2) defines the frequency of the mutations observed and makes it possible to define 3 main mutations associated with Crohn's disease. Thus, it is possible, by virtue of this work, to define a strategy for studying the gene in order to search for morbid variants, namely: firstly, typing the 3 main mutations; secondly, searching for mutations in the last 7 exons; thirdly, searching for other sequence variants;
3) defines the practical modalities for searching for these mutations by pointing out their position and their nature. In fact, it is then easy for those skilled in the art to develop typing and sequencing methods according to their personal expertise. Mention may in particular be made of the possibility of genotyping the three main mutations by PCR followed by enzymatic digestion and electrophoresis, study of the migration profiles by dHPLC, DGGE or SSCP, oligoligation, microsequencing, etc.;
4) demonstrates the independence of the most common mutations which are not observed on the same chromosome in this extended and varied population. This information makes it possible to reliably classify the individuals who are composite heterozygotes (having two mutations) as carriers with a double dose of intragenic variations;
5) demonstrates that the great majority of the mutations only lead to a null or minimal effect on the risk of ulcerative colitis. This result makes it possible to envision assisting the clinician in the differential diagnosis between these two diseases. In fact, in approximately 10% of cases, inflammatory bowel diseases remain unclassified despite biological, radiological and endoscopic examination;
6) defines a relative and absolute risk of disease for the most common genotypes. This result lays down the foundations of a predictive diagnosis potentially useful in an approach of preventive monitoring and intervention in populations at risk, in particular the relatives of sick individuals;
7) demonstrates the existence of a dose-effect for the IBD1 gene and confirms the partly recessive nature of genetic predisposition to Crohn's disease. It therefore makes it possible to lay the foundations for genetic counseling and for intra-familial preclinical diagnosis.

Finally, it should be noted that an additional mutation of the NBD domain was isolated in a second family carrying Blau's syndrome. The rareness of the two events in 2 different families is sufficient to confirm the involvement of this gene in Blau's syndrome and in granulomatous diseases in general.

All of these data provide a diagnostic tool which is directly applicable and of use to the practitioner in his or her daily practice.

The IBD1prox gene, located in the promoter region of IBD1, and the partial sequence of which is disclosed in the present invention, may also, itself, have an important role in the regulation of cellular apoptosis and of the inflammatory process, as suggested by its differential expression in mature cells of the immune system. The strong association reported in this work between the polymorphism marker ctg35ExC (located in the transcribed region of the gene) and Crohn's disease also pleads very strongly in favor of this hypothesis.

Inflammatory bowel diseases are complex genetic diseases for which, until now, no susceptibility gene had been identified with certainty. The invention has made it possible to identify the first gene for susceptibility to Crohn's disease, using a positional cloning (or reverse genetics) approach. This is the first genetic location obtained using such an approach for a complex genetic disease, which demonstrates its usefulness and its feasibility, at least in certain cases in complex genetic diseases.

The present invention also relates to a purified or isolated nucleic acid, characterized in that it encodes a polypeptide possessing a continuous fragment of at least 200 amino acids of a protein chosen from SEQ ID No. 2 and SEQ ID No. 5.

REFERENCES

Auphan et al. (1995), Science 270, 286-90.
Asakawa et al. (1997), Gene, 191, 69.
Becker et al. (1998), Proc. Natl. Acad. Sci. USA, 95, 9979.
Bertin et al. (1999), J. Biol. Chem., 274, 12955.
Buckholz (1993), Curr. Op. Biotechnology 4, 538.
Carter, (1993), Curr. Op. Biotechnology 3, 533.
Cho et al. (1998), Proc. Natl. Acad. Sci. USA, 95, 7502.
Duck et al. (1990), Biotechniques, 9, 142.
Edwards and Aruffo (1993), Curr. Op. Biotechnology, 4, 558.
Epstein (1992), Medicine/Sciences, 8, 902.
Guatelli et al. (1990), Proc. Natl. Acad. Sci. USA 87: 1874.
Hugot et al. (1996), Nature, 379, 821.
Inohara et al. (1999), J. Biol. Chem., 274, 14560.
Inohara et al. (2000), J. Biol. Chem.
Kievitis et al. (1991), J. Virol. Methods, 35, 273.
Kim et al. (1996), Genomics, 34, 213.
Köhler and Milstein (1975), Nature, 256, 495.
Kwoh et al. (1989), Proc. Natl. Acad. Sci. USA, 86, 1173.
Landegren et al. (1988), Science 241, 1077.
Lander and Kruglyak (1995), Nat. Genet., 11, 241.
Luckow (1993), Curr. Op. Biotechnology 4, 564.
Martin et al. (2000), Am. J. Hum. Genet. 67: 146-54.
Matthews et al. (1988), Anal. Biochem., 169, 1-25.
McKay (1999), Gastroenterol. 13, 509-516.
Miele et al. (1983), J. Mol. Biol., 171, 281.
Neddleman and Wunsch (1970), J. Mol. Biol. 48: 443.
Ogura et al. (2000), J. Biol. Chem.
Olins and Lee (1993), Curr. Op. Biotechnology 4: 520.
Perricaudet et al. (1992), La Recherche 23: 471.

Pearson and Lipman (1988), Proc. Natl. Acad. Sci. USA 85: 2444.
Poltorak et al. (1998), Sciences 282, 2085-8.
Rioux et al. (1998), Gastroenterology, 115: 1062.
Rohlmann et al. (1996), Nature Biotech. 14: 1562.
Rolfs, A. et al. (1991), Berlin: Springer-Verlag.
Rouquier et al. (1994), Anal. Biochem. 217, 205.
Sambrook et al. (1989), Molecular cloning: a laboratory manual, 2nd ed. Cold Spring Harbor Lab., Cold Spring Harbor, N.Y.
Satsangi et al. (1996), Nat. Genet., 14: 199.
Schreiber et al. (1998), Gut 42, 477-84.
Segev (1992), Kessler C. Springer Verlag, Berlin, New York, 197-205.
Smith and Waterman (1981) Ad. App. Math. 2: 482.
Steward and Yound (1984), Solid phase peptides synthesis, Pierce Chem. Company, Rockford, 111, 2nd ed. (1984).
Spielman et al. (1993), Am. J. Hum. Genet., 52, 506.
Sundberg et al. (1994), Gastroenterology, 107, 1726-35.
Temin (1986), Retrovirus vectors for gene transfer. In Kucherlapati R., ed. Gene Transfer, New York, Plenum Press, 149-187.
Tromp et al. (1996), Am. J. Hum. Genet., 59: 1097.
Wahl et al. (1998), B. J. Clin. Invest. 101, 1163-74.
Walker (1992), Nucleic Acids Res. 20: 1691.

What is claimed is:

1. A method for identifying a human subject having an increased risk of Crohn's disease, said method comprising:
   (a) contacting a biological specimen from said human subject with a nucleic acid probe specific for a variant nucleic acid sequence selected from the group consisting of SEQ ID NO:3 having a C to T mutation at nucleotide 16467, SEQ ID NO:3 having a G to C mutation at nucleotide 27059, and SEQ ID NO:3 having a C insertion at nucleotide 34296;
   (b) determining the presence or absence of said variant nucleic acid sequence by detecting hybridization between said nucleic acid probe and said variant nucleic acid sequence; and
   (c) identifying a human subject carrying said variant nucleic acid sequence in homozygous form as having an increased risk of Crohn's disease in comparison to a human subject carrying said variant nucleic acid sequence in heterozygous form or a human subject not carrying said variant nucleic acid sequence.

2. The method of claim 1, wherein the presence or absence of said variant nucleic acid sequence of SEQ ID NO:3 having a C to T mutation at nucleotide 16467 is determined.

3. The method of claim 1, wherein the presence or absence of said variant nucleic acid sequence of SEQ ID NO:3 having a G to C mutation at nucleotide 27059 is determined.

4. The method of claim 1, wherein the presence or absence of said variant nucleic acid sequence of SEQ ID NO:3 having a C insertion at nucleotide 34296 is determined.

5. The method of claim 1, wherein the presence or absence of at least 2 of said variant nucleic acid sequences is determined.

6. The method of claim 1, wherein the presence or absence of 3 of said variant nucleic acid sequences is determined.

7. The method of claim 1, wherein said nucleic acid probe comprises a detectable label.

8. The method of claim 7, wherein said detectable label is a fluorescent label.

9. The method of claim 1, wherein said biological specimen is genomic DNA.

10. The method of claim 1, further comprising contacting said biological specimen with a pair of nucleic acid primers specific for nucleic acid sequences bordering said variant nucleic acid sequence.

11. The method of claim 1, wherein said nucleic acid probe is at least 15 nucleotides in length.

12. An assay method for determining the presence or absence of a variant nucleic acid sequence in a NOD2 gene in a human subject, said method comprising:
   (a) contacting a biological specimen from said human subject with a nucleic acid probe specific for a variant nucleic acid sequence selected from the group consisting of SEQ ID NO:3 having a C to T mutation at nucleotide 16467, SEQ ID NO:3 having a G to C mutation at nucleotide 27059, and SEQ ID NO:3 having a C insertion at nucleotide 34296; and
   (b) determining the presence or absence of said variant nucleic acid sequence by detecting hybridization between said nucleic acid probe and said variant nucleic acid sequence.

13. The method of claim 12, wherein the presence or absence of said variant nucleic acid sequence of SEQ ID NO:3 having a C to T mutation at nucleotide 16467 is determined.

14. The method of claim 12, wherein the presence or absence of said variant nucleic acid sequence of SEQ ID NO:3 having a G to C mutation at nucleotide 27059 is determined.

15. The method of claim 12, wherein the presence or absence of said variant nucleic acid sequence of SEQ ID NO:3 having a C insertion at nucleotide 34296 is determined.

16. The method of claim 12, wherein the presence or absence of at least 2 of said variant nucleic acid sequences is determined.

17. The method of claim 12, wherein the presence or absence of 3 of said variant nucleic acid sequences is determined.

18. The method of claim 12, wherein said nucleic acid probe comprises a detectable label.

19. The method of claim 18, wherein said detectable label is a fluorescent label.

20. The method of claim 12, wherein said biological specimen is genomic DNA.

21. The method of claim 12, further comprising contacting said biological specimen with a pair of nucleic acid primers specific for nucleic acid sequences bordering said variant nucleic acid sequence.

22. The method of claim 12, wherein said nucleic acid probe is at least 15 nucleotides in length.

* * * * *